United States Patent
Brahmbhatt et al.

(10) Patent No.: US 12,337,033 B2
(45) Date of Patent: Jun. 24, 2025

(54) ENCAPSULATED GLYCOLIPID ANTIGENS FOR TREATMENT OF NEOPLASTIC DISEASES

(71) Applicant: EnGeneIC Molecular Delivery Pty Ltd, Sydney (AU)

(72) Inventors: Himanshu Brahmbhatt, Sydney (AU); Jennifer MacDiarmid, Sydney (AU)

(73) Assignee: EnGeneIC Molecular Delivery Pty Ltd, Sydney (AU)

( * ) Notice: Subject to any disclaimer, the term of this patent is extended or adjusted under 35 U.S.C. 154(b) by 968 days.

(21) Appl. No.: 17/420,624

(22) PCT Filed: Jan. 6, 2020

(86) PCT No.: PCT/IB2020/050063
§ 371 (c)(1),
(2) Date: Jul. 2, 2021

(87) PCT Pub. No.: WO2020/141495
PCT Pub. Date: Jul. 9, 2020

(65) Prior Publication Data
US 2022/0105177 A1 Apr. 7, 2022

Related U.S. Application Data

(60) Provisional application No. 62/788,257, filed on Jan. 4, 2019.

(51) Int. Cl.
| | | |
|---|---|---|
| *A61K 39/39* | (2006.01) | |
| *A61K 31/337* | (2006.01) | |
| *A61K 31/519* | (2006.01) | |
| *A61K 31/5517* | (2006.01) | |
| *A61K 31/704* | (2006.01) | |
| *A61K 31/7105* | (2006.01) | |
| *A61K 38/07* | (2006.01) | |
| *A61K 38/12* | (2006.01) | |
| *A61K 39/00* | (2006.01) | |
| *A61P 35/00* | (2006.01) | |

(52) U.S. Cl.
CPC ............ *A61K 39/39* (2013.01); *A61K 31/337* (2013.01); *A61K 31/519* (2013.01); *A61K 31/5517* (2013.01); *A61K 31/704* (2013.01); *A61K 31/7105* (2013.01); *A61K 38/07* (2013.01); *A61K 38/12* (2013.01); *A61K 39/0011* (2013.01); *A61P 35/00* (2018.01); *A61K 2039/5154* (2013.01); *A61K 2039/55572* (2013.01); *A61K 2039/6006* (2013.01); *A61K 2039/6056* (2013.01)

(58) Field of Classification Search
None
See application file for complete search history.

(56) References Cited

U.S. PATENT DOCUMENTS

| | | |
|---|---|---|
| 7,183,105 B2 | 2/2007 | Sabbadini et al. |
| 8,591,862 B2 | 11/2013 | Brahmbhatt et al. |
| 8,591,963 B2 | 11/2013 | Mendoza |
| 8,691,963 B2 | 4/2014 | Brahmbhatt et al. |
| 8,772,013 B2 | 7/2014 | Brahmbhatt et al. |
| 2008/0038296 A1 | 2/2008 | Brahmbhatt et al. |
| 2008/0051469 A1 | 2/2008 | Brahmbhatt et al. |
| 2012/0207754 A1 | 8/2012 | Giacalone et al. |
| 2014/0255363 A1 | 9/2014 | Metelitsa et al. |
| 2015/0283235 A1 | 10/2015 | Hirai et al. |
| 2017/0165345 A1 | 6/2017 | Leadbetter et al. |
| 2017/0326235 A1 | 11/2017 | Brahmbhatt et al. |
| 2017/0368002 A1 | 12/2017 | Cerundolo et al. |
| 2018/0140665 A1 | 5/2018 | Giacalone |

FOREIGN PATENT DOCUMENTS

| | | |
|---|---|---|
| CN | 105658233 A | 6/2016 |
| WO | WO 2000/067776 | 11/2000 |
| WO | WO 2003/033519 A2 | 4/2003 |
| WO | WO 03/072014 A2 | 9/2003 |
| WO | WO 2004/113507 A1 | 12/2004 |
| WO | WO 2005/056749 A2 | 6/2005 |
| WO | WO 2005/079854 A1 | 9/2005 |
| WO | WO 2009/027830 A2 | 3/2009 |
| WO | WO-2013/079687 A1 | 6/2013 |
| WO | WO 2020/021437 A1 | 1/2020 |

OTHER PUBLICATIONS

International Preliminary Report on Patentability issued in International Patent Application No. PCT/IB2020/050063, dated Jul. 15, 2021.
King, et al., "CD1d-Invariant Natural Killer T Cell-Based Cancer Immunotherapy: α-Galactosylceramide and Beyond." *Frontiers in Immunology*, pp. 1-7, vol. 9, No. 1519 (Jul. 2018).
International Search Report issued in International Patent Application No. PCT/IB2020/050063, dated Apr. 24, 2020.
Office Action issued in Chinese Patent Application No. 2020800179617, dated Sep. 1, 2023.
Notice of Reasons for Refusal issued in co-pending Japanese Patent Application No. 2021-539364, dated Oct. 4, 2023.
Notice of Reasons for Refusal issued in co-pending Japanese Patent Application No. 2021-539364, dated Apr. 16, 2024.
Communication and Search Report issued in European Patent Application No. 20735988.6, dated Dec. 9, 2012.
Kanako, et al., "Human Leukemic Cells Loaded with a-galactosylceramide (a-GalCer) activate murine NKT cells in situ," *Intern. Journ. of Hematology*, vol. 92, No. 1, pp. 152-160 (Jun. 2010).

(Continued)

*Primary Examiner* — Jennifer E Graser
(74) *Attorney, Agent, or Firm* — Foley & Lardner LLP

(57) ABSTRACT

Compositions and methods for treating cancer are provided. In particular, the compositions comprise an encapsulated CD1d-restricted invariant Natural Killer T (iNKT) cell antigen, such as glycosphingolipid, for example, α-galactosylceramide. Methods of administering the compositions in combination with a therapy that induces the death of neoplastic cells in the subject are provided.

18 Claims, 29 Drawing Sheets

(56) References Cited

OTHER PUBLICATIONS

Birkholz, et al., "The Alpha and Omega of Galactosylceramides in T Cell Immune Function," *The Journ. Of Biological Chem.*, vol. 290, No. 25, pp. 15365-15370 (Jun. 2015).

Bredel, "Anticancer drug resistance in primary human brain tumors," brain Res. Rev., 35, pp. 161-204 (2001).

Brody et al., "In Situ Vaccination With a TLR9 Agonist Induces Systemic Lymphoma Regression: A Phase I/II Study," *J. Clin. Oncol.*, 28:4324-4332 (2010).

Bürckstümmer, et al., "An orthogonal proteomic-genomic screen identifies AIM2 as a cytoplasmic DNA sensor for the inflammasome," *Nat. Immunol.*, vol. 10, pp. 266-272 (2009).

Burger, et al., "Small peptide inhibitors of the CXCR4 chemokine receptor (CD184) antagonize the activation, migration, and antiapoptotic responses of CXCL12 in chronic lymphocytic leukemia B cells," *Blood*, vol. 106:1824-1830 (2005).

Carreno et al., "Synthetic Glycolipid Activators of Natural Killer T Cells as Immunotherapeutic Agents," *Clin Transl. Immunology*, 5(4): e69, 9 pages (2016).

Caskey, et al., "Synthetic double-stranded RNA induces innate immune responses similar to a live viral vaccine in humans," *J. Exp. Med.*, vol. 208, pp. 2357-2366 (2011).

Cauwels, et al., "Delivering Type I Interferon to Dendritic Cells Empowers Tumor Eradication and Immune Combination Treatments," *Cancer Research* 78, pp. 463-474 (2018).

Chatalic, et al., "Radiopeptides for imaging and therapy: a radiant future," J Nucl Med., vol. 56, pp. 1809-1812 (2015).

Chikuma et al., "Suppressors of cytokine signaling: Potential immune checkpoint molecules for cancer immunotherapy," *Cancer Sci.*, vol. 108, pp. 574-580 (2017).

Chiu et al., RNA Polymerase III Detects Cytosolic DNA and Induces Type-1 Interferons Through the RIG-I Pathway, *Cell*, vol. 138, pp. 576-591 (2009).

Colonna, et al., "Plasmacytold Dendritic Cells in Immunity," *Nature Immunology*, vol. 5, No. 12, pp. 1219-1226 (Dec. 2004).

Corrales, et al., "Direct Activation of STING in the Tumor Microenvironment Leads to Potent and Systemic Tumor Regression and Immunity," *Cell Reports*, vol. 11, pp. 1018-1030 (May 2015).

D'Aloia et al., "CAR-T Cells: The Long and Winding Road to Solid Tumors," *Cell death & disease* 9, 282 (2018), 12 pages.

D'Angiolella et al., "Cyclin F-Mediated Degradation of Ribonucleotide Reductase M2 Controls Genome Integrity and DNA Repair," Cell, 149:1023-34 (2012).

Deutscher, "Phage Display in Molecular Imaging and Diagnosis of Cancer," Chem Rev., vol. 110, pp. 3196-3211 (2010).

Dine et al., "Immune Checkpoint Inhibitors: An Innovation in Immunotherapy for the Treatment and Management of Patients with Cancer," *Asia-Pacific Journal of Oncology Nursing*, vol. 4, pp. 127-135 (2017).

Dobbs et al., "STING activation by translocation from the ER is associated with infection and autoinflammatory disease," Cell Host Microbe, 18(2): 15-24 (2015).

Dowling et al., "The Ultra-Potent and Selective TLR8 Agonist VTX-294 Activates Human Newborn and Adult Leukocytes," PLoS One, 8:e58164 (2013), 11 pages.

Dredge et al., "Adjuvants and the promotion of Th1-type cytokines in Tumour immunotherapy," Cancer immunology, immunotherapy: CII 51, pp. 521-531 (2002).

Dynavax Technologies Corporation. Study of SD-101 in Combination with Localized Low-dose Radiation in Patients with Untreated Low-grade B-cell Lymphoma. 2016. ClinicalTrials.gov [Internet]. Bethesda (MD): National Library of Medicine (US). Identifier: NCT02266147. Available from: https://ClinicalTrials.gov/show/NCT02266147. (Jul. 1, 2016).

Erathodiyil N, Ying JY. Functionalization of inorganic nanoparticles for bioimaging applications. Acc Chem Res., vol. 44, pp. 925-935 (2011).

Fang, et al., "NK cell-based immunotherapy for cancer," *Seminars in Immunology*, vol. 31, pp. 37-54 (2017).

Farkona, et al., "Cancer immunotherapy: the beginning of the end of cancer?," *BMC Medicine* 14, 73, 18 pages (2016).

Ferlazzo et al., "NK Cell Compartments and Their Activation by Dendritic Cells1," *The Journal of Immunology*, vol. 172, pp. 1333-1339 (2004).

Fernandes-Alnemri et al., "AIM2 activates the inflammasome and cell death in response to cytoplasmic DNA," Nature, vol. 458, pp. 509-513 (2009).

Field et al., "Inducers of Interferon and Host Resistance, II. Multistranded Synthetic Polynucleotide Comlexes," Proc. Natl Acad. Sci. USA, 58: pp. 1004-1010 (1967).

Fitzgerald-Bocarsly et al., "The role of type I Interferon Production by Dendritic Cells in Host Defense," *Biochimie* 89, pp. 843-855 (2007).

Allen, et al., "CCL3 augments tumor rejection and enhances CD8C T cell infiltration through NK and CD103C dendritic cell recruitment via IFNγ," *Oncommunology*, vol. 7, No. 3, e1393598 (11 pages).

Fu, et al., "STING agonist formulated cancer vaccines can cure established tumors resistant to PD-1 blockade," *Sci Transl. Med.*, vol. 7, pp. 283, 24 pages (Apr. 2015).

Fukuda, "Chemical labeling of carbohydrates by oxidation and sodium borohydride reduction," Curr Protoc. Mol. Biol., pp. 17.5.1-17.5.8: Supplement 26 (1994).

Gao et al., "Cyclic [G(2',5')pA(3',5')p] is the Metazoan Second Messenger Produced by DNA-Activated Cyclic GMP-AMP Synthase," *Cell*, 153:1094-1107 (2013).

Gao et al., "Cyclic GMP-AMP Synthase is an Innate Immune Sensor of HIV and Other Retroviruses," *Science*, vol. 341: pp. 903-906 (2013).

Gao et al., "In vivo Cancer Targeting and Imaging with Semiconductor Quantum Dots," *Nat Biotechnol.*, 22(8): pp. 969-976 (2004).

Gerard SK, Cavalieri RR. I-123 diagnostic thyroid tumor wholebody scanning with imaging at 6, 24, and 48 hours. Clin Nucl Med. 2002;27(1):1-8.

Ghosh A, Heston WDW. Tumor target prostate specific membrane antigen (PSMA) and its regulation in prostate cancer. *J Cell Biochem.* 2004;91(3):528-539.

Gitlin et al., "Essential role of mda-5 in type I IFN responses to polyriboinosinic:polyribocytidylic acid and encephalomyocarditis picornavirus," *Proc. Natl Acad. Sci. USA*, 103: pp. 8459-8464 (2006).

Gray, et al., "Combinatorial Peptide Libraries: Mining for Cell-Binding Peptides," *Chem. Rev.*, vol. 114, No. 2 pp. 1020-1081 (Jan. 2014).

Hobbs et al., "Regulation of Transport Pathways in Tumor Vessels: Role of Tumor Type and Microenvironment," *Proc. Natl. Acad. Sci. USA*, 95(8): pp. 4607-4612 (1998).

Holman, et al., "Single-photon emission computed tomography (SPECT): applications and potential," JAMA, vol. 263, No. 4, pp. 561-564 (1990).

Hornung et al., "AIM2 Recognizes Cytosolic dsDNA and forms a Caspase-1 Activating Inflammasome with ASC," *Nature*, 458, pp. 514-518 (2009).

Igarashi, et al., "Vasoactive intestinal peptide (VIP) and VIP receptors—elucidation of structure and function for therapeutic applications," Int J Clin Med., vol. 2, pp. 500-508 (2011).

Jenkins et al., "Mechanisms of Resistance to Immune Checkpoint Inhibitors," *British Journal of Cancer*, vol. 118, pp. 9-16 (2018).

Jung et al., "Dendritic Cell-Based Immunotherapy for Solid Tumors," *Translational oncology* 11, pp. 686-690 (2018).

Kao et al., "A Significant Metabolic and Radiological Response after a Novel Targeted MicroRNA-based Treatment Approach in Malignant Pleural Mesothelioma," *Am. J. Respir. Crit. Care Med.*, 191(12): pp. 1467-1469 (2015).

Kawai, et al., "The role of pattern-recognition receptors in innate immunity: update on Toll-like Receptors," *Nat. Immunol.*, 11, pp. 373-384 (2010).

Kim, et al., "Aspartate-glutamate-alanine-histidine box motif (DEAH)/RNA helicase A helicases sense microbial DNA in human plasmacytoid dendritic cells," PNAS, vol. 107, No. 34, pp. 15181-15186 (Aug. 2010).

(56) References Cited

OTHER PUBLICATIONS

Kramer-Marek G, et al., "The role of nuclear medicine in modern therapy of cancer," Tumour Biol. 2012;33(3), pp. 629-640.
Kranzusch et al., "Structure of human cGAS reveals a conserved family of second-messenger enzymes in innate immunity," Cell Rep., vol. 3, pp. 1362-1368 (2013).
Krieg et al., "CpG Motifs in Bacterial DNA Trigger Direct B-cell Activation," Nature, vol. 374, pp. 546-549 (1995).
Kwekkeboom et al., "Treatment with the radiolabeled somatostatin analog [$^{177}$Lu-DOTA$^0$, Tyr$^3$] Octreotate: Toxicity, Efficacy, and Survival," J Clin Oncol., vol. 26, No. 13, pp. 2124-2130 (May 2008).
Landskron et al., "Chronic Inflammation and Cytokines in the Tumor Microenvironment," Journal of Immunology Research 2014, 149185, 20 pages (2014).
Lee et al., "Cytokines in Cancer Immunotherapy," Cancers 3, pp. 3856-3893 (2011).
Leung, et al., "When your cap matters: Structural insights into self vs non-self-recognition of 5' RNA by immunomodulatory host proteins,", Curr. Opin. Struct. Biol., vol. 36 (2016), 30 pages.
Li et al., "Pivotal Roles of cGAS-cGAMP Signaling in Antiviral Defense and Immune Adjuvant Effects," Science, 341, pp. 1390-1394 (2013).
Hansen, et al., "Listeria monocytogenes induces IFNβ Expression through an IFI16-, CGAS- and STING-dependent Pathway," Embo J., 33(15): 1654-66 (2014).
Liu et al., "Phosphorylation of innate immune adaptor proteins MAVS, STING, and TRIF induces IRF3 Activation," Science, vol. 347, 17 pages (2015).
Lu et al., "The Structural Basis of 50 Triphosphate Double-Stranded RNA Recognition by Rig-I C-Terminal Domain," Structure, vol. 18 , pp. 1032-1043 (2010).
Ma et al., "Positioning of the MinE binding site on the MinD surface suggests a plausible mechanism for activation of the Escherichia coli MinD ATPase during division site Selecti," Mol. Microbiol., 54, pp. 99-108 (2004).
MacDiarmid et al., "Targeted Doxorubicin Delivery to Brain Tumors viaMinicells: Proof of Principle Using Dogs with Spontaneously Occurring Tumors as a Model," PLoS One, 11(4), 13 pages (2016).
Majkowska et al., "Complexes of low energy beta emitters $^{47}$Sc and $^{177}$Lu with zoledronic acid for bone pain therapy," Appl. Radiat. Isot., vol. 67, No. 1, pp. 11-13 (2009).
McWhirter et al., "A Host Type I Interferon Response is Induced by Cytosolic Sensing of the Bacterial Second Messenger Cyclic-di-GMP,"J. Exp. Med., vol. 206, pp. 1899-1911 (2009).
Mellman et al., "Cancer Immunotherapy Comes of Age," Nature, vol. 480, pp. 480-489 (2011).
Morvan et al., "NK cells and cancer: you can teach innate cells new tricks," Nature reviews Cancer 16, pp. 7-19 (2016).
Muller, et al., "A Unique Matched Quadruplet of Terbium Radioisotopes for PET and SPECT and for a- and b2-Radionuclide Therapy: An In Vivo Proof-of-Concept Study with a New Receptor-Targeted Folate Derivative," Matched Terbium Radionuclide Quadruplet, J. Nucl. Med., vol. 53, No. 12, pp. 1951-1959 (2012).
Oiseth et al., "Cancer immunotherapy: a brief review of the history, possibilities, and challenges ahead," Journal of Cancer Metastasis and Treatment 3, 250-261 (2017).
Orzalli et al., "Nuclear IFI16 induction of IRF-3 signaling during herpesviral infection and degradation of IFI16 by the viral ICP0 protein," Proc. Natl. Acad. Sci., vol. 109, pp. pp. E3008-E3017 (2012).
Reid et al., "Restoring expression of miR-16: a novel approach to therapy for malignant pleural mesothelioma," Annals of Oncology, Official Journal of the European Society for Medical Oncology, vol. 24, pp. 3128-3135 (2013).
Rezvani et al., "Engineering Natural Killer Cells for Cancer Immunotherapy," Molecular therapy: the Journ. of the American Society of Gene Therapy, vol. 25, pp. 1769-1781 (2017).
Sawa-Wejksza et al., "Tumor-Associated Macrophages as Target for Antitumor Therapy," Arch. Immunol. Ther. Exp., vol. 66, pp. 97-111 (2018).
Schoggins et al., "Pan-viral specificity of IFN-induced genes reveals new roles for cGAS in innate immunity," Nature, vol. 505, pp. 691-695 (2014).
Sharpe, "Introduction to Checkpoint Inhibitors and Cancer Immunotherapy," Immunological reviews vol. 276, pp. 5-8 (2017).
Silver, et al., "Prostate-specific membrane antigen expression in normal and malignant human tissues," Clin Cancer Res., vol. 3, pp. 81-85 (1997).
Staudacher, et al., "Antibody drug conjugates and bystander killing: is antigen-dependent internalisation required?," British Journ. of Cancer, vol. 117, pp. 1736-1742 (2017).
Unterholzner et al., "IFI16 is an Innate Immune Sensor for Intracellular DNA," Nat. Immunol., vol. 11, pp. 997-1004 (2010).
Walrand, et al., "The impact of image reconstruction bias on PET/CT $^{90}$Y dosimetry after radioembolization," J Nucl Med., vol. 56(3):pp. 494-495 (2015).
Wang, et al., "Structural and functional insights into pattern recognition by the innate immune receptor RIG-1," Nat. Struct. Mol. Biol., vol. 17, No. 7, pp. 781-787 (2010).
White, et al., "Suppression of apoptosis: role in cell growth and neoplasia," Leukemia, 15: pp. 1011-1021 (2001).
Whittle, et al., "First in human nanotechnology doxorubicin delivery system to target epidermal growth factor receptors in recurrent glioblastoma," Journ. of Clinical Neuroscience, vol. 22, pp. 1889-1894 (2015).
Wu, et al., "Cyclic-GMP-AMP Is an Endogenous Second Messenger in Innate Immune Signaling by Cytosolic DNA," Science, vol. 339, pp. 826-830 (2013).
Xia et al., "Sox2 functions as a sequence-specific DNA sensor in neutrophils to initiate innate immunity against microbial infection," Nat. Immunol., 16, pp. 366-375 (2015).
Yi et al., Single Nucleotide Polymorphisms of Human STING Can Affect Innate Immune Response to Cyclic Dinucleotides PLoS One, 8(10) :e77846 (2013), 16 pages.
Zhang et al., "Cutting Edge: Ku70 Is a Novel Cytosolic DNA Sensor That Induces Type III Rather Than Type I IFN," J. Immunol., 186:4541-4545 (2011a).
Zhang et al., "The helicase DDX41 senses intracellular DNA mediated by the adaptor STING in dendritic cells," Nat. Immunol., 12, pp. 959-965 (2011b).
Zitvogel et al., "Type I IFNs and Anticancer Therapies," Nature reviews Immunology 15, pp. 405-414 (2015).
Ahmadzadehfar et al., "Radioembolization of liver tumors with yttrium-90 microspheres," Semin Nucl Med. 2010;40(2):105-121.
Ablasser et al., "RIG-I Dependent Sensing of Poly9dA-dT) via the Induction of an RNA Polymerase III Transcribed RNA Intermediate," Nat. Immunol., 10 (10):1065-72 (2009).
Ablasser et al., "Cell Intrinsic Immunity Spreads to Bystander Cells via the Intercellular Transfer of cGAMP," Nature, 503:530-534 (2013).
Adamus et al., "The Revival of CpG Oligonucleotide-based Cancer Immunotherapies," Contemp. Oncol (Ponzn), 22(1A):56-60 (Mar. 2018).
Ahmadzadehfar et al., "Therapeutic response and side effects of repeated radioligand therapy with 177Lu-PSMA-DKFZ-617 of castrate-resistant metastatic prostate cancer," Oncotarget. 2016;7(11):12477-12488.
Alexopoulou et al., "Recognition of Double-Stranted RNA and Activation of NF-kappaB by Toll-like Receptor 3," Nature, 413: 732-738 (2001).
Anguille et al., "Dendritic Cells as Pharmacological Tools for Cancer Immunotherapy," Pharmacological Reviews 67, 731-753 (2015).
Barber et al., "Innate Immune DNA Sensing Pathways: STING, AIMII and the Regulation of Interferon Production and Inflammatory Responses," Curr. Opin. Immunol., 23(1): 10-20 (2011).
Bernardini et al., Dysregulation of Chemokine/Chemokine Receptor Axes and NK Cell Tissue Localization during Diseases, Frontiers in immunology 7, 402, 9 pages (2016).

(56) References Cited

OTHER PUBLICATIONS

Ablasser, et al., "cGAS Produces a 2'-5' -linked cyclic dinucleotide second messenger that activates STING," *Nature*, vol. 498, No. 7454, pp. 380-384 (2013).
Aduro Biotech Inc., Novartis Pharmaceuticals, *Study of the Safety and Efficacy of MIW815 (ADU-S100) in Patients with Advanced/ Metastatic Solid Tumors or Lymphomas*. ClinicalTrials.gov [Internet]. Identifier: NCT02675439. Available from: https://ClinicalTrials.gov/show/NCT02675439 (Jul. 1, 2016).
Alzahrani, et al.,"Diagnostic value of recombinant human thyrotropin-stimulated 123I whole-body scintigraphy in the follow-up of patients with differentialed thyroid cancer," *Clin Nucl Med.* 2012;37(3):229-234.
Andersson, et al., "Large-scale synthesis of peptides," *Biopolymers*. vol. 55, pp. 227-250 (2000).
Belardelli et al., "Cytokines as a Link between Innate and Adaptive Antitumor Immunity," *Trends in Immunology*, vol. 23, pp. 201-208 (2002).
Britton, et al., "Characterization of a prokaryotic SMC protein involved in chromosome partitioning," *Genes & Development*, pp. 1254-1259 (1998).
Caplen, "RNAi as Gene Therapy Approach," *Gene Therapy*, pp. 575-586 (2003).
Caplen, et al., "Short Interfering RNA (siRNA)—Mediated RNA Interference (RNAi) in Human Cells," *Ann. N.Y. Acad. Sci.*, pp. 56-62 (2003).
Caravella, et al., "Design of next-generation protein therapeutics," *Curr. Opin. Chem. Biol.*, vol. 14, No. 4, (Aug. 2010).[Abstract].
Chen et al., "Reversal—of Drug Resistance Mediated By Multidrug Resistance Protein (MRP) 1 By Dual Effects of Agosterol A on MRP1 Function", Int. J. Cancer: 93, pp. 107-113 (2001).
Chu et al., "Translation Repression in Human Cells by MicroRNA-Induced Gene Silencing Requires RCK/p54," *PLOS Biology*, vol. 4, No. 7, pp. 1122-1136 (Jul. 2006).
Civril et al., "Structural mechanism of cytosolic DNA sensing by cGAS," vol. 498, pp. 332-337 (2013).
Clark-Curtiss and Curtiss, "Analysis of Recombinant DNA Using *Escherichia coli* Minicells," Methods Enzymol., 101: 347-362 (1983).
Cory, et al., "Use of an aqueous soluble tetrazolium/formazan assay for cell growth assays in culture," Cancer Commun., vol. 3, No. 7, pp. 207-212 (1991).
DaSilva, et al., "HER3 and downstream pathways are involved in colonization of Brain Metastases from Breast Cancer," *Breast Cancer Research*, vol. 12, R46, pp. 1-13 (2010).
De Boer et al., "Roles of MinC and MinD in the Site-Specific Septation Block Mediated by the MinCDE System of *Escherichia coli*," vol. 174, No. 1, pp. 63-70 (Jan. 1992).
Debinski, et al., "Expression of a Restrictive Receptor for Interleukin 13 is Associated with Glial Transformation," *J. Neurooncol.*, vol. 48, No. 2, pp. 103-111 (Jun. 2000)[Abstract].
Debinski, et al., "Molecular Expression Analysis of Restrictive Receptor for Interleukin 13, a Brain Tumor-associated Cancer/Testis Antigen," *Mol. Med.*, 6: 440-449 (2000).
Dong et al., "CD86+ /CD206+, Diametrically Polarized Tumor-Associated Macrophages, Predict Hepatocellular Carcinoma Patient Prognosis," International journal of molecular sciences 17, 320 (2016), 12 pages.
Duan, et al., "Inhibition of ABCB1 (MDR1) and ABCB4 (MDR3) Expression by Small Interfering RNA and Reversal of Paclitaxel Resistance in Human Ovarian Cancer Cells," *Molecular Cancer Therapies*, vol. 3, No. 7, pp. 833-838 (Jul. 2004).
Duxbury, et al., "Systemic siRNA-Mediated Gene Silencing A New Approach to Targeted Therapy of Cancer," *Annals. Of Surgery*, vol. 240, No. 4, pp. 667-674 (Oct. 2004).
Emens et al., "Cancer immunotherapy: Opportunities and challenges in the rapidly evolving clinical landscape," European Journal of Cancer 81, pp. 116-129 (2017).
Goh, et al., "Endocytosis of Receptor Tyrosine Kinases," *Harb. Perspect., Biol.*, 5: a017459, 17 pages (2013).
Gregory, et al., Methods in Molecular Biology, vol. 342, pp. 33-47 ( pril 2006).[Abstract].
Harry, "Bacterial Cell Divisional: Regulating Z-ring formation," *Molecular Microbiology*, vol. 40, No. 4, pp. 795-803 (2001).
Hershey, "IL-13 Receptors and Signaling Pathways: an Evolving web," *J. Allergy Clin. Immunol.*, vol. 111, No. 4, pp. 677-690 (2003).
Hiraga, et al., "Chromosome Partitioning in *Escherichia coli*: Novel Mutants Producing Anucleate Cells," *Journ. of Bacteriology*, pp. 1496-1505 (Mar. 1989).
Hu et al., "Topological Regulation of Cell Divisional in *Escherichia coli* involves rapid pole to pole oscillation of the divisional inhibitor MinC under the control of MinD and MinE," *Molecular Microbiologyi*, vol. 34, No. 1, 82-90 (1999).
Iftode, el al, "Replication Protein A (RPA): the Eukaryotic SSB," *Crit Rev. Biochem. Mol. Biol.*, vol. 34, No. 3, pp. 141-180 (1999)[Abstract].
Jarboe, et al., Expression of Interleukin-13 Receptor $\alpha 2$ in Glioblastoma Multiforme: Implications for Targeted Therapies, *Cancer Res.*, vol. 67, pp. 7983-7986 (2007).
Khalil, et al., "Many Human Large Intergenic Noncoding RNAs Associate with chromatin-modifying complexes and affect gene expression," *PNAS*, vol. 106, No. 28, pp. 11667-11672 (Jul. 2009).
Kota et al., "Therapeutic Delivery of miR-26a Inhibits Cancer Cell Proliferation and Induces Tumor-Specific Apoptosis," *Cell*, 137: 1005-1017 (2009).
Lemmon, et al., "Cell Signaling by Receptor-Tyrosine Kinases," *Cell*, vol. 141, No. 7, pp. 1117-1134 (Jun. 2010).
MacDiarmid, et al., "Bacterially Derived 400 nm Particles for Encapsulation and Cancer Cell Targeting of Chemotherapeutics," *Cancer Cell*, No. 11. pp. 431-445 (May 2007).
MacDiarmid, et al., "Bacterially-Derived Nanocells for Tumor-Targeted Delivery of Chemotherapeutics and Cell Cycle Inhibitors," *Cell Cycle*, pp. 2099-2105 (2007).
MacDiarmid, et al., "Sequential Treatment of Drug-Resistant Tumors with Targeted Minicells containing SiRNA or a Cytoloxic Drug," *Nature Biotechnology*, vol. 27, No. 7, pp. 643-651 (2009).
Nieth, et al., Modulation of the Classical Multidrug Resistance (MDR) Phenotype by RNA Interference (RNAi), *FEBS Letters*, vol. 545, pp. 144-150 (2003).
Oh, et al., siRNA Delivery Systems for Cancer Treatment, *Advanced Drug Delivery Rev.*, 61: 850-62 (2009).
Okada, et al., "Cytoplasmic Axial Filaments in *Escherichia coli* Cells: Possible Function in the Mechanism of Chromosome Segregation and Cell Division," *Journ. of Bacteriology*, pp. 917-922 (Feb. 1994).
Quintieri, et al., "Formation and Antitumor Activity of PNU-159682, A Major Metabolite of Nemorubicin in Human Liver Microsomes," *American Associate of Cancer Research*, vol. 11, pp. 1608-1617 (Feb. 2005).
Raskin, et al., "MinDE-Dependent Pole-to-Pole Oscillation of Division Inhibitor MinC in *Escherichia coli*," *Journ. of Bacteriology*, pp. 6419-6424 (Oct. 1999).
Reeve, et al., "bacteriophage SPO1-Induced Macromolecular Synthesis in Minicells of bacillus subtilis," *Journal of Virology*, pp. 1308-1316 (Jun. 1975).
Rice, et al., "The Next Generation of Positron Emission Tomography Radiopharmaceuticals in Oncology." *Semin. Nucl. Med.*, vol. 41, No. 4, pp. 265-282 (2011).
Sioud, "Therapeutic siRNAs," *Trends in Pharm. Sciences*, vol. 25, No. 1, pp. 22-28 (Jan. 2004).
Stewart, et al., "Genetic and Morphological Characterization of an *Escherichia coli* Chromosome Segregation Mutant," *Journ. of Bact.*, pp. 4513-4516 (Jul. 1992).
Tanpure, et al., "Synthesis of Structurally Diverse Benzosuberene Analogues and their Biological Evaluation as Anti-Cancer Agents," *Bioorg. Med. Chem.*, vol. 21, No. 24, pp. 8019-8032 (Dec. 2013).
Wykosky et al., "Interleukin-13 Receptor $\alpha 2$, EphA2, and Fos-Related Antigen 1 as Molecular Denominalors of High-Grade Astrocytomas and Specific Targets for Combinatorial Therapy," *Clin Cancer Res.*, 14: 199-208 (2008).

(56) References Cited

OTHER PUBLICATIONS

Yague et al., "Complete reversal of multidrug resistance by stable expression of small interfering RNAs targeting MDR1," Gene Ther., 11, pp. 1170-1174 (2004).

Yang et al., "TMTP1 A Novel tumor-homing peptide specifically targeting metastasis," Clin Cancer Res., vol. 14, pp. 5494-5502 (2008).

Yang et al., "The cytosolic nucleic acid sensor LRRFIP1 mediates the production of type I interferon via a β-catenin-dependent pathway," *Nat. Immunol.*, vol. 11, pp. 487-494 (2010).

Yuan et al., "Opposite Effects of M1 and M2 Macrophage Subtypes on Lung Cancer Progression," Scientific reports 5, 14273 (2015).

Zibert et al., CCL3/MIP-1α Is a Potent Immunostimulator When Coexpressed with Interleukin-2 or Granulocyte-Macrophage Colony-Stimulating Factor in a Leukemia/Lymphoma Vaccine Human Gene Therapy 15, pp. 21-34 (2004).

Ziegler-Heitbrock et al., "Toward a Refined Definition of Monocyte Subsets," Frontiers in Immunology 4, vol. 23, 5 pages (2013).

minicell$_{\alpha\text{-GC}}$ (1x10$_6$)

$Ep$minicell$_{box}$ (1x10$^9$)

$_{Ep}$minicell$_{Dox}$ (1x10$_9$) + minicell$_{\alpha\text{-}GC}$ (1x10$_7$); 16hr $_{Ep}$minicell$_{Dox}$ (1x10$_9$) + minicell$_{\alpha\text{-}GC}$ (1x10$_7$); 24hr

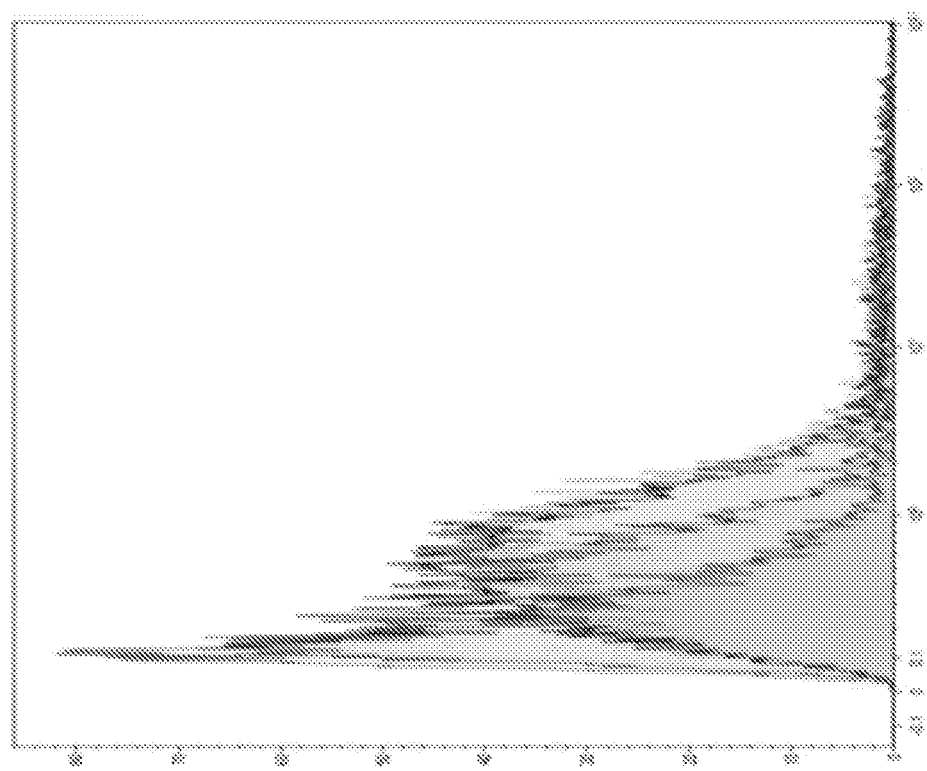
Figure 8A

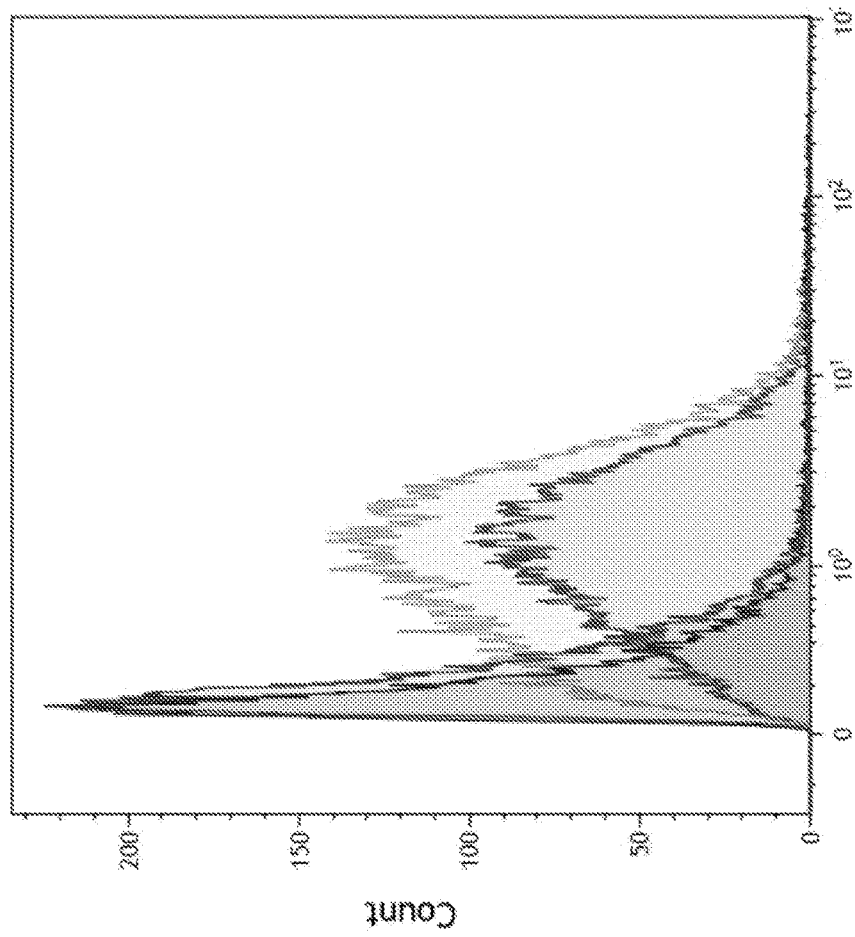
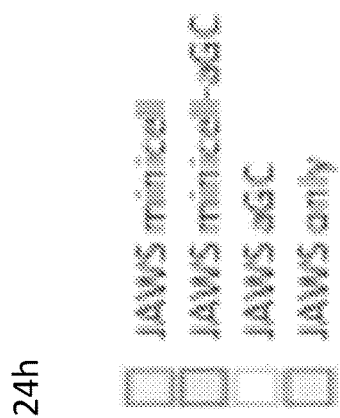
Figure 8C

ENCAPSULATED GLYCOLIPID ANTIGENS FOR TREATMENT OF NEOPLASTIC DISEASES

RELATED APPLICATION

This application is the U.S. National Stage of International Patent Application No. PCT/IB2020/050063, filed Jan. 6, 2020, which claims priority from U.S. Provisional Patent Application No. 62/788,257, filed Jan. 4, 2019. The entire contents of these applications are incorporated herein by reference in their entirety.

BACKGROUND

Effective immunotherapy strategies for the treatment of diseases such as cancer depend on the activation of both innate and adaptive immune responses. Cells of the innate immune system interact with pathogens via conserved pattern-recognition receptors, whereas cells of the adaptive immune system recognize pathogens through diverse, antigen-specific receptors that are generated by somatic DNA rearrangement. Invariant natural killer T (iNKT) cells are a subset of lymphocytes (Type I NKT) that bridge the innate and adaptive immune systems. iNKT cells express an invariant a chain T cell receptor (V$\alpha$24-J$\alpha$18 in humans and V$\alpha$14-J$\alpha$18 in mice) that is specifically activated by certain glycolipids presented in the context of the non-polymorphic MHC class I-like protein, CD1d. CD1d binds to a variety of dialkyl lipids and glycolipids, such as the glycosphingolipid $\alpha$-galactosylceramide ($\alpha$-GalCer). iNKT cell TCR recognition of the CD1d-lipid complex results in the release of pro-inflammatory and regulatory cytokines, including the Th1 cytokine interferon gamma (IFN$\gamma$). The release of cytokines in turn activates adaptive cells, such as T and B cells, and innate cells, such as dendritic cells and NK cells.

$\alpha$-GalCer, also known as KRN7000, chemical formula $C_{50}H_{99}NO_9$, is a synthetic glycolipid derived from structure-activity relationship studies of galactosylceramides isolated from the marine sponge *Agelas mauritianus*. $\alpha$-GalCer is a strong immunostimulant and shows potent anti-tumor activity in many in vivo models A major challenge to using $\alpha$-GalCer for immunotherapy is that it induces anergy in iNKT cells because it can be presented by other CD1d expressing cells, such as B cells, in the peripheral blood. Delivery of $\alpha$-GalCer also has been shown to induce liver toxicity.

Accordingly, new compositions and methods are needed for delivery of $\alpha$-GalCer to phagocytic cells and inducing an effective immune response against tumor cells. The present invention satisfies these needs.

SUMMARY OF THE INVENTION

Described herein, in certain embodiments, are adjuvant compositions comprising an immunogenically effective amount of intact, bacterially derived minicells or killed bacterial cells that encapsulate a CD1d-restricted invariant Natural Killer T (iNKT) cell antigen. In some embodiments, the encapsulated CD1d-restricted iNKT cell antigen is capable of uptake by a phagocytic cell, such as a dendritic cell or a macrophage. Following uptake, the CD1d-restricted iNKT cell antigen form complexes with CD1d within the lysosomes of the phagocytic cells and is subsequently transported to the surface of the phagocytic cells where the CD1d-restricted iNKT cell antigen bound to CD1d is presented for recognition by an iNKT cell. In some embodiments, the CD1d-restricted iNKT cell antigen induces a Th1 cytokine response by an iNKT cell that recognizes the CD1d-restricted iNKT cell antigen bound to CD1d on the surface of the phagocytic cell.

In some embodiments, the CD1d-restricted iNKT cell antigen is a glycosphingolipid. In some embodiments, the glycosphingolipid is selected from among $\alpha$-galactosylceramide ($\alpha$-GalCer), C-glycosidific form of $\alpha$-galactosylceramide ($\alpha$-C-GalCer), 12 carbon acyl form of galactosylceramide ($\beta$-GalCer), $\beta$-D-glucopyranosylceramide ($\beta$-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), $\alpha$-glucuronosylceramide (GSL-1 or GSL-4), isoglobotrihexosylceramide (iGb3), lipophosphoglycan (LPG), lyosphosphatidylcholine (LPC), $\alpha$-galactosylceramide analog (OCH), threitolceramide, and a derivative of any thereof. In some embodiments, the glycosphingolipid is $\alpha$-GalCer. In some embodiments, the glycosphingolipid is a synthetic $\alpha$-GalCer analog. In some embodiments, the synthetic $\alpha$-GalCer analog is selected from among 6'-deoxy-6'-acetamide $\alpha$-GalCer (PBS57), napthylurea $\alpha$-GalCer (NU-$\alpha$-GC), NC-$\alpha$-GalCer, 4ClPhC-$\alpha$-GalCer, PyrC-$\alpha$-GalCer, $\alpha$-carba-GalCer, carba-$\alpha$-D-galactose $\alpha$-GalCer analog (RCAI-56), 1-deoxy-neo-inositol $\alpha$-GalCer analog (RCAI-59), 1-O-methylated $\alpha$-GalCer analog (RCAI-92), and HS44 aminocyclitol ceramide. In some embodiments, the CD1d-restricted iNKT cell antigen is derived from a bacterial antigen, a fungal antigen, or a protozoan antigen.

In one embodiment, the adjuvant composition comprises (a) an immunogenically effective amount of an encapsulated CD1d-restricted invariant Natural Killer T (iNKT) cell antigen and (b) a therapeutically effective dose of an antineoplastic agent.

In one embodiment, the CD1d-restricted iNKT cell antigen and the antineoplastic agent are packaged within two or more intact bacterially derived minicells or killed bacterial cells. In one embodiment, the adjuvant composition comprises the CD1d-restricted iNKT cell antigen and the antineoplastic agent, wherein: (a) the CD1d-restricted iNKT cell antigen and the antineoplastic agent are comprised within the same intact bacterially-derived minicell or killed bacterial cell; or (b) the CD1d-restricted iNKT cell antigen is comprised within a first intact bacterially-derived minicell or killed bacterial cell, and the antineoplastic agent is comprised within a second intact bacterially-derived minicell or killed bacterial cell.

In some embodiments, the intact bacterially-derived minicell comprising the antineoplastic agent comprises at least one targeting agent. In some embodiments, the intact bacterially-derived minicell comprising the CD1d-restricted iNKT cell antigen does not comprise a targeting agent, and the intact bacterially-derived minicell comprising the antineoplastic agent comprises a targeting agent. In some embodiments, the targeting agent is a bispecific ligand. In some embodiments, the bispecific ligand comprises a first arm that carries specificity for a minicell surface structure and a second arm that carries specificity for a non-phagocytic mammalian cell surface receptor. In some embodiments, the mammalian cell surface receptor is the Epidermal Growth Factor receptor (EGFR). In some embodiments, the minicell surface structure is an O-polysaccharide component of a lipopolysaccharide on the minicell surface. In some embodiments, the non-phagocytic mammalian cell surface receptor is capable of activating macropinocytosis or receptor-mediated endocytosis of the minicell. In some embodiments, the bispecific ligand comprises a bispecific antibody or antibody fragment. In some embodiments, the antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating macropinocytosis or receptor-mediated endocytosis of the minicell. In some embodiments, the second multivalent arm carries specificity for EGFR.

Described herein, in certain embodiments, are methods for treating a neoplastic disease, comprising administering to a subject in need thereof (a) an immunogenically effective amount of an encapsulated CD1d-restricted invariant Natural Killer T (iNKT) cell antigen and (b) an antineoplastic agent or therapy that induces the death of neoplastic cells in the subject. In some embodiments, the therapy that induces the death of neoplastic cells comprises administration of an antineoplastic agent.

In some embodiments of the methods and compositions described herein, the encapsulated CD1d-restricted iNKT cell antigen is capable of uptake by a phagocytic cell, such as a dendritic cell or a macrophage. In some embodiments, the CD1d-restricted iNKT cell antigen induces a Th1 cytokine response by an iNKT cell that recognizes the antigen presented by CD1d. In some embodiments, the CD1d-restricted iNKT cell antigen is a glycosphingolipid. In some embodiments, the glycosphingolipid is selected from among α-galactosylceramide (α-GalCer), C-glycosidific form of α-galactosylceramide (α-C-GalCer), 12 carbon acyl form of galactosylceramide (β-GalCer), β-D-glucopyranosylceramide (β-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan (LPG), lyosphosphatidylcholine (LPC), α-galactosylceramide analog (OCH), threitolceramide, and a derivative of any thereof. In some embodiments, the glycosphingolipid is α-GalCer. In some embodiments, the glycosphingolipid is a synthetic α-GalCer analog. In some embodiments, the synthetic α-GalCer analog is selected from among 6'-deoxy-6'-acetamide α-GalCer (PBS57), naphthylurea α-GalCer (NU-α-GC), NC-α-GalCer, 4ClPhC-α-GalCer, PyrC-α-GalCer, α-carba-GalCer, carba-α-D-galactose α-GalCer analog (RCAI-56), 1-deoxy-neo-inositol α-GalCer analog (RCAI-59), 1-O-methylated α-GalCer analog (RCAI-92), and HS44 aminocyclitol ceramide. In some embodiments, the CD1d-restricted iNKT cell antigen is derived from a bacterial antigen, a fungal antigen, or a protozoan antigen.

In some embodiments of the compositions and methods described herein, the antineoplastic agent is selected from the group consisting of a radionuclide, a chemotherapy drug, a functional nucleic acid, and a polynucleotide from which a functional nucleic acid can be transcribed. In some embodiments, the chemotherapeutic drug is a cytotoxin. In some embodiments, the chemotherapeutic drug is selected from the group consisting of morpholinyl anthracycline, a maytansinoid, duocarmycin, auristatins, calicheamicins (DNA damaging agents), α-amanitin (RNA polymerase II inhibitor), centanamycin, pyrrolobenzodiazepine, streptonigtin, nitrogen mustards, nitrosorueas, alkane sulfonates, pyrimidine analogs, purine analogs, antimetabolites, folate analogs, anthracyclines, taxanes, vinca alkaloids, topoisomerase inhibitors, hormonal agents, and a combination thereof. In some embodiments, the morpholinyl anthracycline is selected from the group consisting of nemorubicin, PNU-159682, idarubicin, daunorubicin, caminomycin, and doxorubicin. In some embodiments, the functional nucleic acid is selected from the group consisting of a siRNA, a miRNA, a shRNA, a lincRNA, an antisense RNA, and a ribozyme. In some embodiments, the functional nucleic acid inhibits a gene that promotes tumor cell proliferation, angiogenesis or resistance to chemotherapy and/or that inhibits apoptosis or cell cycle arrest. In some embodiments, the therapy that induces the death of neoplastic cells comprises radiation therapy or surgery.

In one embodiment, the methods comprise administering an adjuvant composition that comprises (a) an immunogenically effective amount of intact, bacterially derived minicells or killed bacterial cells that encapsulate CD1d-restricted iNKT cell antigen and (b) a therapeutically effective dose of an antineoplastic agent. In one embodiment, the CD1d-restricted iNKT cell antigen and the antineoplastic agent are packaged within two or more purified, intact bacterially derived minicells or killed bacterial cells. In one embodiment, the adjuvant composition comprises the CD1d-restricted iNKT cell antigen and the antineoplastic agent, wherein: (a) the CD1d-restricted iNKT cell antigen and the antineoplastic agent are comprised within the same minicell or killed bacterial cell or (b) the CD1d-restricted iNKT cell antigen is comprised within a first minicell or killed bacterial cell, and the antineoplastic agent is comprised within a second minicell or killed bacterial cell. In some embodiments, the intact bacterially-derived minicell comprising the antineoplastic agent comprises a targeting agent. In some embodiments, the intact bacterially-derived minicell comprising the CD1d-restricted iNKT cell antigen does not comprise a targeting agent, and the intact bacterially-derived minicell comprising the antineoplastic agent comprises a targeting agent. In some embodiments, the targeting agent is a bispecific ligand. In some embodiments, the bispecific ligand comprises a first arm that carries specificity for a minicell surface structure and a second arm that carries specificity for a non-phagocytotic mammalian cell surface receptor. In some embodiments, the mammalian cell surface receptor is the Epidermal Growth Factor receptor (EGFR). In some embodiments, the minicell surface structure is an O-polysaccharide component of a lipopolysaccharide on the minicell surface. In some embodiments, the non-phagocytotic mammalian cell surface receptor is capable of activating macropinocytosis or receptor-mediated endocytosis of the minicell. In some embodiments, the bispecific ligand comprises a bispecific antibody or antibody fragment. In some embodiments, the antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating macropinocytosis or receptor-mediated endocytosis of the minicell. In some embodiments the cell surface receptor is EGFR.

In some embodiments, the encapsulated CD1d-restricted iNKT cell antigen (e.g., α-GalCer) and the therapy that induces the death of neoplastic cells (e.g., antineoplastic agent) are administered simultaneously. In some embodiments, the encapsulated CD1d-restricted iNKT cell antigen and the therapy that induces the death of neoplastic cells are administered sequentially. In some embodiments, the encapsulated CD1d-restricted iNKT cell antigen and/or the therapy that induces the death of neoplastic cells is/are administered multiple times. In some embodiments, the encapsulated CD1d-restricted iNKT cell antigen and/or the therapy that induces the death of neoplastic cells is/are administered at least once a week over the course of several weeks. In some embodiments, the encapsulated CD1d-restricted iNKT cell antigen and/or the therapy that induces the death of neoplastic cells is/are administered at least once a week over several weeks to several months. In some embodiments, the encapsulated CD1d-restricted iNKT cell antigen and/or the therapy that induces the death of neoplastic cells is/are administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more. In some embodiments, the encapsulated CD1d-restricted iNKT cell antigen and/or the therapy that induces the death of neoplastic cells is/are administered about twice every week. In some embodiments, the encapsulated CD1d-restricted iNKT cell antigen and/or the therapy that induces the death of neoplastic cells is/are administered twice a week for about 2, about 3, about 4, about 5, about 6, about 7, about 8, about 9, about 10, about 11, about 12, about 13, about 14, about 15, about 16, about 17, about 18, about 19 or about 20 weeks or more.

In some embodiments, the subject that is treated with an adjuvant composition provided herein is a mammal, a human, a non-human primate, a dog, a cat, a cow, a sheep, a horse, a rabbit, a mouse, or a rat.

In some embodiments, the neoplastic disease is cancer. In some embodiments, the cancer is selected from the group consisting of lung cancer, breast cancer, brain cancer, liver cancer, colon cancer, pancreatic cancer, and bladder cancer. In some embodiments, the cancer is selected from the group consisting of an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor; breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonaryblastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström's macroglobulinemia; and Wilms' tumor. In some embodiments, the cancer is malignant. In some embodiments, the cancer is recurrent or relapsed cancer.

Also described herein, in certain embodiments, are pharmaceutical compositions comprising an adjuvant composition provided herein and at least one pharmaceutically acceptable carrier.

Also described herein, in certain embodiments, are uses of an adjuvant composition comprising an immunogenically effective amount of (a) an encapsulated CD1d-restricted iNKT cell antigen that is capable of uptake by a phagocytic cell and (b) a pharmaceutically acceptable carrier for the treatment of a neoplastic disease.

Also described herein, in certain embodiments, are uses of an adjuvant composition comprising an immunogenically effective amount of (a) an encapsulated CD1d-restricted iNKT cell antigen that is capable of uptake by a phagocytic cell and (b) a pharmaceutically acceptable carrier in the preparation of a medicament for the treatment of a neoplastic disease.

Both the foregoing summary and the following description of the drawings and detailed description are exemplary and explanatory. They are intended to provide further details of the invention, but are not to be construed as limiting. Other objects, advantages, and novel features will be readily apparent to those skilled in the art from the following detailed description of the invention.

BRIEF DESCRIPTION OF THE DRAWINGS

FIG. 7A=$_{Ep}$minicell$_{Dox}$ (1×10$^9$)+minicell$_{\alpha\text{-}GC}$ (1×10$^7$); 16 hr; FIG. 7B=$_{Ep}$minicell$_{Dox}$ (1×10$^9$)+minicell$_{\alpha\text{-}GC}$ (1×10$^7$); 24 hr.

FIGS. 8A-E show αGC-CD1d presentation of JAWS II cells following minicell$_{\alpha GC}$ treatment at various time points (FIGS. 8A-D). FIG. 8A=8 hrs; FIG. 8B=16 hrs; FIG. 8C=24 hrs; FIG. 8D=48 hrs; FIG. 8E shows αGC-CD1D positive JAWSII cells during the course of treatment.

FIG. 13B=8 hrs; FIG. 13C=16 hrs; and FIG. 13D=24 hrs.

FIG. 14B=8 hrs; FIG. 14C=16 hrs; and FIG. 14D=24 hrs.

FIG. 15B=8 hrs; FIG. 15C=16 hrs; and FIG. 15D=24 hrs.

FIG. 16B=8 hrs; FIG. 16C=16 hrs; and FIG. 16D=24 hrs.

FIG. 17B=8 hrs; FIG. 17C=16 hrs; and FIG. 17D=24 hrs.

DETAILED DESCRIPTION

I. Overview

Figure 1:
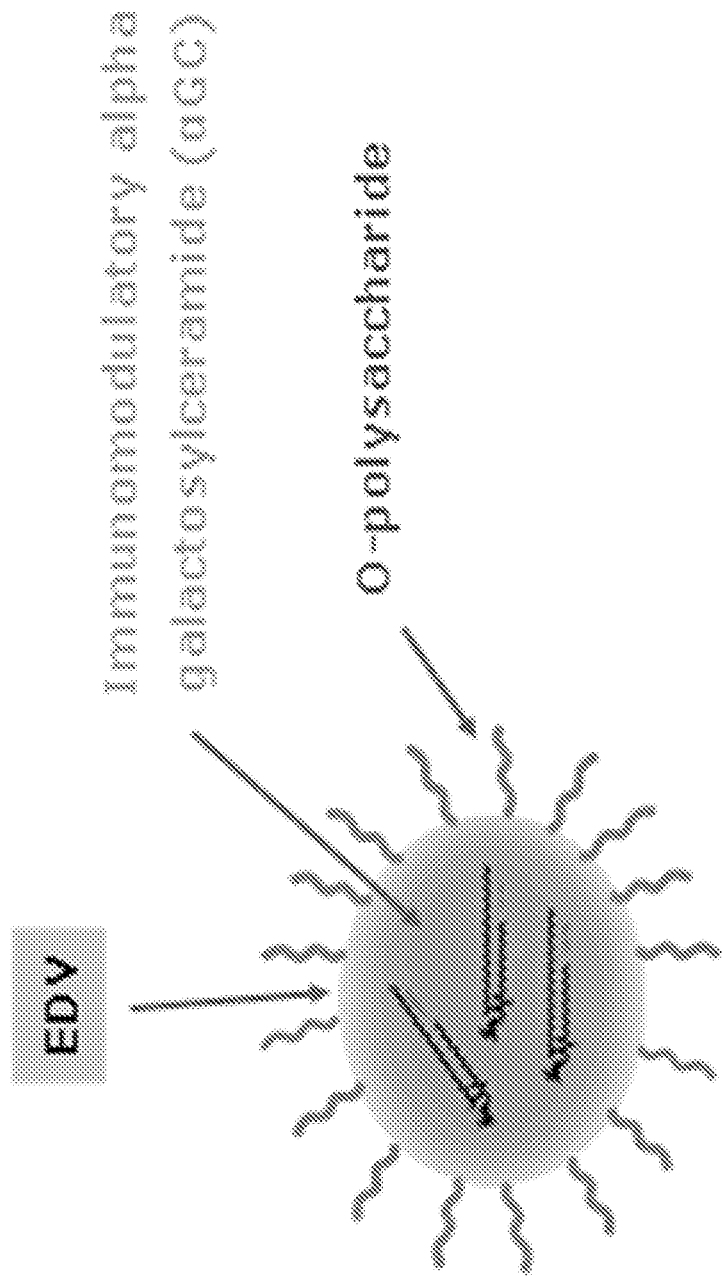
FIG. 1 is a graphical depiction of an EnGeneIC Dream Vehicle (EDV) (e.g., a bacterial minicell) loaded with the CD1d-restricted iNKT cell antigen α-galactosylceramide (α-GalCer).
Figure 2:
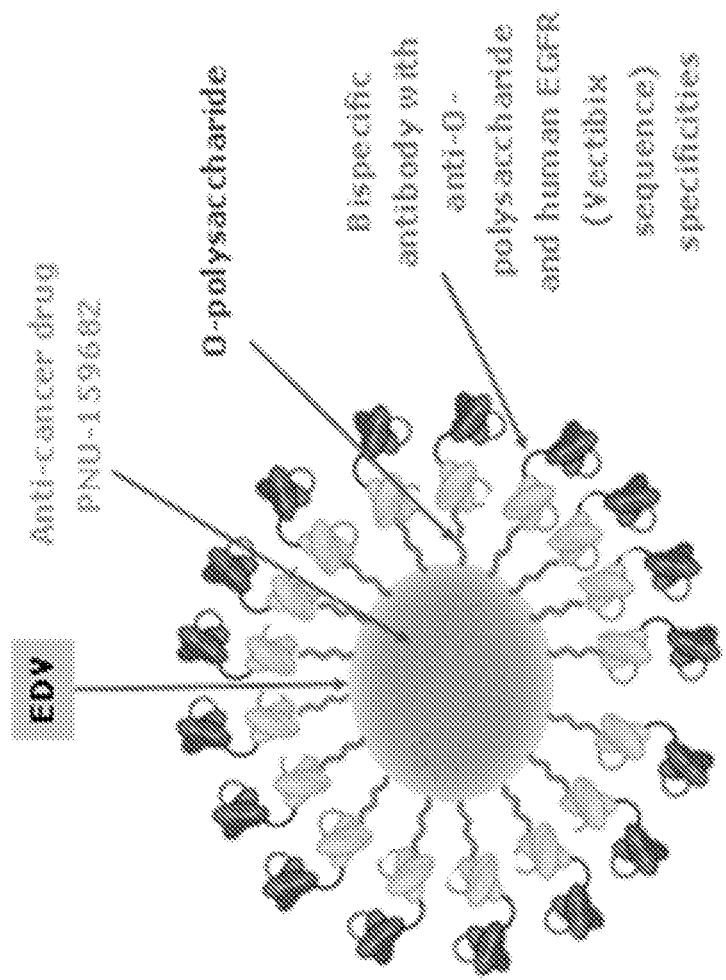
FIG. 2 is a graphical depiction of an EDV (e.g., a bacterial minicell) comprising a bispecific antibody for O-polysaccharide and human epidermal growth factor receptor antigens and loaded with the anti-cancer drug PNU-159682 (an anthracycline analogue).
Figure 3:
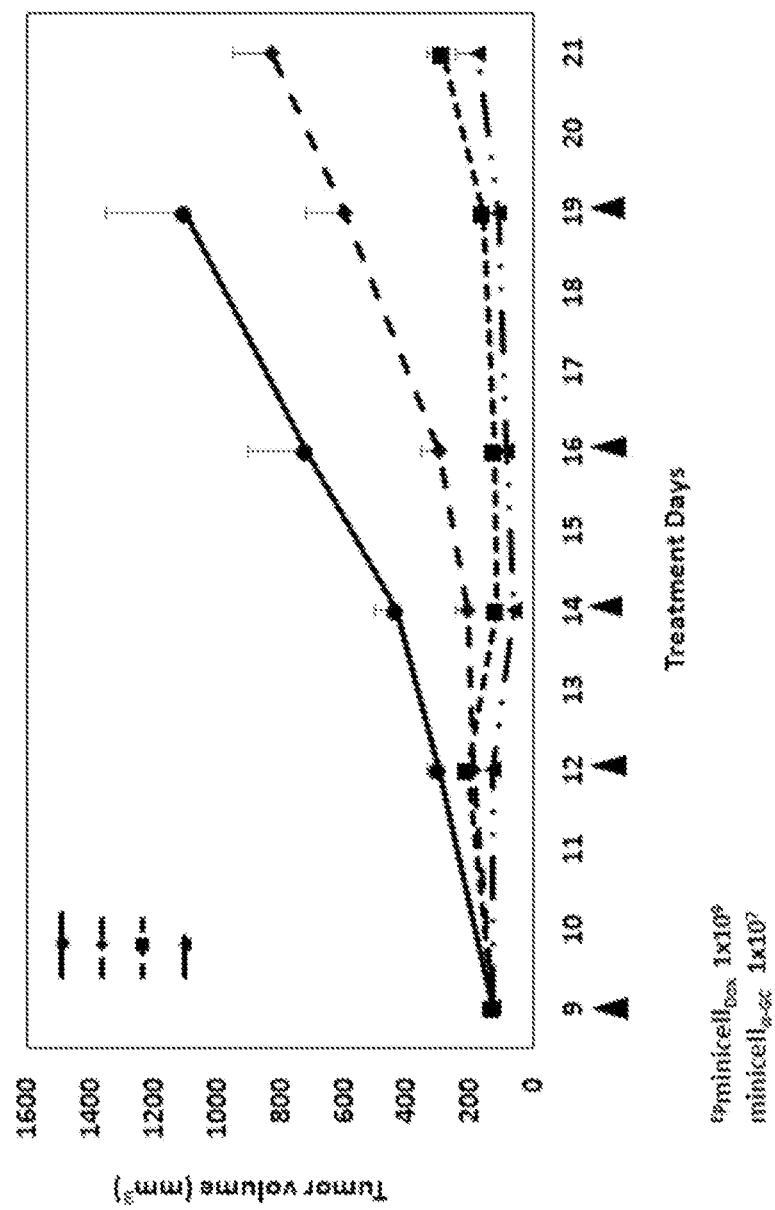
FIG. 3 shows combination treatment using $^{EP}$minicell$_{Dox}$ and minicell$_{\alpha\text{-}GC}$ in a syngeneic mouse model ($^{EP}$CT26 colon tumors in Balb/c mice).

The present invention is based in part on the discovery that compositions comprising an immunogenically effective amount of intact, bacterially derived minicells or killed bacterial cells that encapsulate a CD1d-restricted invariant Natural Killer T (iNKT) cell antigen (e.g., a sphingolipid, such as α-galactosylceramide), when administered with an antineoplastic agent, synergistically improve cancer treatment strategies. As shown in Examples 1 and 2, an encapsulated α-galactosylceramide (α-GalCer), which is contained within a bacterially-derived minicell, is taken up by phagocytic cells and expressed on the surface of the cell in a complex with CD1d. The encapsulated α-GalCer was able to significantly and synergistically augment the antitumor response when administered in combination with an antineoplastic agent, doxorubicin.

Prior attempts have been made to deliver α-GalCer for anti-tumor therapy. These have included administration of α-GalCer either as a free molecule or packaged in liposomes or polymers (see, e.g., Giaccone et al., 2002; Nakamura et al., 2013; and Faveeuw et al., 2014). However, these approaches have resulted in toxicity and limited anti-tumor efficacy in human clinical trials. These approaches were designed to use free or packaged α-GalCer as adjuvants to elicit an iNKT cell response only. By contrast, the present invention not only directly kills cancer cells but also elicits an innate and adaptive anti-tumor responses. The components of this combined therapy include induction of an immune response elicited by an antineoplastic agent (e.g., a cytotoxic agent comprised in a bacterially derived minicell) to trigger tumor cell killing and activate a potent CD4+ and CD8+ anti-tumor responses and use of bacterially derived minicells carrying α-GalCer, which biases the antigen processing and presentation towards MHC class 1 (CD1d-restricted) to mount a potent iNKT cell-based anti-tumor response. The minicells themselves elicit an innate immune response via recognition of damage-associated molecular pattern (DAMP) molecules, which are released by dying tumor cells, by the antigen presenting cells (APC). Induction of the innate immune response, involving pro-inflammatory cytokines are critical to this process since it elicits the activation and differentiation of bone marrow derived macrophages and dendritic cells. This process dramatically enhances anti-tumor immunity. By contrast, a carrier such as a liposome or polymer is incapable of eliciting an innate immune response. Therefore, anti-tumor efficacy will be lower compared to the bacterially derived minicells of the present disclosure since the anti-tumor activity of the liposome or polymer carried α-GalCer is solely reliant on iNKT cell activation and not on the formation of M1 macrophages and activation of dendritic cells.

Recent advances in cancer immunotherapy have resulted in unprecedented, durable clinical responses in specific cancers (Emens et al., 2017; Farkona et al., 2016; Oiseth and Aziz, 2017; Sharma et al., 2017; Ventola, 2017). However, current immunotherapeutic strategies have resulted in limited success rates across a variety of tumor types and a significant proportion of patients who initially demonstrate encouraging tumor regression relapse over time (Emens et al., 2017; Mellman et al., 2011; Oiseth and Aziz, 2017; Sharma et al., 2017; Ventola, 2017).

Further, a subset of patients lacks tumor immunogenicity resulting from an absence of tumor cell antigens or lack of immune cell infiltration and therefore exhibit no initial response to the current strategies available (Emens et al., 2017; Oiseth and Aziz, 2017; Sharma et al., 2017). Thus, the identification of novel, robust immunotherapeutic approaches may result in significantly improved clinical outcomes and remains an area of high priority.

To mount an effective anti-tumor immune response, certain steps must be achieved either spontaneously or therapeutically. First, tumor cell antigens which may be derived in situ via tumor cell death, or delivered exogenously must be taken up by dendritic cells (DC) (Anguille et al., 2015; Emens et al., 2017; Jung et al., 2018; Mellman et al., 2011). In conjunction with antigen uptake, DCs need to receive a proper maturation signal prompting differentiation and enhanced processing and presentation of antigens such that antitumor function as opposed to tolerance is promoted (Anguille et al., 2015; Emens et al., 2017; Jung et al., 2018; Mellman et al., 2011; Simmons et al., 2012). These mature, tumor antigen loaded DCs must then effectively generate antitumor T-cell responses which can occur via production of tumor specific cytotoxic T-cells, triggering of NK and/or NKT cell responses, and enhancing T-helper type 1 responses, among others (Emens et al., 2017; Fang et al., 2017; Mellman et al., 2011; Sharma et al., 2017; Zitvogel et al., 2015). Antitumor T-cells must finally enter the tumor microenvironment, where immune suppressive signals may be present, and effectively perform their antitumor function (Emens et al., 2017; Mellman et al., 2011). Problems arising in any of these steps will impede efficacy of an immunotherapeutic, and can even result in total failure of the therapy (Emens et al., 2017; Mellman et al., 2011; Sharma et al., 2017).

Currently, the immunotherapeutic strategies which have received the most attention clinically include immunological checkpoint inhibitors and chimeric antigen receptor T-cell therapy (CAR-T) (Emens et al., 2017; Mellman et al., 2011; Oiseth and Aziz, 2017; Sharma et al., 2017; Ventola, 2017). Checkpoint inhibitors such as cytotoxic T lymphocyte antigen 4 (CTLA-4), and programmed cell death 1/programmed cell death 1 ligand (PD-1/PDL-1) function by blocking the transmission of immune-suppressive signals and direct stimulation to activate cytotoxic T lymphocytes within the tumor microenvironment (Dine et al., 2017; Jenkins et al., 2018; Sharpe, 2017). Inhibitors of these pathways have shown dramatic clinical results in specific cancers, but overall response rates across different cancers remains low (~15-25%) and immune related toxicities associated with these therapies can be high (Dine et al., 2017; Emens et al., 2017; Jenkins et al., 2018; Sharpe, 2017; Ventola, 2017). With new checkpoints continually being discovered as potential immune targets, it is apparent that tumors are capable of exploiting an elaborate and diverse set of immune-suppressive pathways (Dine et al., 2017; Emens et al., 2017; Farkona et al., 2016; Jenkins et al., 2018; Sharpe, 2017). Thus, development of resistance to checkpoint inhibitors continues to be a hurdle and attempts are being made to utilize combinations of more than one checkpoint inhibitor to overcome these issues, though this often exacerbates associated toxicities (Dine et al., 2017; Jenkins et al., 2018; Sharma et al., 2017; Ventola, 2017).

The second therapy receiving widespread attention is CAR-T cell therapy which entails the genetic engineering of a patient's T-cells to express membrane fusion receptors with defined tumor antigen specificities and capable of eliciting robust T-cell activation to initiate killing of the target tumor cells (D'Aloia et al., 2018'; Farkona et al., 2016; Mellman et al., 2011; Sharma et al., 2017). This therapeutic approach has produced unprecedented clinical outcomes in the treatment of "liquid" hematologic cancers, but to date has not produced comparable responses in targeting solid malignancies due to limitations associated with the lack of a good specific antigen target, poor homing to the tumor, poor extravasation into the tumor, and lack of persistence within a hostile tumor microenvironment (D'Aloia et al., 2018'; Sharma et al., 2017). Practical limitations relating to the availability of lymphocytes from heavily pre-treated patients and long manufacturing times and are not a feasible treatment option for patients with rapidly advancing disease are also present (Oiseth and Aziz, 2017; Rezvani et al., 2017).

The EnGeneIC Dream Vector (EDV) is a bacterially-derived delivery system consisting of nonviable nanocells that are about 400±20 nm in diameter, generated by reactivating polar sites of cell division in bacteria (MacDiarmid et al., 2007b). It has been demonstrated that these nanocells can be packaged with a cytotoxic drug, siRNA, or miRNA and specifically targeted to tumor cell-surface receptors via attachment of bispecific antibodies to the surface polysaccharide of the nanocells (MacDiarmid et al., 2009; MacDiarmid et al., 2007b; Reid et al., 2013). Post-intravenous administration in mouse and dog studies has demonstrated that they are retained in the vascular system due to their size, but then rapidly extravasate into the tumor via the tumor-associated leaky vasculature (MacDiarmid et al., 2007b; Sagnella et al., 2018). Post-tumor cell-surface receptor engagement via the associated bispecific antibody results in macropinocytosis into endosomes and release of the payload via degradation intracellularly in the lysosomes (MacDiarmid et al., 2009; MacDiarmid et al., 2007b; Sagnella et al., 2018). The safety of these nanocell therapeutics has been demonstrated in three Phase I clinical trials, with over a thousand doses administered in various end-stage cancer patients. Further, PNU-159682 cytotoxic drug-loaded, EGFR-targeted EDVs, Doxorubicin-packaged, EGFR-targeted EDVs, micro RNA mir16a-packaged EDVs, EGFR-targeted EDVs are currently being delivered to patients in a phase I clinical trial and to date have shown a promising safety profile (NHMRC Clinical Trials Centre, 2017; Kao et al., 2015; Solomon et al., 2015; van Zandwijk et al., 2017; Whittle et al., 2015).

A. Overview of Bacterial Minicell Delivery Methods

The use of bacterially-derived minicells to deliver chemotherapeutic agents to cancer cells has previously been described. This delivery method to treat cancer packages a toxic chemotherapy agent or drug, or functional nucleic acid, into a bacterially-derived minicell, which are typically about 400 nm in diameter. Typically, the minicell carrying a chemotherapeutic agent an antibody targeting specific cancer cells. The antibodies attach to the surface of cancer cells and the minicell is internalized by the cancer cell. In this way, the toxic chemotherapy agents are not widely distributed throughout the body, and therefore reduce the chance of side effects and intolerability as the toxic drug or compound is delivered inside the cancer cell. Using antibody-targeted minicells as a delivery vehicle for toxic chemotherapy agents results in much less drug needed to kill the cancer cell, thus improving the therapeutic index.

Indeed, the present inventors have shown that minicells (or EnGeneIC Dream Vehicles, EDVs) can deliver chemotherapy drugs, such as paclitaxel or doxorubicin, to xenograft tumors in mice, dogs, and monkeys. The targeted delivery ensures that the cancer cells receive most of the chemotherapeutic agent, resulting in a low level of toxicity. See MacDiarmid et al., 2007b; MacDiarmid et al., 2007a; MacDiarmid et al., 2009; and MacDiarmid et al., 2016.

Furthermore, the minicells do not induce a significant immune response in the xenograft models, and the minicells are well tolerated. Thus, intact bacterially derived minicells are a well-tolerated vehicle for delivering anti-cancer drugs to patients, with examples including doxorubicin targeted to advanced solid tumors, doxorubicin targeted to glioblastoma, and MicroRNA-16a targeted to mesothelioma. However, these treatment strategies did not result in complete remission or cure of all cancers in all patients. Accordingly, there is a need for improved cancer treatment therapies.

The present inventors discovered that using a combination of bacterially-derived minicells comprising a CD1d-restricted invariant Natural Killer T (iNKT) cell antigen and an antineoplastic agent produced surprisingly dramatic and effective clinical efficacy. In a specific embodiment, the bacterially-derived minicells comprising a CD1d-restricted invariant Natural Killer T (iNKT) cell antigen do not comprises a targeting agent and the bacterially-derived minicells comprising an antineoplastic agent comprises a targeting agent.

Specifically, the present inventors discovered that minicells comprising a CD1d-restricted invariant Natural Killer T (iNKT) cell antigen, such as α-GalCer, combined with minicells comprising an antineoplastic agent (e.g., doxorubicin), resulted in synergistic anti-tumor effects. These data are described in more detail below.

The data reveal a unique pathway for anti-tumor immunity based on innate and adaptive immune responses. Without being bound by theory, it is hypothesized the minicells comprising α-GalCer and the minicells comprising an antineoplastic agent extravasate into the tumor microenvironment via the leaky vasculature associated with a solid tumor. Targeted minicells comprising the antineoplastic agent and an anti-EGFR targeting agent are internalized by the tumor cells via macropinocytosis. Once inside the tumor cells the minicells are broken down, resulting in the release of the antineoplastic drug and inducing tumor cell apoptosis. The apoptotic tumor cells rapidly expose calreticulin on their surface followed by phosphatidylserine (a marker of apoptosis) and release damage-associated molecular pattern (DAMP) molecules such as ATP (during apoptosis) and HMGB1 upon secondary necrosis.

The minicells that do not make it to the tumor microenvironment, are engulfed by cells of the immune system (e.g., macrophages and dendritic cells) found in the vasculature associated with the liver, spleen and lymph nodes. The minicells are broken down in lysosomes and the released LPS escapes from lysosomal membranes and binds to caspase 4 and caspase 5 via the CARD (caspase recruit domain) domains. This LPS binding facilitates rapid oligomerization of caspase 4/5 resulting in pyroptosis of the macrophage or dendritic cell and the secretion of pro-inflammatory cytokines IL-1β and IL-18. The process of pyroptosis also triggers the release of a plethora of pro-inflammatory cytokines such as TNF-α, IL-6, IL-8, and IL-10. These proinflammatory signals are picked up by monocytes in the bone marrow and these cells differentiate into activated macrophages and dendritic cells, which extravasate from the bone marrow and enter into the general circulation.

The DAMPs (ATP and HMGB1) released from dying tumor cells generates a strong "find-me" signal for dendritic cells and macrophages, upon its binding to P2Y2 receptors expressed on the surface of the target cells. Extracellular ATP not only attracts immune cells into the tumor microenvironment, but also modulates their activity. For example, ATP can induce the maturation of myeloid-derived DCs, which is accompanied by increased expression of CD40, CD80, CD83, and CD86, and also promote macrophage expansion through formation of lamellipodial membrane protrusions. These newly differentiated active macrophages and dendritic cells follow the "find-me" signals and enter into the tumor microenvironment.

Calreticulin on the surface of apoptotic tumor cells is functionally considered as an "eat-me" signal to the immune system. Cells with calreticulin expression on their surface are recognized and engulfed by CD91+ cells (e.g., dendritic cells and macrophages). Calreticulin acts on target dendritic cells via CD91 expressed on their surface to promote the release of pro-inflammatory cytokines e.g., TNF-a and IL-6 and modulate the activity of type 17 helper T (Th17) cells in an immunosuppressive tumor bed. The binding of calreticulin to CD91 also facilitates the recruitment of antigen presenting cells e.g., dendritic cells into the tumor microenvironment, engulfment of tumor cells by dendritic cells, and optimal antigen presentation to T cells, eventually leading to activation of the immune system.

HMGB1 triggers a strong inflammatory response. HMGB1 activates dendritic cells and stimulates an optimal presentation of tumor-associated antigens to T cells, upon its binding to TLR4.

RAGE (receptor for advanced glycation end products) is another important receptor for HMGB1. Binding of HMGB1 to RAGE promotes dendritic cell maturation and migration through activation of MAPKs (p38 and ERK1/2) and NF-kB.

These DAMPs stimulate the recruitment of dendritic cells into the tumor microenvironment, the uptake and processing of tumor antigens, and the optimal antigen presentation to T cells. Cross-priming of CD8+ cytotoxic T cells is triggered by mature dendritic cells and γδT cells in an IL-1β- and IL-17-dependent manner. Primed CD8+ cytotoxic T cells then elicit a direct cytotoxic response to kill remaining tumor cells through the generation of IFN-γ, perforin-1 and granzyme B.

Many of the circulating minicells comprising α-GalCer are engulfed by the macrophages and dendritic cells present within the vasculature associated with the liver, spleen and lymph nodes. The minicells are broken down within the lysosomes and the α-galactosylceramide is released. Within the acidic lysosomes, with the aid of lipid exchange proteins such as saposins, α-galactosylceramide forms complexes with CD1d. These complexes are transported to the cell surface and localize predominantly to cholesterol rich microdomains, the lipid rafts, in the plasma membrane. Thymus derived invariant Natural Killer T cells (iNKT) recognize lipid antigens presented by CD1d via their unique T Cell Receptor (TCR) repertoire Vα24Jα18. iNKT cells carry pre-existing mRNA for IFNγ and hence rapidly secrete IFNγ post-TCR/Cd1d/α-GalCer binding. iNKT cells also rapidly secrete multiple cytokines upon TCR triggering which is accompanied by an increased CD1d-restricted cytotoxic capacity of various cells of the immune system. Cytokines released by iNKT include both regulatory cytokines (e.g., IL-4, IL-10, IL-13) as well as proinflammatory cytokines such as IL-2, IL-17, and IFNγ. Post-activation, iNKT cells can directly kill tumor cells mediated by classical granule-mediated mechanisms. Upon recognition of CD1d: lipid complexes and the costimulatory molecules CD80/86 on the surface of dendritic cells, iNKT cells up-regulate the IL-12R and CD40L molecule. Subsequently, and mediated by CD40L, iNKT induce dendritic cell maturation and release of IL-12. This IL-12 release in turn potently increases IFNγ production by iNKT which then, together with enhanced cross-presentation of DCs after iNKT induced maturation, boosts activation of anti-tumorigenic cytotoxic CD8+ T lymphocytes (CTL). iNKT cells therefore have the capacity to jump-start immune responses and together with dendritic cells, bridge the innate and adaptive immune systems. The release of IFNγ biases professional phagocytic cells towards Th1 type of immune responses by expressing MHC1 molecules for presentation of unique glycolipid tumor antigens. Therefore, the minicells comprising the neoplastic agent starts the tumor killing process, the minicells comprising α-GalCer and minicells comprising the neoplastic agent trigger the innate immune response, and minicells comprising α-GalCer activate the adaptive immune response resulting in the immune system taking over the tumor-specific killing process.

As described above and in the Examples presented herein, the inventors of the present disclosure have found that a CD1d-restricted iNKT cell antigen α-GalCer encapsulated within a bacterially derived minicell combined an antineoplastic agent surprisingly produced synergistic anti-tumor effects. Given that the synergistic effect appears to depend in part on cell death-inducing activities of the antineoplastic agent, any antineoplastic agent that is able to induce cell death of cancer cells is suitable for use in combination with an encapsulated CD1d-restricted iNKT cell antigen. In one embodiment, the antineoplastic agent is also contained within a bacterially-derived minicell. In another embodiment, the antineoplastic agent is not contained within a bacterially-derived minicell. Further, as described in further detail below, CD1d-restricted iNKT cell antigens in addition to α-GalCer are known and have been shown to effect iNKT cell activation and can be used in place of or in combination with α-GalCer in the compositions and methods provided herein.

The following description outlines the invention related to these discoveries, without limiting the invention to the particular embodiments, methodology, protocols, or reagents described. Likewise, terminology used here describes particular embodiments only and does not limit the scope of the invention.

B. Summary of the Experimental Results

In one embodiment, this invention relates to the surprising discovery that compositions comprising a combination of a minicell-packaged antineoplastic agent and a minicell packaged type II interferon agonist, such as for example alpha-galactosylceramide (α-GC), and in the absence of a type I interferon agonist, demonstrates surprising anticancer efficacy.

In particular, Example 1 describes data illustrating the efficacy of a dual combination of minicell contained antineoplastic therapeutic and minicell contained CD1d-restricted iNKT cell antigen (e.g., α-GalCer) against tumors. See FIGS. 3-6. The experimental results showed a marked halt in tumor progression for combination treatment groups receiving $^{Ep}$minicell$_{Dox}$+minicell$_{α-GC}$ (α-GalCer) as compared to saline and $^{Ep}$minicell$_{Dox}$ treatments. This result supports the theory of an immune adjuvant effect by the addition of minicell$_{α-GC}$ treatment to $^{Ep}$minicell$_{Dox}$.

Further data showed that saline treated control tumors demonstrated dramatic tumor regression following a treatment change to drug and α-GalCer EDV mediated dual combination therapy (FIG. 6); e.g., a combination of minicell packaged antineoplastic agent and minicell packaged type II interferon agonist (e.g., a CD1d-restricted iNKT cell antigen, such as α-GalCer). In particular, tumors that had reached 800 mm³ dropped to below 600 mm³ in 3 days before the experiment was terminated—a markedly dramatic tumor size reduction (~25%) in a short period of time. The ability for the dual combination composition to dramatically decrease large tumors in a short period of time was not known prior to the present invention.

In one embodiment of the invention, the dual combination composition (e.g., a minicell packaged antineoplastic agent in combination with a minicell packaged CD1d-restricted iNKT cell antigen, such as α-GalCer), can reduce a tumor's size, including the size of a large tumor, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 175%, about 200%, about 225%, about 250%, about 275%, about 300%, about 325%, about 350%, about 375%, about 400%. about 425%, about 450%, about 475%, or about 500%. The reduction in tumor size can be measured over any suitable time period, such as about 3 days, about 5 days, about 1 week, about 2 weeks, about 3 weeks, about 1, about 2, about 3, about 4, about 5, about 6, about 7, about 8, about 9, about 10, about 11, about 12 months, about 1.5 years, about 2 years or longer.

Bacterial minicell treatment represents a unique cancer therapeutic strategy capable of delivering conventional and novel drug therapies directly to the tumor site and subsequently eliciting an antitumor immune response. A dual assault on the tumor occurs, first through cell death in response to the delivered therapeutic and followed by innate immune cell activation leading to an adaptive immune response. This type of therapy has certain advantages over current immunotherapy strategies in that immune cell activation occurs both in vivo and primarily at the tumor site, which is a rapidly changing, dynamic environment. Further, it creates an immunogenic tumor environment and elicits effects on multiple immune cell subsets avoiding problems associated with patients who show little to no immune response to their tumors or adaptations to therapies which only target single immune cell subsets. The study described below highlights the potential of bacterial minicells as a novel cancer immunotherapeutic, and future bacterial minicell formulations could further exploit its inherent immunogenic nature given the versatility of this technology with respect to both payload and targeting ability (MacDiarmid et al., 2007a)

II. Composition Components

As noted above, the compositions of the invention comprise an encapsulated CD1d-restricted iNKT cell antigen (e.g., α-GalCer) that is administered in combination with an antineoplastic agent that induces the death of neoplastic cells in the subject. In some embodiments, the CD1d-restricted iNKT cell antigen is encapsulated in a bacterially-derived minicell or killed bacterial cell as described herein.

In some embodiments, the CD1d-restricted iNKT cell antigen is encapsulated with an antineoplastic agent in a bacterially-derived minicell or killed bacterial cell. In some embodiments, the CD1d-restricted iNKT cell antigen and the antineoplastic agent are encapsulated in separate bacterially-derived minicells or killed bacterial cells. In some embodiments, the CD1d-restricted iNKT cell antigen and the antineoplastic agent are contained in the same composition. In some embodiments, the CD1d-restricted iNKT cell antigen and the antineoplastic agent are contained in the separate compositions. In some embodiments, the CD1d- restricted iNKT cell antigen is encapsulated in a bacterially-derived minicell or killed bacterial cell and the antineoplastic agent is encapsulated in a bacterially-derived minicell or killed bacterial cell. In some embodiments, the CD1d-restricted iNKT cell antigen is encapsulated in a bacterially-derived minicell or killed bacterial cell and the antineoplastic agent is not encapsulated in a bacterially-derived minicell or killed bacterial cell.

A. CD1d-Restricted iNKT Antigens

Type II IFNs play an important role in anti-tumor immunity by activating cytotoxic T cells. See, e.g., Chikuma et al., 2017. IFN gamma cytokines are released by innate Natural Killer cells upon binding of natural antigen, but glycosphingolipid compounds function as potent activators of both innate and acquired immune responses. The present inventors discovered that encapsulated CD1d-restricted iNKT cell antigens, such as the glycosphingolipid α-GalCer, are engulfed by phagocytic cells, such as macrophages and dendritic cells, and then expressed on the surface of the cells bound to the surface glycoprotein CD1d. Recognition of the expressed glycosphingolipid bound to CD1d induces a potent cytokine response by innate natural killer T (iNKT) cells, including the type II interferon, IFN-γ, and a number of Interleukins (Th1-, Th2-, and/or Th17-type cytokines). See, e.g., Carreno et al., 2016. iNKT cells then induce DC maturation and display T cell helper-like functions that result in the development of cytotoxic T cell responses.

Examples of CD1d-restricted iNKT cell antigens useful for the compositions described herein include, but are not limited to, glycosphingolipids, such as α-galactosylceramide (α-GalCer), C-glycosidific form of α-galactosylceramide (α-C-GalCer), 12 carbon acyl form of galactosylceramide (β-GalCer), β-D-glucopyranosylceramide (β-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan (LPG), lyosphosphatidylcholine (LPC), α-galactosylceramide analog (OCH), and threitolceramide. In a particular embodiment, the compositions disclosed herein comprises and encapsulated α-galactosylceramide (α-GalCer).

In some embodiments, the glycosphingolipid is a synthetic α-GalCer analog. In some embodiments, the synthetic α-GalCer analog is selected from among 6'-deoxy-6'-acetamide α-GalCer (PBS57), naphthylurea α-GalCer (NU-α-GC), NC-α-GalCer, 4ClPhC-α-GalCer, PyrC-α-GalCer, α-carba-GalCer, carba-α-D-galactose α-GalCer analog (RCAI-56), 1-deoxy-neo-inositol α-GalCer analog (RCAI-59), 1-O-methylated α-GalCer analog (RCAI-92), and HS44 aminocyclitol ceramide.

In some embodiments, the CD1d-restricted iNKT cell antigen is derived from a bacterial antigen, a fungal antigen, or a protozoan antigen. In some embodiments, the CD1d-restricted iNKT cell antigen is a glycosphingolipid from the bacterial species Sphinomonadacae spp. In some embodiments, the glycosphingolipid is Sphinomonadacae spp. glycosphingolipid-1 (GSL-1), GSL-1', GSL-2, GSL-3, or GSL-4. In some embodiments, the CD1d-restricted iNKT cell antigen is a glycolipid from the bacterial species Streptococcus spp. In some embodiments, the glycolipid is S. pneumoniae Glc-diacyl glycerol (DAG) or Gal-Glc-DAG. In some embodiments, the CD1d-restricted iNKT cell antigen is a glycolipid from the bacterial species Borrelia spp. In some embodiments, the glycolipid is B. burgdorferi BbGL-IIc. In some embodiments, the CD1d-restricted iNKT cell antigen is a glycolipid from the bacterial species Helicobacter pylori. In some embodiments, the glycolipid is H. pylori PI57. Other CD1d-restricted iNKT cell bacterial antigens useful in the compositions and methods provided herein include, but are not limited to, monoglycosylceramides derived from Spongemonas, phosphotidylinositol mannosides derived from Mycobacterium tuberculosis and lipopphosphoglycans derived from Leishmania donovi.

In some embodiments, the CD1d-restricted iNKT cell antigen is a fungal glycolipid from Aspergillus spp., such as A. fumigatus or A. niger. In some embodiments, the glycolipid is A. fumigatus aperamide B. In some embodiments, the CD1d-restricted iNKT cell antigen is a glycolipid from the protozoan Entamoeba histolytica. In some embodiments, the glycolipid is E. histolytica EhP1b.

Additional exemplary CD1d-restricted iNKT cell antigens, including additional α-GalCer derivatives, useful for the compositions provided herein include those described in US2017/0368002, Birkholz and Kronenberg, 2015, and Anderson, 2013, which are each incorporated by reference in their entirety.

As shown in Example 1, Applicant discovered that tumor containing mice that were administered intact bacterially-derived minicells containing the chemotherapeutic doxorubicin ($^{Ep}$minicell$_{Dox}$) and minicells containing the CD1d-restricted iNKT cell antigen α-GalCer (minicell$_{α\text{-}GC}$) displayed a marked halt in tumor progression over mice administered only $^{Ep}$minicell$_{Dox}$. These observations indicated that minicell compositions incorporating a CD1d-restricted iNKT cell antigen are effective at treating tumors in mice. The minicell can deliver type II IFN agonists, such as CD1d-restricted iNKT cell antigens, directly to cells of the immune system, for enhancing iNKT cell activation and type II interferon IFN-γ production in vivo. Alternatively, non-targeted encapsulated CD1d-restricted iNKT cell antigens are taken up by phagocytic cells of the immune system, where they are broken down in endosomes, and aGC is presented to iNKT cells for immune activation.

Accordingly, in some embodiments the compositions described herein provide targeted delivery of type II interferon agonists, such as the CD1d-restricted iNKT cell antigens. In other embodiments, the compositions disclosed herein comprise a non-targeted delivery of the CD1d-restricted iNKT cell antigens.

IFN-γ production is controlled by cytokines secreted by antigen presenting cells (APCs), most notably interleukin (IL)-12 and IL-18. These cytokines serve as a bridge to link infection with IFN-γ production in the innate immune response. Macrophage recognition of many pathogens induces secretion of IL-12 and chemokines. These chemokines attract NK cells to the site of inflammation, and IL-12 promotes IFN-γ synthesis in these cells. In macrophages, natural killer cells and T cells, the combination of IL-12 and IL-18 stimulation further increases IFN-γ production. Accordingly, any of these proteins or their combinations are suitable agents for or use in combination with the compositions and methods provided herein.

The data show that the serum concentration of IFN-γ required for effectively activating host immune response to tumor cells is low when the patient also receives administration of an antineoplastic therapy, such as a chemotherapeutic drug or drug-loaded, bispecific antibody-targeted minicells as described herein. Thus, in one aspect the inventive methodology results in increase of serum IFN-γ concentration that is not higher than about 30,000 pg/mL. In another aspect, the serum IFN-γ concentration is increased to not higher than about 5000 pg/mL, 1000 pg/mL, 900 pg/mL, 800 pg/mL, 700 pg/mL, 600 pg/mL, 500 pg/mL, 400 pg/mL, 300 pg/mL, 200 pg/mL, or 100 pg/mL. In a further aspect, the resulting serum IFN-gamma concentration is at least about 10 pg/mL, or at least about 20 pg/mL, about 30 pg/mL, about 40 pg/mL, about 50 pg/mL, about 60 pg/mL, about 70 pg/mL, about 80 pg/mL, about 90 pg/mL, about 100 pg/mL, about 150 pg/mL, about 200 pg/mL, about 300 pg/mL, about 400 pg/mL or about 500 pg/mL.

B. Antineoplastic or Cytotoxic Active Agents Useful in Treating Cancer

The phrase "antineoplastic agent" denotes a drug, whether chemical or biological, that prevents or inhibits the growth, development, maturation, or spread of neoplastic cells. The term "antineoplastic agent" is used interchangeably with "anticancer agent" and "chemotherapy agent."

In the context of this disclosure, selecting an antineoplastic agent for treating a given tumor depends on several factors. These factors include but are not limited to the patient's age, the stage of the tumor, and whatever previous therapy the patient may have received.

The composition can comprise at most about 1 mg of the antineoplastic or chemotherapeutic drug. Alternatively, the amount of the chemotherapeutic drug can be at most about 750 µg, about 500 µg, about 250 µg, about 100 µg, about 50 µg, about 10 µg, about 5 µg, about 1 µg, about 0.5 µg, or about 0.1 µg. In another aspect, the composition comprises a chemotherapeutic drug having an amount of less than about 1/1,000, or alternatively less than about 1/2,000, 1/5,000, 1/10,000, 1/20,000, 1/50,000, 1/100,000, 1/200,000 or 1/500,000 of the therapeutically effective amount of the drug when used without being packaged into minicells. Pursuant to yet another aspect of the disclosure, the composition can comprise at least about 1 nmol of the chemotherapeutic drug. Accordingly, the disclosure also encompasses embodiments where the amount of the chemotherapeutic drug is at least about 2 nmol, about 3 nmol, about 4 nmol, about 5 nmol, about 10 nmol, about 20 nmol, about 50 nmol, about 100 nmol, or about 800 nmol.

In accordance with the disclosure, a chemotherapeutic drug can be selected from one of the classes detailed below for administration with the encapsulated CD1d-restricted iNKT cell antigens provided herein. In some embodiments, a chemotherapeutic drug is packed into intact, bacterially derived minicells as described herein. These drugs can also be synthetic analogs designed from drug design and discovery efforts. Any known chemotherapy agent can be utilized in the compositions of the invention. Examples of known chemotherapy agents include, but are not limited to:

(1) alkylating agents, such as mustard gas derivatives (Mechlorethamine, Cyclophosphamide (Cytoxan), Chlorambucil (Leukeran), Melphalan, and Ifosfamide), ethylenimines (Thiotepa (Thioplex) and Hexamethylmelamine), alkylsulfonates (Busulfan (Myleran)), hydrazines and triazines (Altretamine (Hexalen), Procarbazine (Matulane), Dacarbazine (DTIC) and Temozolomide), nitrosureas (Carmustine, Lomustine and Streptozocin), and metal salts (Carboplatin, Cisplatin (Platinol), and Oxaliplatin), Mechlorethamine, and Melphalan (Alkeran);

(2) Plant alkaloids, terpenoids and topoisomerase inhibitors, such as vinca alkaloids (Vincristine (Oncovin), Vinblastine (Velban), Vindesine, and Vinorelbine), taxanes (Paclitaxel (Taxol) and Docetaxel (Taxotere)), podophyllotoxins (Etoposide and Tenisopide), and camptothecan analogs (Irinotecan and Topotecan);

(3) antitumor antibiotics, such as anthracyclines (Doxorubicin (Adriamycin, Rubex, Doxil), Daunorubicin, Epirubicin, Mitoxantrone, Idarubicin, Duocarmycin, and Dactinomycin (Cosmegen)), chromomycins (Dactinomycin and Plicamycin (Mithramycin)), and miscellaneous (Mitomycin and Bleomycin (Blenoxane));

(4) antimetabolites, such as folic acid antagonists (Methotrexate), pyrimidine antagonists (5-Fluorouracil, Foxuridine, Cytarabine, Flurouracil (5-FU), Capecitabine, and Gemcitabine), purine antagonists (6-Mercaptopurine (Purinethol) and 6-Thioguanine), 6-Thiopurines, and adenosine deaminase inhibitor (Cladribine (Leustatin), Fludarabine, Nelarabine and Pentostatin), Azacitidine, Thioguanine, and Cytarabine (ara-C);

(5) topoisomerase Inhibitors, such as topoisomerase I inhibitors (Ironotecan, topotecan), and topoisomerase II inhibitors (Amsacrine, etoposide, etoposide phosphate, teniposide);

(6) hormonal agents, exemplified by Estrogen and Androgen Inhibitors (Tamoxifen and Flutamide), Gonadotropin-Releasing Hormone Agonists (Leuprolide and Goserelin (Zoladex)), Aromatase Inhibitors (Aminoglutethimide and Anastrozole (Arimidex));

(7) DNA hypomethylating agents, e.g., Azacitidine, Decitabine;

(8) Poly(adenosine diphosphate [ADP]-ribose) polymerase (PARP) pathway inhibitors, such as Iniparib, Olaparib, Veliparib;

(9) PI3K/Akt/mTOR pathway inhibitors, e.g., Everolimus;

(10) Histone deacetylase (HDAC) inhibitors, e.g., Vorinostat, Entinostat (SNDX-275), Mocetinostat (MGCD0103), Panobinostat (LBH589), Romidepsin, Valproic acid.

(11) Cyclin-dependent kinase (CDK) inhibitors, e.g., Flavopiridol, Olomoucine, Roscovitine, Kenpaullone, AG-024322 (Pfizer), Fascaplysin, Ryuvidine, Purvalanol A, NU2058, BML-259, SU 9516, PD-0332991, P276-00.

(12) Heat shock protein (HSP90) inhibitors, e.g., Geldanamycin, Tanespimycin, Alvespimycin, Radicicol, Deguelin, and BIIB021;

(13) Murine double minute 2 (MDM2) inhibitors, e.g., Cis-imidazoline, Benzodiazepinedione, Spiro-oxindoles, Isoquinolinone, Thiophene, 5-Deazaflavin, Tryptamine;

(14) Anaplastic lymphoma kinase (ALK) inhibitors, e.g., Aminopyridine, Diaminopyrimidine, Pyridoisoquinoline, Pyrrolopyrazole, Indolocarbazole, Pyrrolopyrimidine, Dianilinopyrimidine;

(15) Poly [ADPribose] polymerase (PARP) inhibitors, illustrated by Benzamide, Phthalazinone, Tricyclic indole, Benzimidazole, Indazole, Pyrrolocarbazole, Phthalazinone, Isoindolinone; and

(16) miscellaneous anticancer drugs, exemplified by Amsacrine, Asparaginase (El-spar), Hydroxyurea, Mitoxantrone (Novantrone), Mitotane (Lysodren), Maytansinoid, Retinoic acid Derivatives, Bone Marrow Growth Factors (sargramostim and filgrastim), Amifostine, agents disrupting folate metabolism, e.g., Pemetrexed, ribonucleotide reductase inhibitors (Hydroxyurea), adrenocortical steroid inhibitors (Mitotane), enzymes (Asparaginase and Pegaspargase), antimicrotubule agents (Estramustine), and retinoids (Bexarotene, Isotretinoin, Tretinoin (ATRA)).

Chemotherapy drugs that are illustrative of the small molecule drug subcategory are Actinomycin-D, Alkeran, Ara-C, Anastrozole, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Maytansinoids (molecular weight: ~738 Daltons) are a group of chemical derivatives of maytansine, having potent cytotoxicity. Although considered unsafe for human patient use, due to toxicity concerns, maytansinoids are suitable for delivery to brain tumor patients via minicells, pursuant to the present invention.

Duocarmycins (molecular weight: ~588 Daltons) are a series of related natural products, first isolated from *Streptomyces* bacteria. They also have potent cytotoxicity but are considered as unsafe for human use. Like maytansinoids, duocarmycins are suitable chemotherapy drugs for use in the invention.

The subcategory of biologic chemotherapy drugs includes, without limitation, Asparaginase, AIN-457, Bapineuzumab, Belimumab, Brentuximab, Briakinumab, Canakinumab, Cetuximab, Dalotuzumab, Denosumab, Epratuzumab, Estafenatox, Farletuzumab, Figitumumab, Galiximab, Gemtuzumab, Girentuximab (WX-G250), Herceptin, Ibritumomab, Inotuzumab, Ipilimumab, Mepolizumab, Muromonab-CD3, Naptumomab, Necitumumab, Nimotuzumab, Ocrelizumab, Ofatumumab, Otelixizumab, Ozogamicin, Pagibaximab, Panitumumab, Pertuzumab, Ramucirumab, Reslizumab, Rituximab, REGN88, Solanezumab, Tanezumab, Teplizumab, Tiuxetan, Tositumomab, Trastuzumab, Tremelimumab, Vedolizumab, Zalutumumab, and Zanolimumab.

In some embodiments, the antineoplastic agent comprises a compound selected from the group consisting of actinomycin-D, alkeran, ara-C, anastrozole, BiCNU, bicalutamide, bleomycin, busulfan, capecitabine, carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, steroids, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, VP-16, xeloda, asparaginase, AIN-457, bapineuzumab, belimumab, brentuximab, briakinumab, canakinumab, cetuximab, dalotuzumab, denosumab, epratuzumab, estafenatox, farletuzumab, figitumumab, galiximab, gemtuzumab, girentuximab (WX-G250), herceptin, ibritumomab, inotuzumab, ipilimumab, mepolizumab, muromonab-CD3, naptumomab, necitumumab, nimotuzumab, ocrelizumab, ofatumumab, otelixizumab, ozogamicin, pagibaximab, panitumumab, pertuzumab, ramucirumab, reslizumab, rituximab, REGN88, solanezumab, tanezumab, teplizumab, tiuxetan, tositumomab, trastuzumab, tremelimumab, vedolizumab, zalutumumab, zanolimumab, 5FC, accutane hoffmann-la roche, AEE788 novartis, AMG-102, anti neoplaston, AQ4N (Banoxantrone), AVANDIA (Rosiglitazone Maleate), avastin (Bevacizumab) genetech, BCNU, biCNU carmustine, CCI-779, CCNU, CCNU lomustine, celecoxib (Systemic), chloroquine, cilengitide (EMD 121974), CPT-11 (CAMPTOSAR, Irinotecan), dasatinib (BMS-354825, Sprycel), dendritic cell therapy, etoposide (Eposin, Etopophos, Vepesid), GDC-0449, gleevec (imatinib mesylate), gliadel wafer, hydroxychloroquine, IL-13, IMC-3G3, immune therapy, iressa (ZD-1839), lapatinib (GW572016), methotrexate for cancer (Systemic), novocure, OSI-774, PCV, RAD001 novartis (mTOR inhibitor), rapamycin (Rapamune, Sirolimus), RMP-7, RTA 744, simvastatin, sirolimus, sorafenib, SU-101, SU5416 sugen, sulfasalazine (Azulfidine), sutent (Pfizer), TARCEVA (erlotinib HCl), taxol, TEMODAR schering-plough, TGF-B anti-sense, thalomid (thalidomide), topotecan (Systemic), VEGF trap, VEGF-trap, vorinostat (SAHA), XL 765, XL184, XL765, zarnestra (tipifarnib), ZOCOR (simvastatin), cyclophosphamide (Cytoxan), (Alkeran), chlorambucil (Leukeran), thiopeta (Thioplex), busulfan (Myleran), procarbazine (Matulane), dacarbazine (DTIC), altretamine (Hexalen), clorambucil, cisplatin (Platinol), ifosafamide, methotrexate (MTX), 6-thiopurines (Mercaptopurine [6-MP], Thioguanine [6-TG]), mercaptopurine (Purinethol), fludarabine phosphate, (Leustatin), flurouracil (5-FU), cytarabine (ara-C), azacitidine, vinblastine (Velban), vincristine (Oncovin), podophyllotoxins (etoposide {VP-16} and teniposide {VM-26}), camptothecins (topotecan and irinotecan), taxanes such as paclitaxel (Taxol) and docetaxel (Taxotere), (Adriamycin, Rubex, Doxil), dactinomycin (Cosmegen), plicamycin (Mithramycin), mitomycin: (Mutamycin), bleomycin (Blenoxane), estrogen and androgen inhibitors (Tamoxifen), gonadotropin-releasing hormone agonists (Leuprolide and Goserelin (Zoladex)), aromatase inhibitors (Aminoglutethimide and Anastrozole (Arimidex)), amsacrine, asparaginase (El-spar), mitoxantrone (Novantrone), mitotane (Lysodren), retinoic acid derivatives, bone marrow growth factors (sargramostim and filgrastim), amifostine, pemetrexed, decitabine, iniparib, olaparib, veliparib, everolimus, vorinostat, entinostat (SNDX-275), mocetinostat (MGCD0103), panobinostat (LBH589), romidepsin, valproic acid, flavopiridol, olomoucine, roscovitine, kenpaullone, AG-024322 (Pfizer), fascaplysin, ryuvidine, purvalanol A, NU2058, BML-259, SU 9516, PD-0332991, P276-00, geldanamycin, tanespimycin, alvespimycin, radicicol, deguelin, BIIB021, cis-imidazoline, benzodiazepinedione, spiro-oxindoles, isoquinolinone, thiophene, 5-deazaflavin, tryptamine, aminopyridine, diaminopyrimidine, pyridoisoquinoline, pyrrolopyrazole, indolocarbazole, pyrrolopyrimidine, dianilinopyrimidine, benzamide, phthalazinone, tricyclic indole, benzimidazole, indazole, pyrrolocarbazole, isoindolinone, morpholinyl anthracycline, a maytansinoid, ducarmycin, auristatins, calicheamicins (DNA damaging agents), α-amanitin (RNA polymerase II inhibitor), centanamycin, pyrrolobenzodiazepine, streptonigtin, nitrogen mustards, nitrosorueas, alkane sulfonates, pyrimidine analogs, purine analogs, antimetabolites, folate analogs, anthracyclines, taxanes, vinca alkaloids, topoisomerase inhibitors, hormonal agents, and any combination thereof.

Active agents useable in accordance with the present disclosure are not limited to those drug classes or particular agents enumerated above. Different discovery platforms continue to yield new agents that are directed at unique molecular signatures of cancer cells; indeed, thousands of such chemical and biological drugs have been discovered, only some of which are listed here. Yet, the surprising capability of intact, bacterially derived minicells and killed bacterial cells to accommodate packaging of a diverse variety of active agents, hydrophilic or hydrophobic, means that essentially any such drug, when packaged in minicells, has the potential to treat a cancer, pursuant to the findings in the present disclosure.

Illustrative of the class of antineoplastic agents are radionuclides, chemotherapy drugs, and functional nucleic acids, including but not limited to regulatory RNAs. Members of the class are discussed further below.

1. Radionuclides

In some embodiments, the encapsulated CD1d-restricted iNKT cell antigens are administered in combination with an antineoplastic agent that is a radionuclide. A "radionuclide" is an atom with an unstable nucleus, i.e., one characterized by excess energy available to be imparted either to a newly created radiation particle within the nucleus or to an atomic electron. Radionuclides herein may also be referred to as "radioisotopes," "radioimaging agents," or "radiolabels." Radionuclides can be used imaging and/or therapeutic purposes. In some embodiments, the radionuclide is administered using an intact, bacterially derived minicell. They can be contained within the minicell or attached to a ligand, peptide, or glycolipid on the outer surface of a minicell described herein. Attachments may be directly or via a linker, a linker containing a chelating moiety comprising chelators such as mercaptoacetyltriglycine (MAG3), DOTA, EDTA, HYNIC, DTPA or crown ethers may be used. The chelators may be attached directly the minicell surface component or attached to the minicell via a linker. Numerous radionuclides are known in the art, and a number of them are known to be suitable for medical use, such as yttrium-90, technetium-99m, iodine-123, iodine-124, iodine-125, iodine-131, rubidium-82, thallium-201, gallium-67, fluorine-18, xenon-133, and indium-111.

Thus, in some embodiments, the radioisotope comprises a radioisotope selected from the group consisting of yttrium-90, yttrium-86, terbium-152, terbium-155, terbium-149, terbium-161, technetium-99m, iodine-123, iodine-131, rubidium-82, thallium-201, gallium-67, fluorine-18, copper-64, gallium-68, xenon-133, indium-111, lutetium-177, and any combination thereof.

Radioisotopes useful for attaching to minicells for both imaging and therapeutic purposes include, for example, Iodine-131 and lutetium-177, which are gamma and beta emitters. Thus, these agents can be used for both imaging and therapy.

Different isotopes of the same element, for example, iodine-123 (gamma emitter) and iodine-131 (gamma and beta emitters), can also be used for both imaging and therapeutic purposes (Gerard and Cavalieri, 2002; Alzahrani et al., 2012).

Newer examples are yttrium-86/yttrium-90 or terbium isotopes (Tb): $^{152}$Tb (beta plus emitter), $^{155}$Tb (gamma emitter), $^{149}$Tb (alpha emitter), and $^{161}$Tb (beta minus particle) (Müller et al., 2012; Walrand et al., 2015).

Nuclear imaging utilizes gamma and positron emitters (β+). Gamma emitters, such as technetium-99m ($^{99m}$Tc) or iodine-123 ($^{123}$I), can be located using gamma cameras (planar imaging) or SPECT (single photon emission computed tomography) (Holman and Tumeh, 1990).

The tissue penetration of these particles is proportional to the energy of the radioisotopes (Kramer-Marek and Capala, 2012). Beta particles have a potential cytocidal effect, but they also spare the surrounding healthy tissue due to having a tissue penetration of only a few millimeters. Commonly used beta emitters in routine nuclear oncology practices include lutetium-177 ($^{177}$Lu, tissue penetration: 0.5-0.6 mm, maximum: 2 mm, 497 keV, half-life: 6.7 days) and yttrium-90 ($^{90}$Y, tissue penetration: mean 2.5 mm, maximum: 11 mm, 935 keV, half-life: 64 hours) (Teunissen et al., 2005; Kwekkeboom et al., 2008; Ahmadzadehfar et al., 2010; Pillai et al., 2013; Ahmadzadehfar et al., 2016).

Radionuclides have found extensive use in nuclear medicine, particularly as beta-ray emitters for damaging tumor cells. In some embodiments, radionuclides are suitably employed as the antineoplastic agents.

Radionuclides can be associated with intact, bacterially derived minicells by any known technique. Thus, a protein or other minicell-surface moiety (see below) can be labeled with a radionuclide, using a commercially available labeling means, such as use of Pierce Iodination reagent, a product of Pierce Biotechnology Inc. (Rockford, Ill.), detailed in Rice et al., Semin. Nucl. Med., 41, 265-282 (2011). Alternatively, radionuclides can be incorporated into proteins that are inside minicells.

In the latter situation, a minicell-producing bacterial strain is transformed with plasmid DNA encoding foreign protein. When minicells are formed during asymmetric cell division, several copies of the plasmid DNA segregate into the minicell cytoplasm. The resultant recombinant minicells are incubated in the presence of radiolabeled amino acids under conditions such that foreign protein expressed inside the minicell, from the plasmid DNA, incorporates into the radionuclide-carrying amino acids. Pursuant to the protocol of Clark-Curtiss and Curtiss, Methods Enzymol., 101: 347-362 (1983), for instance, recombinant minicells are incubated in minimal growth medium that contains $^{35S}$methionine, whereby newly expressed, plasmid-encoded proteins incorporate the $^{35S}$methionine. A similar approach can be used so that recombinant minicells become packaged with other radiolabels, as desired.

Oligosaccharides on the minicell surface also can be radiolabeled using, for example, well-established protocols described by Fukuda, Curr. Protocols Molec. Biol. (Suppl. 26), 17.5.1-17.5.8 (1994). Illustrative of such oligosaccharides that are endemic to minicells is the O-polysaccharide component of the lipopolysaccharide (LPS) found on the surface of minicells derived from Gram-negative bacteria (see below).

A preferred methodology in this regard is to radiolabel a bispecific antibody used as a tumor targeting ligand that is used to target minicells to specific tumors. See US Patent Publication 2007/0237744, the contents of which are incorporated herein by reference. That is, the bispecific antibody "coated" on a minicell exposes a significant amount of additional surface protein for radiolabeling. Accordingly, it is possible to achieve a higher specific activity of the radiolabel associated with the antibody-coated minicell. By contrast, the radiolabeling of non-coated minicells, i.e., when the radionuclide labels only endemic moieties, can result in weaker labeling (lower specific activity). In one embodiment, this weaker labeling is thought to occur because the outer membrane-associated proteins of minicells derived from Gram-negative bacteria are masked by LPS, which, as further discussed below, comprises long chains of O-polysaccharide covering the minicell surface.

For treating a tumor, a composition of the disclosure would be delivered in a dose or in multiple doses that affords a level of in-tumor irradiation that is sufficient at least to reduce tumor mass, if not eliminate the tumor altogether. The progress of treatment can be monitored along this line, on a case-by-case basis. In general terms, however, the amount of radioactivity packaged in the composition typically will be on the order of about 30 to about 50 Gy, although the invention also contemplates a higher amount of radioactivity, such as for example about 50 to about 200 Gy, which gives an overall range between about 30 Gy and about 200 Gy.

In some instances, the amount of radioactivity packaged in the composition can be even lower than mentioned above, given the highly efficient and specific delivery of the minicell-borne radionuclides to a tumor. Accordingly, in one aspect the composition comprises from about 20 to about 40 Gy, or about 10 to about 30 Gy, or about 1 to about 20 Gy, or less than about 10 Gy.

Some tumor targeting ligands may include a radioisotope that functions to deliver radiation to the tumor while the ligand binds the tumor cell. In some embodiments, the ligand comprises Arg-Gly-Asp (RGD) peptide, bombesin (BBN)/gastrin-releasing peptide (GRP), cholecystokinin (CCK)/gastrin peptide, α-melanocyte-stimulating hormone (α-MSH), neuropeptide Y (NPY), neurotensin (NT), [$^{68}$Ga] Ga-PSMA-HBED-CC ([$^{68}$Ga]Ga-PSMA-11 [PET]), [$^{177}$Lu] Lu/[$^{90}$Y]Y-J591, [$^{123}$I]I-MIP-1072, [$^{131}$I]I-MIP-1095, $^{68}$Ga or $^{177}$Lu labeled PSMA-I&T, $^{68}$Ga or $^{177}$Lu labeled DKFZ-PSMA-617 (PSMA-617), somatostatin (SST) peptide, substance P, T140, tumor molecular targeted peptide 1 (TMTP1), vasoactive intestinal peptide (VIP), or any combination thereof.

In some embodiments, the radioisotope is conjugated to the tumor targeting ligand. In some embodiments, the conjugation is via a linker. In some embodiments, the tumor targeting ligand comprises a peptide comprising functional group(s) for conjugation of a radioisotope or chelator moiety that chelates a radioisotope. The functional groups of peptides available for conjugation include but are not limited to the ε-amino group on lysine side chains, the guanidinium group on arginine side chains, the carboxyl groups on aspartic acid or glutamic acid, the cysteine thiol, and the phenol on tyrosine. The most common conjugation reactions are carbodiimide/N-hydroxysuccinimidyl (EDC/NHS) mediated carboxyl and amine coupling, maleimide conjugation to thiol groups, and diazonium modification of the phenol on tyrosine. The representative chemistries to couple peptides with imaging moieties can be found in a number of reviews (Erathodiyil and Ying, 2011; Takahashi et al., 2008).

In some embodiments, the radioisotope functions as a radioimaging agent. Several radioisotopes have been used for peptide labeling including $^{99m}$Tc, $^{123}$I, and $^{111}$In for SPECT imaging and $^{18}$F, $^{64}$Cu and $^{68}$Ga for PET imaging (Chatalic et al., 2015). Generally, these radioisotopes are attached to the peptides via chelators. Some widely-used chelators are described in (Sun et al., 2017). Most therapeutic radiopharmaceuticals are labeled with beta-emitting isotopes (β−).

The minicells of the present invention, targeted to the tumor cells will also deliver targeted radiation from the radioisotope to the tumor cell to which the minicell is bound. In some embodiments, the radioisotope functions as a therapeutic radiation emitting agent, and wherein the amount of radiation provided by the radioisotope is sufficient to provide a therapeutic effect on the tumor. In some embodiments, the therapeutic effect is a reduction in tumor size. The tumor may be reduced in size by about 100%, about 90%, about 80%, about 70%, about 60%, about 50%, about 40%, about 30%, about 20%, about 10%, or about 5%.

Radiolabeled phosphonates have a high bone affinity and can be used for imaging and palliation of painful bone metastases. Depending on the degree of osseous metabolism, the tracer accumulates via adhesion to bones and, preferably, to osteoblastic bone metastases. Therapy planning requires a bone scintigraphy with technetium-99m-hydroxyethylidene diphosphonate (HEDP) to estimate the metabolism and the extent of the metastasis involvement. Bisphosphonate HEDP can be labeled for therapy either with rhenium-186 (beta-emitter, half-life: 89 hours, 1.1 MeV maximal energy, maximal range: 4.6 mm) or rhenium-188 (beta-emitter [to 85%, 2.1 MeV] and gamma-emitter [to 15%, 155 keV], half-life: 16.8 hours, maximal range in soft tissue: 10 mm) (Palmedo, 2007). New promising radiopharmaceuticals for bone palliation therapy include radiolabeled complexes of zoledronic acid. Zoledronic acid belongs to a new, most potent generation of bisphosphonates with cyclic side chains. The bone affinity of zoledronic acid labeled with scandium-46 or lutetium-177 has shown excellent absorption (98% for [177Lu]Lu-zoledronate and 82% for [46Sc] Sc-zoledronate), which is much higher than of bisphosphonates labeled with samarium-153 (maximum: 67%) (Majkowska et al., 2009). These bisphosphonates can be conjugated to intact minicells for use as diagnostics or treatment for bone metastasis.

2. Chemotherapy Drugs

In some embodiments, the encapsulated CD1d-restricted iNKT cell antigens are administered in combination with an antineoplastic agent that is a chemotherapy drug. In this description, "chemotherapeutic drug," "chemotherapeutic agent," and "chemotherapy" are employed interchangeably to connote a drug that has the ability to kill or disrupt a neoplastic cell. A chemotherapeutic agent can be a small molecule drug or a biologic drug, as further detailed below. In some embodiments, the chemotherapy drug is administered using an intact, bacterially derived minicell.

The "small molecule drug" subcategory encompasses compounds characterized by having (i) an effect on a biological process and (ii) a low molecular weight as compared to a protein or polymeric macromolecule. Small molecule drugs typically are about 800 Daltons or less, with a lower limit of about 150 Daltons, as illustrated by Temodar® (temozolomide), at about 194 Daltons, which is used to treat glioblastoma and other types of brain cancer. In this context "about" indicates that the qualified molecular-weight value is subject to variances in measurement precision and to experimental error on the order of several Daltons or tens of Daltons. Thus, a small molecule drug can have a molecular weight of about 900 Daltons or less, about 800 or less, about 700 or less, about 600 or less, about 500 or less, or about 400 Daltons or less, e.g., in the range of about 150 to about 400 Daltons. More specifically, a small molecule drug can have a molecular weight of about 400 Daltons or more, about 450 Daltons or more, about 500 Daltons or more, about 550 Daltons or more, about 600 Daltons or more, about 650 Daltons or more, about 700 Daltons or more, or about 750 Daltons or more. In another embodiment, the small molecule drug packaged into the minicells has a molecular weight between about 400 and about 900 Daltons, between about 450 and about 900 Daltons, between about 450 and about 850 Daltons, between about 450 and about 800 Daltons, between about 500 and about 800 Daltons, or between about 550 and about 750 Daltons.

Specifically, suitable small molecule drugs include but are not limited to those listed above, such as nitrogen mustards, nitrosorueas, ethyleneimine, alkane sulfonates, tetrazine, platinum compounds, pyrimidine analogs, purine analogs, anti-metabolites, folate analogs, anthracyclines, taxanes, vinca alkaloids, and topoisomerase inhibitors, inter alia. Accordingly, a small molecule drug for use in the present invention can be selected from among any of the following, inter alia: enediynes, such as dynemicin A, unicalamycin, calicheamicin γ1 and calicheamicin-theta-1; meayamicin, a synthetic analog of FR901464; benzosuberene derivatives as described, for example, by Tanpure et al., *Bioorg. Med. Chem.*, 21: 8019-32 (2013); auristatins, such as auristatin E, mono-methyl auristatin E (MMAE), and auristatin F, which are synthetic analogs of dolastatin; duocarmysins such as duocarmycin SA and CC-1065; maytansine and its derivatives (maytansinoids), such as DM1 and DM4; irinotecan (Camptosar®) and other topoisomerase inhibitors, such as topotecan, etoposide, mitoxantrone and teniposide; and yatakemycin, the synthesis of which is detailed by Okano et al., 2006.

More particularly, any one or more or all of the specific small molecule drugs detailed herein are illustrative of those suitable for use in this invention: actinomycin-D, alkeran, ara-C, anastrozole, BiCNU, bicalutamide, bisantrene, bleomycin, busulfan, capecitabine (Xeloda®), carboplatin, carboplatinum, carmustine, CCNU, chlorambucil, cisplatin, cladribine, CPT-11, cyclophosphamide, cytarabine, cytosine arabinoside, cytoxan, dacarbazine, dactinomycin, daunorubicin, dexrazoxane, docetaxel, doxorubicin, DTIC, epirubicin, ethyleneimine, etoposide, floxuridine, fludarabine, fluorouracil, flutamide, fotemustine, gemcitabine, hexamethylamine, hydroxyurea, idarubicin, ifosfamide, irinotecan, lomustine, mechlorethamine, melphalan, mercaptopurine, methotrexate, mitomycin, mitotane, mitoxantrone, oxaliplatin, paclitaxel, pamidronate, pentostatin, plicamycin, procarbazine, streptozocin, STI-571, tamoxifen, temozolomide, teniposide, tetrazine, thioguanine, thiotepa, tomudex, topotecan, treosulphan, trimetrexate, vinblastine, vincristine, vindesine, vinorelbine, and VP-16.

For purposes of this description a "biologic drug" is defined, by contrast, to denote any biologically active macromolecule that can be created by a biological process, exclusive of "functional nucleic acids," discussed below, and polypeptides that by size qualify as small molecule drugs, as defined above. The "biologic drug" subcategory thus is exclusive of and does not overlap with the small molecule drug and functional nucleic acid subcategories. Illustrative of biologic drugs are therapeutic proteins and antibodies, whether natural or recombinant or synthetically made, e.g., using the tools of medicinal chemistry and drug design.

3. Supertoxic Chemotherapy Drugs

Certain molecules that are designed for chemotherapeutic purposes fail during pre-clinical or clinical trials due to unacceptable toxicity. The present inventors have shown that packaging a highly toxic or "supertoxic" chemotherapy drug in a minicell, followed by systemic delivery to a tumor patient, results in delivery of the drug to tumor cells. Further, even after the tumor cells are broken up and the drug-containing cytoplasm is released to the nearby normal tissue, the result is not toxicity to normal tissue. This is because the drug is already bound to the tumor cellular structures, such as DNA, and can no longer attack normal cells. Accordingly, the present invention is particularly useful for delivery of highly toxic ("supertoxic") chemotherapy drugs to a cancer patient. Thus, in some embodiments, the encapsulated CD1d-restricted iNKT cell antigens are administered in combination with an antineoplastic agent that is a supertoxic chemotherapy drug. In some embodiments, the supertoxic chemotherapy drug is administered using an intact, bacterially derived minicell described herein.

When cancer subjects have exhausted all treatment options, the tumors are likely to have reached a stage of considerable heterogeneity with a high degree of resistance to conventional cytotoxic drugs. "Highly toxic chemotherapy drug" or "supertoxic chemotherapy drugs" in this description refer to chemotherapy drugs that can overcome the resistance to conventional drugs due to their relatively low lethal dose to normal cells as compared to their effective dose for cancer cells.

Thus, in one aspect a highly toxic chemotherapy drug has a median lethal dose ($LD_{50}$) that is lower than its median effective dose ($ED_{50}$) for a targeted cancer. For instance, a highly toxic or supertoxic chemotherapy drug can have an $LD_{50}$ that is lower than about 500%, about 400%, about 300%, about 250%, about 200%, about 150%, about 120%, or about 100% of the $ED_{50}$ of the drug for a targeted cancer. In another aspect, a highly toxic or supertoxic chemotherapy drug has a maximum sub-lethal dose (i.e., the highest dose that does not cause serious or irreversible toxicity) that is lower than its minimum effective dose, e.g., about 500%, about 400%, about 300%, about 250%, about 200%, about 150%, about 120%, about 100%, about 90%, about 80%, about 70%, about 60% or about 50% of the minimum effective dose. In one embodiment, the targeted cancer can be, for example, (1) a cancer type for which the drug is designed, (2) the first cancer type in which a pre-clinical or clinical trial is run for that drug, or (3) a cancer type in which the drug shows the highest efficacy among all tested cancers.

Illustrative, non-limiting examples of supertoxic chemotherapy drugs include but are not limited to maytansinoids, duocarmycins, morpholinyl anthracycline, and their derivatives. Maytansinoids (molecular weight: about 738 Daltons) are a group of chemical derivatives of maytansine, having potent cytotoxicity. Although considered unsafe for human patient use, due to toxicity concerns, maytansinoids are suitable for delivery to tumor patients via minicells, pursuant to the present invention. Duocarmycins (molecular weight: about 588 Daltons) are a series of related natural products, first isolated from *Streptomyces* bacteria. They also have potent cytotoxicity but are considered as unsafe for human use. Like maytansinoids, duocarmycins are suitable chemotherapy drugs for use in the invention.

Illustrative as well are compounds in the class of morpholinyl anthracycline derivatives described in international patent application WO 1998/002446. Among such derivatives are nemorubicin (3'-deamino-3'-[2(S)-methoxy-4-morpholinyl]doxorubicin) (MMDX), and its major metabolite PNU-159682 (3'-deamino-3"-4'-anhydro-[2"(S)-methoxy-3"(R)-hydroxy-4"-morpholinyl-] doxorubicin), as well as four other such derivatives described in U.S. Pat. No. 8,470,984, the contents of which are incorporated here by reference: 3'-deamino-3"-4'-anhydro-[2"(S)-methoxy-3"(R)-hydroxy-4"-morpholinyl]-idarubicin; 3'-deamino-3"-4'-anhydro-[2"(S)-methoxy-3"(R)-hydroxy-4"-morpholinyl]-daunorubicin; 3'-deamino-3"-4'-anhydro-[2"(S)-methoxy-3"(R)-hydroxy-4"-morpholinyl]-caminomycin; and 3'-deamino-3"-4'-anhydro-[2"(S)-ethoxy-3"(R)-hydroxy-4"-morpholinyl]d-oxorubicin.

In an exemplary embodiment of the present disclosure, the minicell comprises the supertoxic chemotherapy drug 3'-deamino-3",4'-anhydro-[2"(S)-methoxy-3"(R)-oxy-4"-morpholinyl] doxorubicin (PNU-159682). The present inventors discovered that PNU-159682 is a potent drug that appears to overcome drug resistance in a number of different tumor cell lines and is much more potent than a range of conventional chemotherapeutics in cytotoxicity assays against many different tumor cell lines. See Examples 8 and 9. Further, it was shown in in vivo mouse xenograft experiments that human tumor xenografts resistant to doxorubicin can be treated effectively with IV administration of EGFR-targeted and PNU-159682-loaded EDVs. See Example 11. Remarkably, PNU-159682-loaded EDVs combined with type I interferon agonists was found to be well-tolerated and to provide synergistic and improved anti-cancer effect in a late-stage pancreatic cancer patient. See Example 12. Accordingly, in one embodiment of the present invention a composition comprises an EGFR-targeted minicell comprising PNU-159682 as an active anticancer drug.

Other suitable cancer chemotherapy drugs that may exhibit supertoxic chemotherapy properties include auristatins, calicheamicins (DNA damaging agents), α-amanitin (RNA polymerase II inhibitor), centanamycin, geldanamycin, pyrrolobenzodiazepine, streptonigtin, nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors, and hormonal agents, inter alia.

4. Biologic Chemotherapy Drugs

In some embodiments, the encapsulated CD1d-restricted iNKT cell antigens are administered in combination with an antineoplastic agent that is a biologic chemotherapy drug. Examples of such drugs include but are not limited to asparaginase, AIN-457, bapineuzumab, belimumab, brentuximab, briakinumab, canakinumab, cetuximab, dalotuzumab, denosumab, epratuzumab, estafenatox, farletuzumab, figitumumab, galiximab, gemtuzumab, girentuximab (WX-G250), ibritumomab, inotuzumab, ipilimumab, mepolizumab, muromonab-CD3, naptumomab, necitumumab, nimotuzumab, ocrelizumab, ofatumumab, otelixizumab, ozogamicin, pagibaximab, panitumumab, pertuzumab, ramucirumab, reslizumab, rituximab, REGN88, solanezumab, tanezumab, teplizumab, tiuxetan, tositumomab, trastuzumab (Herceptin®), tremelimumab, vedolizumab, zalutumumab, and zanolimumab. In some embodiments, the biologic chemotherapy drug is administered using an intact, bacterially derived minicell.

5. Functional Nucleic Acids

In some embodiments, the encapsulated CD1d-restricted iNKT cell antigens are administered in combination with a functional nucleic acid. "Functional nucleic acid" refers to a nucleic acid molecule that, upon introduction into a host cell, specifically interferes with expression of a protein. In some embodiments, the functional nucleic acid is administered using an intact, bacterially derived minicell. With respect to treating cancer, it is preferable that a functional nucleic acid payload delivered to cancer cells via intact, bacterially derived minicells inhibits a gene that promotes tumor cell proliferation, angiogenesis or resistance to chemotherapy and/or that inhibits apoptosis or cell-cycle arrest; i.e., a "cancer-promoting gene."

In general, functional nucleic acid molecules used in this disclosure have the capacity to reduce expression of a protein by interacting with a transcript for a protein. This category of minicell payload for the disclosure includes regulatory RNAs, such as siRNA, shRNA, short RNAs (typically less than 400 bases in length), micro-RNAs (miRNAs), ribozymes and decoy RNA, antisense nucleic acids, and LincRNA, inter alia. In this regard, "ribozyme" refers to an RNA molecule having an enzymatic activity that can repeatedly cleave other RNA molecules in a nucleotide base sequence-specific manner. "Antisense oligonucleotide" denotes a nucleic acid molecule that is complementary to a portion of a particular gene transcript, such that the molecule can hybridize to the transcript and block its translation. An antisense oligonucleotide can comprise RNA or DNA. The "LincRNA" or "long intergenic non-coding RNA" rubric encompasses non-protein coding transcripts longer than 200 nucleotides. LincRNAs can regulate the transcription, splicing, and/or translation of genes, as discussed by Khalil et al., 2009.

Each of the types of regulatory RNA can be the source of functional nucleic acid molecule that inhibits a tumor-promoting gene as described above and, hence, that is suitable for use according to the present disclosure. Thus, in one embodiment of the disclosure the intact minicells carry siRNA molecules mediating a post-transcriptional, gene-silencing RNA interference (RNAi) mechanism, which can be exploited to target tumor-promoting genes. For example, see MacDiarmid et al., 2009 (antibody-presenting minicells deliver, with chemotherapy drug, siRNAs that counter developing resistance to drug), and Oh and Park, *Advanced Drug Delivery Rev.*, 61: 850-62 (2009) (delivery of therapeutic siRNAs to treat breast, ovarian, cervical, liver, lung and prostate cancer, respectively).

As noted, "siRNA" generally refers to double-stranded RNA molecules from about 10 to about 30 nucleotides long that are named for their ability specifically to interfere with protein expression. Preferably, siRNA molecules are about 12 to about 28 nucleotides long, more preferably about 15 to about 25 nucleotides long, still more preferably about 19 to about 23 nucleotides long and most preferably about 21 to about 23 nucleotides long. Therefore, siRNA molecules can be, for example, about 12, about 13, about 14, about 15, about 16, about 17, about 18, about 19, about 20, about 21, about 22, about 23, about 24, about 25, about 26, about 27, about 28, or about 29 nucleotides in length.

The length of one strand designates the length of an siRNA molecule. For instance, an siRNA that is described as 21 ribonucleotides long (a 21-mer) could comprise two opposing strands of RNA that anneal for 19 contiguous base pairings. The two remaining ribonucleotides on each strand would form an "overhang." When a siRNA contains two strands of different lengths, the longer of the strands designates the length of the siRNA. For instance, a dsRNA containing one strand that is 21 nucleotides long and a second strand that is 20 nucleotides long, constitutes a 21-mer.

Tools to assist the design of siRNA specifically and regulatory RNA generally are readily available. For instance, a computer-based siRNA design tool is available on the internet at www.dharmacon.com.

In another preferred embodiment, the intact minicells of the present disclosure carry miRNAs, which, like siRNA, are capable of mediating a post-transcriptional, gene-silencing RNA interference (RNAi) mechanism. Also, like siRNA, the gene-silencing effect mediated by miRNA can be exploited to target tumor-promoting genes. For example, see Kota et al., 2009 (delivery of a miRNA via transfection resulted in inhibition of cancer cell proliferation, tumor-specific apoptosis and dramatic protection from disease progression without toxicity in murine liver cancer model), and Takeshita et al., 2010 (delivery of synthetic miRNA via transient transfection inhibited growth of metastatic prostate tumor cells on bone tissues).

Although both mediate RNA interference, miRNA and siRNA have noted differences. In this regard, "miRNA" generally refers to a class of about 17 to about 27-nucleotide single-stranded RNA molecules (instead of double-stranded as in the case of siRNA). Therefore, miRNA molecules can be, for example, about 17, about 18, about 19, about 20, about 21, about 22, about 23, about 24, about 25, about 26, or about 27 nucleotides in length. Preferably, miRNA molecules are about 21 to about 25 nucleotide long.

Another difference between miRNAs and siRNAs is that the former generally do not fully complement the mRNA target. In contrast, siRNA must be completely complementary to the mRNA target. Consequently, siRNA generally results in silencing of a single, specific target, while miRNA is promiscuous.

Additionally, although both are assembled into RISC (RNA-induced silencing complex), siRNA and miRNA differ in their respective initial processing before RISC assembly. These differences are described in detail in Chu et al., 2006; and Gregory et al., 2006. A number of databases serve as miRNA depositories. For example, see miRBase (www.mirbase.org) and tarbase (http://diana.cslab.ece.ntua.gr/DianaToolsNew/index.php?r=tarbase/index). In conventional usage, miRNAs typically are named with the prefix "-mir," combined with a sequential number. For instance, a new miRNA discovered after mouse mir-352 will be named mouse "mir-353." Again, tools to assist the design of regulatory RNA including miRNA are readily available. In this regard, a computer-based miRNA design tool is available on the internet at wmd2.weigelworld.org/cgi-bin/mirnatools.pl.

It is a discovery of the present inventors that miRNA16a can be administered by targeted minicell-mediated delivery to mesothelioma and Adreno-Cortical cancer cells. See Example 7. Once internalized by the cancer cells, the miRNA16a was found to potently inhibit cancer cell proliferation. Accordingly, in some embodiments the minicells of the present disclosure comprise miRNA16a. Other microRNAs useful in inhibiting the proliferation of neoplastic cells include mir-34 family and let-7 family.

As noted above, a functional nucleic acid employed in the compositions of the invention can inhibit a gene that promotes tumor cell proliferation, angiogenesis or resistance to chemotherapy. The inhibited gene also can itself inhibit apoptosis or cell cycle arrest. Examples of genes that can be targeted by a functional nucleic acid are provided below.

Functional nucleic acids of the disclosure preferably target the gene or transcript of a protein that promotes drug resistance, inhibits apoptosis or promotes a neoplastic phenotype. Successful application of functional nucleic acid strategies in these contexts have been achieved in the art, but without the benefits of minicell vectors. See, e.g., Sioud, *Trends Pharmacol. Sci.*, 2004; Caplen, *Expert Opin. Biol. Ther.*, 2003; Nieth et al., 2003; Caplen and Mousses, 2003; Duxbury et al., 2004; Yague et al, 2004; and Duan et al., 2004.

Proteins that contribute to drug resistance constitute preferred targets of functional nucleic acids. The proteins may contribute to acquired drug resistance or intrinsic drug resistance. When diseased cells, such as tumor cells, initially respond to drugs, but become refractory on subsequent treatment cycles, the resistant phenotype is acquired. Useful targets involved in acquired drug resistance include ATP binding cassette transporters such as P-glycoprotein (P-gp, P-170, PGY1, MDR1, ABCB1, MDR-associated protein, Multidrug resistance protein 1), MDR-2 and MDR-3. MRP2 (multi-drug resistance associated protein), BCR-ABL (breakpoint cluster region—Abelson protooncogene), a STI-571 resistance-associated protein, lung resistance-related protein, cyclooxygenase-2, nuclear factor kappa, XRCC1 (X-ray cross-complementing group 1), ERCC1 (excision cross-complementing gene), GSTP1 (glutathione S-transferase), mutant β-tubulin, and growth factors such as IL-6 are additional targets involved in acquired drug resistance.

Particularly useful targets that contribute to drug resistance include ATP binding cassette transporters such as P-glycoprotein, MDR-2, MDR-3, BCRP, APT11a, and LRP. Useful targets also include proteins that promote apoptosis resistance. These include Bcl-2 (B cell leukemia/lymphoma), Bcl-$X_L$, A1/Bfl 1, focal adhesion kinase, dihydrodiol dehydrogenase, and p53 mutant protein.

Useful targets further include oncogenic and mutant tumor suppressor proteins. Illustrative of these are beta.-Catenin, PKC-α (protein kinase C), C-RAF, K-Ras (V12), DP97 Dead box RNA helicase, DNMT1 (DNA methyltransferase 1), FLIP (Flice-like inhibitory protein), C-Sfc, 53BPI, Polycomb group protein EZH2 (Enhancer of zeste homologue), ErbB1, HPV-16 E5 and E7 (human papillomavirus early 5 and early 7), Fortilin & MCI1P (Myeloid cell leukemia 1 protein), DIP13α (DDC interacting protein 13a), MBD2 (Methyl CpG binding domain), p21, KLF4 (Kruppel-like factor 4), tpt/TCTP (Translational controlled tumor protein), SPK1 and SPK2 (Sphingosine kinase), P300, PLK1 (Polo-like kinase-1), Trp53, Ras, ErbB1, VEGF (Vascular endothelial growth factor), BAG-1 (BCL2-associated athanogene 1), MRP2, BCR-ABL, STI-571 resistance-associated protein, lung resistance-related protein, cyclooxygenase-2, nuclear factor kappa, XRCC1, ERCC1, GSTP1, mutant—β-tubulin, and growth factors.

Also useful as targets are global regulatory elements exemplified by the cytoplasmic polyadenylation element binding proteins (CEPBs). For instance, CEPB4 is overexpressed in glioblastoma and pancreatic cancers, where the protein activates hundreds of genes associated with tumor growth, and it is not detected in healthy cells (Oritz-Zapater et al, 2011). In accordance with the present description, therefore, treatment of a glioblastoma could be effected via administration of a composition containing intact, bacterially derived minicells that encompass an agent that counters overexpression of CEPB4, such as an siRNA or other functional nucleic acid molecule that disrupts CEPB4 expression by the tumor cells.

A further example of useful targets for functional nucleic acids include replication protein A (RPA), a trimeric complex composed of 70-kDa (RPA1), 32-kDa (RPA2), and 14-kDa (RPA3) subunits, which is essential for DNA replication in all organisms. Iftode et al., 1999.

Other useful targets are those important for mitosis and for the maintenance of genomic stability. Examples include the Polo-like kinase (PLK1), which is overexpressed in a broad range of cancer cells. The inventors of the present disclosure also found that siRNA inhibiting Plk1 (siPlk1) expression inhibits proliferation of mesothelioma and Adreno-Cortical cancer cells. Accordingly, in some embodiments, the minicells of the present disclosure comprise Plk1.

Other useful targets are those that are involved in DNA replication and repair. Examples include ribonucleotide reductase (RR), which is a potential therapeutic target for cancer because it catalyzes the conversion of ribonucleoside 5'-diphosphates into their corresponding 2'-deoxyribonucleoside 5'-triphosphates that are necessary for DNA replication and repair. See D'Angiolella et al., 2012. Human RR comprises two subunits, RRM1 and RRM2, and functional nucleic acids that target both subunits are useful in the present invention. The inventors of the present disclosure showed that siRNA targeting RRM1 (siRRM1) potently inhibited mesothelioma and Adreno-Cortical cancer cell proliferation upon delivery with minicells. See Example 10.

Accordingly, in some embodiments the minicell comprises siRNA, which inhibits ribonucleotide reductase M1 (RRM1) expression.

6. Other Antineoplastic Therapies

Antineoplastic therapies useful for administration with the intact, bacterially derived minicells or killed bacterial cells comprising a CD1d-restricted iNKT antigen of the present disclosure also include non-drug therapies that induce cancer cell death, such as radiation therapies, surgical methods, adoptive cell therapies, enzyme-prodrug therapies and microorganism-based anti-tumor therapies.

For example, in some embodiments, the encapsulated CD1d-restricted iNKT antigens of the present disclosure are administered in combination with an antineoplastic therapy including, but not limited to, targeted radiation therapy, stereotactic radiation, photodynamic therapy, microwave thermal ablation, cryoablation, high intensity ultrasound, radiofrequency ablation, laser beam irradiation, cyberknife, and hyperthermia tumor treatment.

In some embodiments, the encapsulated CD1d-restricted iNKT antigens of the present disclosure are administered in combination with an antineoplastic prodrug therapy, including, but not limited to, directed enzyme prodrug therapy (DEPT), antibody-directed enzyme prodrug therapy (ADEPT), Gene-directed enzyme prodrug therapy (GDEPT), Virus-directed enzyme prodrug therapy (VDEPT), Polymer-directed enzyme prodrug therapy (PDEPT), and clostridial-directed enzyme prodrug therapy (CDEPT).

In some embodiments, encapsulated CD1d-restricted iNKT antigens of the present disclosure are administered in combination with an adoptive cell therapy that induces cancer cell death such as a chimeric antigen receptor (CAR) T cell therapy. In some embodiments, the CAR T cells comprises a chimeric antigen receptor directed against a tumor antigen. In some embodiments, the CAR T cells comprises a chimeric antigen receptor directed against a α-folate receptor, B-Cell Maturation Antigen (BCMA), carboxyanhydrase-IX (CAIX), carcinoembryonic antigen (CEA), CD22, CD19, CD30, CD133, CLL-1, disialoganglioside (GD2), EPH receptor A2, (EphA2), epithelial cell adhesion molecule, (EpCAM), glypican-3 (GPC3), epidermal growth factor receptor (EGFR), EGFRvIII, fibroblast activation protein a (FAP), hepatocyte growth factor receptor (c-Met), human epidermal growth factor receptor-2 (HER2), IL13Rα2, L1 cell adhesion molecule (L1-CAM), mesothelin, mucin (MUC-1), PSCA, prostate-specific membrane antigen (PSMA), receptor tyrosine kinase-like orphan receptor 1 (ROR1), or vascular endothelial growth factor receptor (VEGFR). In some embodiments, the encapsulated CD1d-restricted iNKT antigens of the present disclosure are administered in combination with an immune checkpoint therapy such as an anti-PD-1/PD-L1 or anti-CTLA-4 antibody therapy. In some embodiments, the CAR T cells comprise an anti-PD-1/PD-L1 or anti-CTLA-4 antibody.

In some embodiments, a non-drug antineoplastic therapy is administered in addition to one or more antineoplastic agents described above. Any combination of antineoplastic agents and therapies is suitable for administration with the disclosed encapsulated CD1d-restricted iNKT antigens provided that the antineoplastic agents and/or therapies effect the death of cancer cells.

III. Encapsulation of CD1d-Restricted iNKT Cell Antigens and Antineoplastic Agents The CD1d-restricted iNKT antigens of the present disclosure can be effectively delivered to phagocytic cells by encapsulating the antigen using intact, bacterially-derived minicells or killed bacterial cells that can be uptaken by macrophages and/or by dendritic cells.

In some embodiments, the encapsulated CD1d-restricted iNKT antigens are administered in combination with an antineoplastic agent that is also encapsulated, for example, using intact, bacterially derived minicells or killed bacterial cells. In some embodiments, the CD1d-restricted iNKT antigens are administered in combination with an antineoplastic agent, where both the CD1d-restricted antigen and the antineoplastic agent are encapsulated in intact, bacterially derived minicells or killed bacterial cells. In some embodiments, the CD1d-restricted antigen and the antineoplastic agent are encapsulated in the same minicell or killed bacterial cell. In some embodiments, the CD1d-restricted antigen and the antineoplastic agent are encapsulated in separate minicells or killed bacterial cells. In some embodiments, the encapsulated CD1d-restricted antigen is administered with an antineoplastic agent that is not encapsulated.

A. Intact Bacterially-Derived Minicells

The term "minicell" is used here to denote a derivative of a bacterial cell that lacks chromosomes ("chromosome-free") and is engendered by a disturbance in the coordination, during binary fission, of cell division with DNA segregation. Minicells are distinct from other small vesicles, such as so-called "membrane blebs" (about 0.2 μm or less in size), which are generated and released spontaneously in certain situations but which are not due to specific genetic rearrangements or episomal gene expression. By the same token, intact minicells are distinct from bacterial ghosts, which are not generated due to specific genetic rearrangements or episomal gene expression. Bacterially derived minicells employed in this disclosure are fully intact and thus are distinguished from other chromosome-free forms of bacterial cellular derivatives characterized by an outer or defining membrane that is disrupted or degraded, even removed. See U.S. Pat. No. 7,183,105 at col. 111, lines 54 et seq. The intact membrane that characterizes the minicells of the present disclosure allows retention of the therapeutic payload within the minicell until the payload is released, post-uptake, within a phagocytic cell or tumor cell.

Minicell or EDVs are anucleate, non-living nanoparticles produced as a result of inactivating the genes that control normal bacterial cell division, thereby de-repressing polar sites of cell. Ma et al., 2004. The de-repression means that the bacteria divide in the center as well as at the poles; the polar division resulting in minicells which the inventors of the present disclosure have shown can function as leak-resistant, micro-reservoir carriers that allow efficient packaging of a range of different chemotherapeutic drugs. Moreover, in contrast to current stealth liposomal drug carriers like DOXIL (liposomal doxorubicin), for example, that can package only ~14,000 molecules per particle (Park et al., 2002), or "armed antibodies," which can carry fewer than 5 drug molecules, EDVs can readily accommodate payloads of up to 1 million drug molecules. Further, EDVs can be targeted to over-expressed receptors on the surface of cancer cells using bispecific antibodies, see section D infra, which allows highly significant tumor growth-inhibition and/or regression, both in vitro and in vivo.

The minicells employed in the present invention can be prepared from bacterial cells, such as *E. coli* and *S. typhimurium*. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and a chromosome-less minicell. See de Boer et al., 1992; Raskin & de Boer, 1999; Hu & Lutkenhaus, 1999; Harry, 2001.

In addition to min operon mutations, chromosome-less minicells also are generated following a range of other genetic rearrangements or mutations that affect septum formation, for example, in the divIVB1 in *B. subtilis*. See Reeve and Cornett, 1975. Minicells also can be formed following a perturbation in the levels of gene expression of proteins involved in cell division/chromosome segregation. For instance, over-expression of minE leads to polar division and production of minicells. Similarly, chromosome-less minicells can result from defects in chromosome segregation, e.g., the smc mutation in *Bacillus subtilis* (Britton et al., 1998), the spoOJ deletion in *B. subtilis* (Ireton et al., 1994), the mukB mutation in *E. coli* (Hiraga et al., 1989), and the parC mutation in *E. coli* (Stewart and D'Ari, 199)). Further, CafA can enhance the rate of cell division and/or inhibit chromosome partitioning after replication (Okada et al., 1994), resulting in formation of chained cells and chromosome-less minicells.

Accordingly, minicells can be prepared for the present disclosure from any bacterial cell, be it of Gram-positive or Gram-negative origin due to the conserved nature of bacterial cell division in these bacteria. Furthermore, the minicells used in the disclosure should possess intact cell walls (i.e., are "intact minicells"), as noted above, and should be distinguished over and separated from other small vesicles, such as membrane blebs, which are not attributable to specific genetic rearrangements or episomal gene expression.

In a given embodiment, the parental (source) bacteria for the minicells can be Gram positive, or they can be Gram negative. In one aspect, the parental bacteria are one or more selected from Terra-/Glidobacteria (BV1), Proteobacteria (BV2), BV4 including Spirochaetes, Sphingobacteria, and Planctobacteria. Pursuant to another aspect, the bacteria are one or more selected from Finnicutes (BV3) such as Bacilli, Clostridia or Tenericutes/Mollicutes, or Actinobacteria (BV5) such as Actinomycetales or Bifidobacteriales.

Pursuant to the invention, killed bacterial cells are non-living prokaryotic cells of bacteria, cyanobateria, eubacteria and archaebacteria, as defined in the 2nd edition of *Bergey's Manual Of Systematic Biology*. Such cells are deemed to be "intact" if they possess an intact cell wall and/or cell membrane and contain genetic material (nucleic acid) that is endogenous to the bacterial species. Methods of preparing killed bacterial cells are described, for instance, in U.S. 2008/0038296.

In yet a further aspect, the bacteria are one or more selected from Eobacteria (Chloroflexi, Deinococcus-Thermus), Cyanobacteria, Thermodesulfobacteria, thermophiles (Aquificae, Thermotogae), Alpha, Beta, Gamma (Enterobacteriaceae), Delta or Epsilon Proteobacteria, Spirochaetes, Fibrobacteres, Chlorobi/Bacteroidetes, Chlamydiae/Verrucomicrobia, Planctomycetes, Acidobacteria, Chrysiogenetes, Deferribacteres, Fusobacteria, Gemmatimonadetes, Nitrospirae, Synergistetes, Dictyoglomi, Lentisphaerae Bacillales, Bacillaceae, Listeriaceae, Staphylococcaceae, Lactobacillales, Enterococcaceae, Lactobacillaceae, Leuconostocaceae, Streptococcaceae, Clostridiales, Halanaerobiales, Thermoanaerobacterales, Mycoplasmatales, Entomoplasmatales, Anaeroplasmatales, Acholeplasmatales, Haloplasmatales, Actinomycineae, Actinomycetaceae, Corynebacterineae, Nocardiaceae, Corynebacteriaceae, Frankineae, Frankiaceae, Micrococcineae, Brevibacteriaceae, and Bifidobacteriaceae.

For pharmaceutical use, a composition of the disclosure should comprise minicells or killed bacterial cells that are isolated as thoroughly as possible from immunogenic components and other toxic contaminants. Methodology for purifying bacterially derived minicells to remove free endotoxin and parent bacterial cells are described, for example, in WO 2004/113507. Briefly, the purification process achieves removal of (a) smaller vesicles, such as membrane blebs, which are generally smaller than 0.2 μm in size, (b) free endotoxins released from cell membranes, and (c) parental bacteria, whether live or dead, and their debris, which also are sources of free endotoxins. Such removal can be implemented with, inter alia, a 0.2 μm filter to remove smaller vesicles and cell debris, a 0.45 μm filter to remove parental cells following induction of the parental cells to form filaments, antibiotics to kill live bacterial cells, and antibodies against free endotoxins.

Underlying the purification procedure is a discovery by the present inventors that, despite the difference of their bacterial sources, all intact minicells are approximately 400 nm in size, i.e., larger than membrane blebs and other smaller vesicles and yet smaller than parental bacteria. Size determination for minicells can be accomplished by using solid-state, such as electron microscopy, or by liquid-based techniques, e.g., dynamic light scattering. The size value yielded by each such technique can have an error range, and the values can differ somewhat between techniques. Thus, the size of minicells in a dried state can be measured via electron microscopy as approximately 400 nm±50 nm. Dynamic light scattering can measure the same minicells to be approximately 500 nm±50 nm in size. Also, drug-packaged, ligand-targeted minicells can be measured, again using dynamic light scattering, to be approximately 400 nm to 600 nm±50 nm.

This scatter of size values is readily accommodated in practice, e.g., for purposes of isolating minicells from immunogenic components and other toxic contaminants, as described above. That is, an intact, bacterially derived minicell is characterized by cytoplasm surrounded by a rigid membrane, which gives the minicell a rigid, spherical structure. This structure is evident in transmission-electron micrographs, in which minicell diameter is measured, across the minicell, between the outer limits of the rigid membrane. This measurement provides the above-mentioned size value of 400 nm±50 nm.

Another structural element of a killed bacterial cells or a minicell derived from Gram-negative bacteria is the O-polysaccharide component of lipopolysaccharide (LPS), which is embedded in the outer membrane via the lipid A anchor. The component is a chain of repeat carbohydrate-residue units, with as many as 70 to 100 repeat units of four to five sugars per repeat unit of the chain. Because these chains are not rigid, in a liquid environment, as in vivo, they can adopt a waving, flexible structure that gives the general appearance of seaweed in a coral sea environment; i.e., the chains move with the liquid while remaining anchored to the minicell membrane.

Influenced by the O-polysaccharide component, dynamic light scattering can provide a value for minicell size of about 500 nm to about 600 nm, as noted above. Nevertheless, minicells from Gram-negative and Gram-positive bacteria alike readily pass through a 0.45 μm filter, which substantiates an effective minicell size of 400 nm±50 nm. The above-mentioned scatter in sizes is encompassed by the present invention and, in particular, is denoted by the qualifier "approximately" in the phrase "approximately 400 nm in size" and the like.

In relation to toxic contaminants, a composition of the disclosure preferably comprises less than about 350 EU free endotoxin. Illustrative in this regard are levels of free endotoxin of about 250 EU or less, about 200 EU or less, about 150 EU or less, about 100 EU or less, about 90 EU or less, about 80 EU or less, about 70 EU or less, about 60 EU or less, about 50 EU or less, about 40 EU or less, about 30 EU or less, about 20 EU or less, about 15 EU or less, about 10 EU or less, about 9 EU or less, about 8 EU or less, about 7 EU or less, about 6 EU or less, about 5 EU or less, about 4 EU or less, about 3 EU or less, about 2 EU or less, about 1 EU or less, about 0.9 EU or less, about 0.8 EU or less, about 0.7 EU or less, about 0.6 EU or less, about 0.5 EU or less, about 0.4 EU or less, about 0.3 EU or less, about 0.2 EU or less, about 0.1 EU or less, about 0.05 EU or less, or about 0.01 EU or less.

A composition of the disclosure also can comprise at least about $10^9$ minicells or killed bacterial cells, e.g., at least about $1\times10^9$, at least about $2\times10^9$, at least about $5\times10^9$, or at least $8\times10^9$. In some embodiments, the composition comprises no more than about $10^{11}$ minicells or killed bacterial cells, e.g., no more than about $1\times10^{11}$ or no more than about $9\times10^{10}$, or no more than about $8\times10^{10}$.

1. Loading Active Agents into Minicells or Killed Bacterial Cells

Active agents, such as a CD1d-restricted iNKT cell antigen, or antineoplastic agents, such as small molecular drugs, proteins and functional nucleic acids can be packaged into minicells directly by co-incubating a plurality of intact minicells with the active agent in a buffer. The buffer composition can be varied, as a function of conditions well known in this field, to optimize the loading of the active agent in the intact minicells. An exemplary buffer suitable for loading includes, but is not limited to, phosphate buffered saline (PBS). Once packaged, the active agent remains inside the minicell and is protected from degradation.

Active agents such as functional nucleic acids or proteins that can be encoded for by a nucleic acid, can be introduced into minicells by transforming into the parental bacterial cell a vector, such as a plasmid, that encodes the active agents. When a minicell is formed from the parental bacterial cell, the minicell retains certain copies of the plasmid and/or the expression product, the antineoplastic agent. More details of packaging and expression product into a minicell is provided in WO 2003/033519, the contents of which are incorporated into the present disclosure in its entirety by reference.

Data presented in WO 2003/033519 demonstrated, for example, that recombinant minicells carrying mammalian gene expression plasmids can be delivered to phagocytic cells and to non-phagocytic cells. WO 2003/033519 also described the genetic transformation of minicell-producing parent bacterial strains with heterologous nucleic acids carried on episomally-replicating plasmid DNAs. Upon separation of parent bacteria and minicells, some of the episomal DNA segregated into the minicells. The resulting recombinant minicells were readily engulfed by mammalian phagocytic cells and became degraded within intracellular phagolysosomes. Moreover, some of the recombinant DNA escaped the phagolysosomal membrane and was transported to the mammalian cell nucleus, where the recombinant genes were expressed.

In other embodiments, multiple nucleic acids directed to different mRNA targets can be packaged in the same minicell. Such an approach can be used to combat drug resistance and apoptosis resistance. For instance, cancer patients routinely exhibit resistance to chemotherapeutic drugs. Such resistance can be mediated by over-expression of genes such as multi-drug resistance (MDR) pumps and anti-apoptotic genes, among others. To combat this resistance, minicells can be packaged with therapeutically significant concentrations of functional nucleic acid to MDR-associated genes and administered to a patient before chemotherapy. Furthermore, packaging into the same minicell multiple functional nucleic acid directed to different mRNA targets can enhance therapeutic success since most molecular targets are subject to mutations and have multiple alleles. More details of directly packaging a nucleic acid into a minicell is provided in WO 2009/027830, the contents of which are incorporated into the present disclosure in its entirety by reference.

Small molecule drugs, whether hydrophilic or hydrophobic, can be packaged in minicells by creating a concentration gradient of the drug between an extracellular medium comprising minicells and the minicell cytoplasm. When the extracellular medium comprises a higher drug concentration than the minicell cytoplasm, the drug naturally moves down this concentration gradient, into the minicell cytoplasm. When the concentration gradient is reversed, however, the drug does not move out of the minicells. More details of the drug loading process and its surprising nature are found, for instance, in U.S. Patent Application Publication No. 2008/0051469, the contents of which are specifically incorporated by reference.

To load minicells with drugs that normally are not water soluble, the drugs initially can be dissolved in an appropriate solvent. For example, paclitaxel can be dissolved in a 1:1 blend of ethanol and cremophore EL (polyethoxylated castor oil), followed by a dilution in PBS to achieve a solution of paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm or the membrane of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm. The loading into minicells of a diversity of representative small molecule drugs has been shown, illustrating different sizes and chemical properties: doxorubicin, paclitaxel, fluoro-paclitaxel, cisplatin, vinblastine, monsatrol, thymidylate synthase (TS) inhibitor OSI-7904, irinotecan, 5-fluorouracil, gemcitabine, and carboplatin. Across the board, moreover, the resultant, small molecule drug-packaged minicells show significant anti-tumor efficacy, in vitro and in vivo.

2. Targeting Minicells to Specific Mammalian Cells and Tumors

The inventors discovered that blood vessels around tumor cells display a loss of integrity; that is, the vessels have large fenestrations and are "leaky," even in the blood brain barrier (BBB) environment. When cancer cells establish, they secrete substances that promote the formation of new blood vessels—a process called angiogenesis. These blood vessels grow quickly and, unlike normal blood vessels, they are leaky with "holes" (fenestrations) ranging from 50 nm to 1.2 μm (hyperpermeable vasculature). Drug delivery particles such as liposomes are currently believed to effect tumor-targeting by a passive process involving extravasation from the leaky vasculature that supports the tumor microenvironment. Hobbs et al., 1998. Although it has been shown that the abnormal tumor microenvironment is characterized by interstitial hypertension, and that this phenomenon may limit access of anti-cancer antibody therapeutics, this does not appear to be an absolute barrier as is exemplified by immunoliposomes (Nielsen et al, 2002) and antibody conjugated to Quantum Dots (Gao et al., 2004). This phenomenon also holds true for the EDV which has the added advantage of carrying a specifically directed tumor antibody. Following IV injection the EDV extravasates into the tumor microenvironment and this is followed by active targeting via cancer cell-surface receptor engagement and endocytosis. In contrast to conventional understanding, therefore, particles that are as large as minicells, i.e., much larger than the above-discussed consensus pore size limitations of the BBB, nevertheless are smaller than the fenestrations in the walls of the leaky blood vessel; hence, they can extravasate passively through these fenestrations and into the tumor microenvironment.

Upon entering the tumor microenvironment, minicells are able to trigger macropinocytosis or receptor-mediated internalization by the host tumor cells and to be taken up by them. Thus, a minicell that is packaged with an antineoplastic agent will release the agent into the cytoplasm of the tumor cell, killing it.

Pursuant to a further aspect of this disclosure, minicells or killed bacterial cells that contain an antineoplastic agent and/or a CD1d-restricted iNKT cell antigen can be directed to a target mammalian tumor cell via a ligand. In some embodiments the ligand is "bispecific." That is, the ligand displays a specificity for both minicell and mammalian (tumor) cell components, such that it causes a given vesicle to bind to the target cell, whereby the latter engulfs the former. Use of bispecific ligands to target a minicell to a tumor cell is further described in WO 2005/056749 and WO 2005/079854, and use of bispecific ligands to target a killed bacterial cell to a tumor cell is further described in U.S. Pat. No. 8,591,862. Once such a ligand is attached to a vesicle, the unoccupied specificity ("monospecificity") of the ligand pertains until it interacts with the target (tumor) mammalian cell. A number of tumor targeting ligands are known in the art (Hong et al., 2011; Hoelder et al., 2012; Galluzzi et al., 2013). Several peptides, such as somatostatin (SST) peptide, vasoactive intestinal peptide (VIP), Arg-Gly-Asp (RGD) peptide, and bombesin/gastrin-releasing peptide (BBN/GRP), have been successfully characterized for tumor receptor imaging (De Jong et al., 2009; Tweedle, 2009; Schottelius and Wester 2009; Igarashi et al., 2011; Laverman et al., 2012).

Tumor-targeting peptide sequences can be selected mainly in three different ways: (1) derivatization from natural proteins (Nagpal et al., 2011); (2) chemical synthesis and structure-based rational engineering (Andersson et al., 2000; Merrifield, 2006); and (3) screening of peptide libraries (Gray and Brown 2013). Among the methods, phage display technology is a conventional but most widely used method with many advantages such as ease of handling and large numbers of different peptides can be screened effectively (Deutscher, 2010).

Receptors that are overexpressed on tumor cells rather than on normal cells are excellent candidates for in vivo tumor imaging. To date, many tumor targeting peptides and their analogs have been identified as described below.

Arg-Gly-Asp (RGD) peptide—RGD specifically binds to integrin receptors (Ruoslahti, 1996). Integrins constitute two subunits (α and β subunits). The integrin family, especially $αv\beta_3$, is associated with tumor angiogenesis and metastasis. They are overexpressed on endothelial cells during angiogenesis, but barely detectable in most normal organs. Therefore, they are widely used for diagnostic imaging.

Bombesin (BBN)/gastrin-releasing peptide (GRP)—Amphibian BBNs and their related peptides consist of a family of neuropeptides exhibiting various physiological effects such as exocrine and endocrine secretions, thermoregulation, sucrose regulations as well as cell growth (Ohki-Hamazaki et al., 2005). The bombesin-like peptide receptors have 4-subtypes: the neuromedin B receptor, the bombesin 3 receptor, the GRP receptor, and the bombesin 4 receptor. These receptors are overexpressed in many tumors such as breast cancer, ovarian cancer and gastrointestinal stromal tumors.

Cholecystokinin (CCK)/gastrin peptide—CCK and gastrin are structurally and functionally similar peptides that exert a variety of physiological actions in the gastrointestinal tract as well as the central nervous system (Matsuno et al., 1997). Three types of receptors for CCK (CCK1, CCK2 and CCK2i4sv have been identified, which all belong to the superfamily of GPCRs. Among them, CCK2/gastrin receptors have been frequently found in human cancers such as stromal ovarian cancers and astrocytomas.

α-Melanocyte-stimulating hormone (α-MSH)—α-MSHs are linear tridecapeptides, mainly responsible for skin pigmentation regulation (Singh and Mukhopadhyay, 2014). α-MSHs and their analogs exhibit binding affinities to melanocortin-1 receptors (MC-1r) which are expressed in over 80% of human melanoma metastases, and thus, are widely used as vehicles for melanoma-targeted imaging and radiotherapy.

Neuropeptide Y (NPY)—NPY is a 36 amino acid peptide and belongs to the pancreatic polypeptide family (Tatemoto, 2004). NPY receptors are overexpressed in various tumors including neuroblastomas, sarcomas, and breast cancers.

Neurotensin (NT)—NT is a 13 amino acid peptide, targeting NT receptor which has been identified in various tumors such as ductal pancreatic adenocarcinomas, small cell lung cancer, and medullary thyroid cancer (Tyler-McMahon et al., 2000). Therefore, it is an attractive candidate for cancer imaging.

Prostate Specific Membrane Antigen (PSMA)—Prostate cancer cells overexpress PSMA on the cell surface (Silver et al., 2007; Ghosh and Heston, 2004; Mhawech-Fauceglia et al., 2007; Santoni et al., 2014). There are several available radiopharmaceuticals that target PSMA including [$^{68}$Ga]Ga-PSMA-HBED-CC (also known as [*Ga]Ga-PSMA-11 [PET]), a monoclonal antibody (mAb) [$^{177}$Lu]Lu/[$^{90}$Y]Y-J591 (therapy), [$^{123}$I]I-MIP-1072 (planar/SPECT), [$^{131}$I]I-MIP-1095 (therapy), and the theranostic agents PSMA-I&T and DKFZ-PSMA-617 (PSMA-617), which are labeled with $^{68}$Ga for PET or with $^{177}$Lu for therapy.

Somatostatin (SST) peptide—SSTs are naturally occurring cyclopeptide hormones with either 14 or 28 amino acids (Weckbecker et al., 2003). They can inhibit the secretion of insulin, glucagon and some other hormones. Somatostatin receptors (SSTRs; five subtypes SSTR1-SSTR5) are overexpressed in many tumors including gliomas, neuroendocrine tumors and breast tumor. Neuroendocrine neoplasia (NEN) of the GEP system originates most frequently from the pancreas, jejunum, ileum, cecum, rectum, appendix, and colon. The common characteristic of all GEP-NEN is the compound features of endocrine and nerve cells. Well-differentiated NEN overexpresses somatostatin receptors (SSTRs), especially the SSTR-2 subtype.

Substance P—Substance P is an undecapeptide belonging to a family of neuropeptides known as tachykinins (Strand, 1999). Substance P is a specific endogenous ligand known for neurokinin 1 receptor ($NK_1R$) which is found to be expressed on various cancer cells.

T140—T140 is a 14 amino acid peptide with one disulfide bridge and is an inverse agonist of chemokine receptor type 4 (CXCR4) (Burger et al., 2005). Its derivatives are widely used as CXCR4 imaging agents.

Tumor molecular targeted peptide 1 (TMTP1)—TMTP1 is a 5-amino acid peptide that has been found to specifically bind to highly metastatic cancer cells, especially those from a typical liver micrometastasis (Yang et al., 2008).

Vasoactive intestinal peptide (VIP)—VIP is a neuropeptide with 28 amino acids (Igarashi et al., 2011). It promotes vasodilation, cell growth and proliferation. Its action is mainly controlled by two receptor subtypes (VPAC1 and VPAC2). A large amount of VIP receptors is expressed on many tumors including adenocarcinomas of the pancreas and neuroendocrine tumors.

The ligand can be attached to the cell membrane of the vesicles by virtue of the interaction between the ligand and a component on the cell membrane, such as a polysaccharide, a glycoprotein, or a polypeptide. The expressed ligand is anchored on the surface of a vesicle such that the tumor surface component-binding portion of the ligand is exposed so that the portion can bind the target mammalian cell surface receptor when the vesicle and the mammalian tumor cell come into contact.

Alternatively, the ligand can be expressed and displayed by a living counterpart of a bacterially derived vesicle, e.g., by the parent cell of a minicell or by a bacterial cell before it becomes a killed cell. In this instance the ligand does not require a specificity to the vesicle and only displays a specificity to a component that is characteristic of mammalian cells. That is, such component need not be unique to tumor cells, per se, or even to the particular kind of tumor cells under treatment, so long as the tumor cells present the component on their surface.

Upon intravenous administration, vesicles accumulate rapidly in the tumor microenvironment. This accumulation, occurring as a function of the above-described leaky tumor vasculature, effects delivery of vesicle-packaged therapeutic payload to cells of the tumor, which then internalize packaged vesicles.

The inventors have found that this delivery approach is applicable to a range of mammalian tumor cells, including cells that normally are refractory to specific adhesion and endocytosis of minicells. For instance, ligands that comprise an antibody directed at an anti-HER2 receptor or anti-EGF receptor can bind minicells to the respective receptors on a range of targeted non-phagocytic cells, such as lung, ovarian, brain, breast, prostate, and skin cancer cells.

The binding thus achieved precedes uptake of the vesicles by each type of non-phagocytic cells. That is, in the context of the present invention a suitable target cell presents a cell surface receptor the binding of which, by a ligand on a vesicle, elicits endocytosis of that vesicle.

More specifically, the present inventors discovered that the interaction between (a) the ligand on a minicell or a killed bacterial cell and (b) a mammalian cell surface receptor can activate an uptake pathway, called here a "receptor-mediated endocytosis" (rME) pathway, into the late-endosomal/lysosomal compartment of the target host cell, such as a tumor cell. By this rME pathway, the inventors found, bacterially derived vesicles are processed through the early endosome, the late endosome and the lysosome, resulting in release of their payload into the cytoplasm of the mammalian host cell. Moreover, a payload that is a nucleic acid not only escapes complete degradation in the late-endosomal/lysosomal compartment but also is expressed by the host cell.

A tumor targeting ligand for this delivery approach can be "bispecific," as described above, because it binds to surface components on a payload-carrying vesicle and on a target cell, respectively, and its interaction with the latter component leads to uptake of the vesicle into the rME pathway. In any event, a given target cell surface receptor can be a candidate for binding by the ligand, pursuant to the invention, if interaction with the component in effect accesses an endocytic pathway that entails a cytosolic internalization from the target cell surface. Such candidates are readily assessed for suitability in the invention via an assay in which a cell type that presents on its surface a candidate component is co-incubated in vitro with minicells carrying a ligand that binds the candidate and that also is joined to a fluorescent dye or other marker amenable to detection, e.g., visually via confocal microscopy. (An in vitro assay of this sort is described by MacDiarmid et al., 2007b, in the legend to FIG. 3 at page 436.) Thus, an observed internalization of the marker constitutes a positive indication by such an assay that the tested target cell surface receptor is suitable for the present invention.

In accordance with the invention, the ligand can be any polypeptide or polysaccharide that exhibits the desired specificity or specificities. Preferred ligands are antibodies. In its present use the term "antibody" encompasses an immunoglobulin molecule obtained by in vitro or in vivo generation of an immunogenic response. Accordingly, the "antibody" category includes monoclonal antibodies and humanized antibodies, such as single-chain antibody fragments (scFv), bispecific antibodies, etc. A large number of different bispecific protein and antibody-based ligands are known, as evidenced by the review article of Caravella and Lugovskoy, 2010. Antibodies useful in accordance with the present disclosure can be obtained by known recombinant DNA techniques.

By way of non-limiting example, therefore, an antibody that carries specificity for a surface component, such as a tumor antigen, can be used to target minicells to cells in a tumor to be treated. Illustrative cell surface receptors in this regard include any of the RTKs epidermal growth factor receptor (EGFR), vascular endothelial growth factor receptor (VEGFR), platelet-derived growth factor receptor (PDGFR) and insulin-like growth factor receptor (IGFR), each of which is highly expressed in several solid tumors, including brain tumors, and folate receptor, which is overexpressed in some pituitary adenomas. Such a bispecific ligand can be targeted as well to mutant or variant receptors, e.g., the IL-13Rα2 receptor, which is expressed in 50% to 80% of human glioblastoma multiforme tumors, see Wykosky et al., 2008; Jarboe et al., 2007; Debinski et al., 2000; and Okada et al., 1994), but which differs from its physiological counterpart IL4R/IL13R, expressed in normal tissues. See Hershey, 2003. Thus, IL13Rα2 is virtually absent from normal brain cells. See Debinski and Gibo, 2000. Additionally, tumors that metastasize to the brain may overexpress certain receptors, which also can be suitable targets. For instance, Da Silva et al., 2010, showed that brain metastases of breast cancer expressed all members of the HER family of RTKs. HER2 was amplified and overexpressed in 20% of brain metastases, EGFR was overexpressed in 21% of brain metastases, HER3 was overexpressed in 60% of brain metastases and HER4 was overexpressed in 22% of brain metastases. Interestingly, HER3 expression was increased in breast cancer cells residing in the brain.

Illustrative of candidate target cell surface receptors are members of the receptor tyrosine kinases or "RKTs," a family of transmembrane proteins that undergo constitutive internalization (endocytosis) at a rate similar to that of other integral membrane proteins. See Goh and Sorkin, 2013. The family of RKTs is described by Lemmon and Schlessinger, Cell, 141(7): 1117-134 (2010). Exemplary RTKs are ErbB EGFR, ErbB2, ErbB3, ErbB4 Ins InsR, IGF1R, InsRR PDGF PDGFRα, PDGFRβ, CSF1R/Fms, Kit/SCFR, Fit3/Flk2 VEGF VEGFR1/Fit1, VEGFR2/KDR, VEGFR3/Fit4 FGF FGFR1, FGFR2, FGFR3, FGFR4 PTK7 PTK7/CCK4 Trk TrkA, TrkB, TrkC Ror Ror1, Ror2 MuSK Met, Ron Axl, Mer, Tyro3 Tie Tie1, Tie2 Eph EphA1-8, EphA10, EphB1-4, EphB6 Ret Ryk DDR DDR1, DDR2 Ros LMR LMR1, LMR2, LMR3 ALK, LTK STYK1 SuRTK106/STYK1.

Another candidate for suitable target cell surface receptors are the family of membrane-associated, high-affinity folate binding proteins (folate receptor), which bind folate and reduced folic acid derivatives and which mediate delivery of tetrahydrofolate to the interior of cells; the family of membrane-bound cytokine receptors that play a role in the internalization of a cognate cytokine, such as IL13; the surface antigens such as CD20, CD33, mesothelin and HM1.24, that are expressed on certain cancer cells and that mediate the internalization of cognate monoclonal antibodies, e.g., rituximab in the instance of CD20; and the family of adhesion receptors (integrins), which are transmembrane glycoproteins that are trafficked through the endosomal pathway and are major mediators of cancer cell adhesion. In one embodiment of the invention, the tumor cell surface receptor comprises an integrin, neuromedin B receptor, bombesin 3 receptor, GRP receptor, bombesin 4 receptor, CCK2/gastrin, melanocortin-1 receptor (MC-1r), neuropeptide Y (NPY) receptor, neutrotensin (NT) receptor, prostate specific membrane antigen (PSMA), somatostatin (SST) receptor, neurokinin 1 receptor (NK1R), chemokine receptor type 4 (CXCR4), vasoactive intestinal peptide (VIP), epidermal growth factor receptor (EGFR), vascular endothelial growth factor receptor (VEGFR), platelet-derived growth factor receptor (PDGFR), insulin-like growth factor receptor (IGFR), or any combination thereof.

According to another embodiment of the invention, the cell surface receptor is an antigen which is uniquely expressed on a target cell in a disease condition, but which remains either non-expressed, expressed at a low level or non-accessible in a healthy condition. Examples of such target antigens which might be specifically bound by a targeting ligand of the invention may advantageously be selected from EpCAM, CCR5, CD19, HER-2 neu, HER-3, HER-4, EGFR, PSMA, CEA, MUC-1 (mucin), MUC2, MUC3, MUC4, MUC5, MUC5, MUC7, BhcG, Lewis-Y. CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRVIII, LG, SAS and CD63.

3. Purity

Minicells of the invention are substantially free from contaminating parent bacterial cells. Thus, minicell-comprising formulations preferably comprise fewer than about 1 contaminating parent bacterial cell per $10^7$ minicells, fewer than about 1 contaminating parent bacterial cell per $10^8$ minicells, fewer than about 1 contaminating parent bacterial cell per $10^9$ minicells, fewer than about 1 contaminating parent bacterial cell per $10^{10}$ minicells, or fewer than about 1 contaminating parent bacterial cell per $10^{11}$ minicells.

Methods of purifying minicells are known in the art and described in PCT/IB02/04632. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Another purification method employs density gradient centrifugation in a biologically compatible medium. After centrifugation, a minicell band is collected from the gradient, and, optionally, the minicells are subjected to further rounds of density gradient centrifugation to maximize purity. The method may further include a preliminary step of performing differential centrifugation on the minicell-containing sample. When performed at low centrifugal force, differential centrifugation will remove some portion of parent bacterial cells, thereby enriching the supernatant for minicells.

Particularly effective purification methods exploit bacterial filamentation to increase minicell purity. Thus, a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. One highly effective exemplary combination of methods is as follows:

Step A: Differential centrifugation of a minicell producing bacterial cell culture. This step, which may be performed at 2,000 g for about 20 minutes, removes most parent bacterial cells, while leaving minicells in the supernatant;

Step B: Density gradient centrifugation using an isotonic and non-toxic density gradient medium. This step separates minicells from many contaminants, including parent bacterial cells, with minimal loss of minicells. Preferably, this step is repeated within a purification method;

Step C: Cross-flow filtration through a 0.45 μm filter to further reduce parent bacterial cell contamination.

Step D: Stress-induced filamentation of residual parent bacterial cells. This may be accomplished by subjecting the minicell suspension to any of several stress-inducing environmental conditions;

Step E: Antibiotic treatment to kill parent bacterial cells;

Step F: Cross-flow filtration to remove small contaminants, such as membrane blebs, membrane fragments, bacterial debris, nucleic acids, media components and so forth, and to concentrate the minicells. A 0.2 μm filter may be employed to separate minicells from small contaminants, and a 0.1 μm filter may be employed to concentrate minicells;

Step G: Dead-end filtration to eliminate filamentous dead bacterial cells. A 0.45 um filter may be employed for this step; and Step H: Removal of endotoxin from the minicell preparation. Anti-Lipid A coated magnetic beads may be employed for this step.

IV. Formulations

The invention includes within its scope compositions, or formulations, comprising intact, bacterially derived minicells or killed bacterial cells that encapsulate CD1d-restricted iNKT cell antigens (e.g., α-GalCer). In some embodiments, the formulations comprise bacterially-derived minicells or killed bacterial cells comprising a CD1d-restricted iNKT cell antigen alone or in combination with an antineoplastic agent. In some embodiments, the formulations comprise intact bacterially-derived minicells or killed bacterial cells comprising a CD1d-restricted invariant Natural Killer T (iNKT) cell antigen and bacterially-derived minicells or killed bacterial cells comprising an antineoplastic agent. For example: (a) the CD1d-restricted iNKT cell antigen and the antineoplastic agent can be comprised within the same minicell or killed bacterial cell; or (b) the CD1d-restricted iNKT cell antigen can be comprised within a first minicell or killed bacterial cell, and the antineoplastic can be comprised within a second minicell or killed bacterial cell.

In an exemplary embodiment, the compositions disclosed herein comprise the CD1d-restricted iNKT cell antigen α-galactosylceramide (α-GalCer) and an antineoplastic agent, wherein the α-GalCer and the antineoplastic agent are comprised within one or more intact bacterially-derived minicells. In an exemplary embodiment, the compositions disclosed herein comprise the CD1d-restricted iNKT cell antigen α-GalCer and the antineoplastic agent doxorubicin, wherein the α-GalCer and the doxorubicin are comprised within one or more intact bacterially-derived minicells.

In some embodiments, the formulations also optionally comprise at least one bispecific ligand for targeting the minicell to a target cell. The minicell and ligand may be any of those described herein. Thus, the bispecific ligand of the present invention is capable of binding to a surface component of the intact bacterially-derived minicell and to a surface component of a target mammalian cell.

A formulation comprising minicells, or killed bacterial cells, drugs (e.g., at least one antineoplastic agent) and optionally bispecific ligands of the present invention (that is, a formulation that includes such minicells, or killed bacterial cells, drugs and ligands with other constituents that do not interfere unduly with the drug or drug-delivering quality of the composition) can be formulated in conventional manner, using one or more pharmaceutically acceptable carriers or excipients.

Formulations or compositions of the disclosure can be presented in unit dosage form, e.g., in ampules or vials, or in multi-dose containers, with or without an added preservative. The formulation can be a solution, a suspension, or an emulsion in oily or aqueous vehicles, and can contain formulatory agents, such as suspending, stabilizing and/or dispersing agents. A suitable solution is isotonic with the blood of the recipient and is illustrated by saline, Ringer's solution, and dextrose solution. Alternatively, formulations can be in lyophilized powder form, for reconstitution with a suitable vehicle, e.g., sterile, pyrogen-free water or physiological saline. The formulations also can be in the form of a depot preparation. Such long-acting formulations can be administered by implantation (for instance, subcutaneously or intramuscularly) or by intramuscular injection. In some embodiments, administering comprises enteral or parenteral administration. In some embodiments administering comprises administration selected from oral, buccal, sublingual, intranasal, rectal, vaginal, intravenous, intramuscular, and subcutaneous injection.

In some aspects, a composition comprising an immunogenically effective amount" of an encapsulated CD1d-restricted iNKT cell antigen is provided. An "immunogenically effective amount" as used herein refers to the amount of antigen sufficient to elicit an immune response. In the context of a CD1d-restricted iNKT cell antigen, an immunogenically effective amount is the amount of antigen sufficient activate an iNKT cell response. The effectiveness of CD1d-restricted iNKT cell antigen as an immunogen, can be assessed, for example, by measuring increases in cytokine (e.g., IFNγ) production following administration.

In some aspects, a composition that includes a therapeutically effective amount of an antineoplastic agent is provided. A "therapeutically effective" amount of an antineoplastic agent is a dosage of the agent in question, e.g., a siRNA or a super-cytotoxic drug that invokes a pharmacological response when administered to a subject, in accordance with the present disclosure.

In the context of the present disclosure, therefore, a therapeutically effective amount can be gauged by reference to the prevention or amelioration of the tumor or a symptom of tumor, either in an animal model or in a human subject, when bacterially derived minicells or killed bacterial cells carrying a therapeutic payload are administered, as further described below. An amount that proves "therapeutically effective amount" in a given instance, for a particular subject, may not be effective for 100% of subjects similarly treated for the tumor, even though such dosage is deemed a "therapeutically effective amount" by skilled practitioners. The appropriate dosage in this regard also will vary as a function, for example, of the type, stage, and severity of the tumor.

When "therapeutically effective" is used to refer to the number of minicells or killed bacterial cells in a pharmaceutical composition, the number can be ascertained based on what antineoplastic agent is packaged into the minicells or killed bacterial cells and the efficacy of that agent in treating a tumor. The therapeutic effect, in this regard, can be measured with a clinical or pathological parameter such as tumor mass. A reduction or reduced increase of tumor mass, accordingly, can be used to measure therapeutic effects.

V. Administration Routes

Formulations of the invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The encapsulated CD1d-restricted iNKT cell antigens and the antineoplastic agents can be administered by the same route or by different routes of administration. For example, the encapsulated CD1d-restricted iNKT cell antigen can be administered systemically and the antineoplastic agent can be administered locally. In some embodiments, both the encapsulated CD1d-restricted iNKT cell antigen and the antineoplastic agent are administered systemically.

The mode and site of administration is dependent on the location of the target cells. For example, the target phagocytic cells that uptake the encapsulated CD1d-restricted iNKT cell antigen can be found both in the tumor microenvironment and the in the vasculature associated with liver spleen and lymph nodes. Accordingly, the encapsulated CD1d-restricted iNKT cell antigen may be delivered via targeted and/or non-targeted bacterially derived minicells or killed bacterial cells.

The antineoplastic agents can also be administered via targeted and/or non-targeted methods. For example, a tumor metastasis may be more efficiently treated via intravenous or intraperitoneal delivery of targeted compositions, such as, for example, intravenous or intraperitoneal delivery of targeted bacterially derived minicells. A combination of routes may also may be employed. For example, cytotoxic drug-loaded and receptor-targeted minicells may be administered locally as well as intravenously, and the encapsulated CD1d-restricted iNKT cell antigen (receptor-targeted or non-targeted) minicells may be administered intravenously. The administration of targeted, drug-packaged minicells may target surface-exposed tumors, while the full combination of minicells administered intravenously may target tissue-localized tumors and also elicit the anti-tumor immune response.

VI. Administration Schedules

In general, the formulations disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Optimal precision in achieving concentrations of encapsulated CD1d-restricted iNKT cell antigen and drug within the range that yields maximum efficacy with minimal side effects may require a regimen based on the kinetics of the encapsulated CD1d-restricted iNKT cell antigen and antineoplastic drug availability to target sites and target cells. Distribution, equilibrium, and elimination of the encapsulated CD1d-restricted iNKT cell antigen and antineoplastic drug may be considered when determining the optimal concentration for a treatment regimen. The dosages of the encapsulated CD1d-restricted iNKT cell antigen and antineoplastic drugs may be adjusted when used in combination, to achieve desired effects.

Moreover, the dosage administration of the formulations may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See, e.g., WO 00/67776.

Specifically, the formulations of encapsulated CD1d-restricted iNKT cell antigen and/or antineoplastic drug may be administered at least once a week over the course of several weeks. In one embodiment, the formulations encapsulated CD1d-restricted iNKT cell antigen and/or antineoplastic drug are administered at least once a week over several weeks to several months. The encapsulated CD1d-restricted iNKT cell antigen and one or more antineoplastic drugs can be administered simultaneously, sequentially, or intermittently in defined intervals.

More specifically, the formulations of encapsulated CD1d-restricted iNKT cell antigen and/or antineoplastic drug may be administered at least once a day for about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or about 31 days. Alternatively, the formulations of encapsulated CD1d-restricted iNKT cell antigen and/or antineoplastic drug may be administered about once every day, about once every about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days or more.

The formulations of encapsulated CD1d-restricted iNKT cell antigen and/or antineoplastic drug may alternatively be administered about once every week, about once every about 2, about 3, about 4, about 5, about 6, about 7, about 8, about 9, about 10, about 11, about 12, about 13, about 14, about 15, about 16, about 17, about 18, about 19 or about 20 weeks or more. Alternatively, the formulations of encapsulated CD1d-restricted iNKT cell antigen and/or antineoplastic drug may be administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more.

The formulations of encapsulated CD1d-restricted iNKT cell antigen and/or antineoplastic drug may alternatively be administered about twice every week, about twice every about 2, about 3, about 4, about 5, about 6, about 7, about 8, about 9, about 10, about 11, about 12, about 13, about 14, about 15, about 16, about 17, about 18, about 19 or about 20 weeks or more. Alternatively, the formulations of encapsulated CD1d-restricted iNKT cell antigen and/or antineoplastic drug may be administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more.

Alternatively, the formulations of encapsulated CD1d-restricted iNKT cell antigen and/or antineoplastic drug may be administered about once every month, about once every about 2, about 3, about 4, about 5, about 6, about 7, about 8, about 9, about 10, about 11 or about 12 months or more.

The formulations may be administered in a single daily dose, or the total daily dosage may be administered in divided doses of two, three, or four times daily.

In a method in which encapsulated CD1d-restricted iNKT cell antigens are administered after administration of an antineoplastic agent, administration of the antineoplastic agent may occur anytime from several minutes to several hours after administration of the encapsulated CD1d-restricted iNKT cell antigens. The antineoplastic agent may alternatively be administered anytime from several hours to several days, possibly several weeks up to several months after the encapsulated CD1d-restricted iNKT cell antigens.

More specifically, the encapsulated CD1d-restricted iNKT cell antigens may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 hours after the antineoplastic agent. Moreover, the encapsulated CD1d-restricted iNKT cell antigens may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days after the administration of the antineoplastic agent. In yet another embodiment, the encapsulated CD1d-restricted iNKT cell antigens may be administered at least about 1, about 2, about 3, about 4, about 5, about 6, about 7, about 8, about 9, about 10, about 11, about 12, about 13, about 14, about 15, about 16, about 17, about 18, about 19 or about 20 weeks or more after the antineoplastic agent. In a further embodiment, the encapsulated CD1d-restricted iNKT cell antigens may be administered at least about 1, about 2, about 3, about 4, about 5, about 6, about 7, about 8, about 9, about 10, about 11 or about 12 months after the antineoplastic agent.

In a method in which encapsulated CD1d-restricted iNKT cell antigens are administered before administration of an antineoplastic agent, administration of the antineoplastic agent may occur anytime from several minutes to several hours before administration of the encapsulated CD1d-restricted iNKT cell antigens. The antineoplastic agent may alternatively be administered anytime from several hours to several days, possibly several weeks up to several months before the encapsulated CD1d-restricted iNKT cell antigens.

More specifically, the encapsulated CD1d-restricted iNKT cell antigens may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 hours before the antineoplastic agent. Moreover, the encapsulated CD1d-restricted iNKT cell antigens may be administered at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 or about 31 days before the administration of the antineoplastic agent. In yet another embodiment, the encapsulated CD1d-restricted iNKT cell antigens may be administered at least about 1, about 2, about 3, about 4, about 5, about 6, about 7, about 8, about 9, about 10, about 11, about 12, about 13, about 14, about 15, about 16, about 17, about 18, about 19 or about 20 weeks or more before the antineoplastic agent. In a further embodiment, the encapsulated CD1d-restricted iNKT cell antigens may be administered at least about 1, about 2, about 3, about 4, about 5, about 6, about 7, about 8, about 9, about 10, about 11 or about 12 months before the antineoplastic agent.

VII. Methods of Treating Cancer

The compositions described herein may be used to treat a subject suffering from a cancer. The method disclosed herein comprises administering to the subject an immunogenically effective amount of a composition comprising intact, bacterially derived minicells or killed bacterial cells that encapsulate CD1d-restricted iNKT cell antigen and an antineoplastic agent or therapy. In some embodiments, the CD1d-restricted iNKT cell antigen is comprised in intact bacterially-derived minicells. In some embodiments, the CD1d-restricted iNKT cell antigen and the antineoplastic agents are comprised in one or more intact bacterially-derived minicells. In some embodiments, the CD1d-restricted iNKT cell antigen and the antineoplastic agents are comprised in separate intact bacterially-derived minicells. In some embodiments, the CD1d-restricted iNKT cell antigen and the antineoplastic agents are comprised in the same intact bacterially-derived minicell. In some embodiments, tact, bacterially derived minicells or killed bacterial cells that encapsulate CD1d-restricted iNKT cell antigen are administered separately from the antineoplastic agent or therapy. In some embodiments, the CD1d-restricted iNKT cell antigen and the antineoplastic agents are comprised in the same intact bacterially-derived minicell. In some embodiments, tact, bacterially derived minicells or killed bacterial cells that encapsulate CD1d-restricted iNKT cell antigen are administered simultaneously with the antineoplastic agent or therapy. In some embodiments, tact, bacterially derived minicells or killed bacterial cells that encapsulate CD1d-restricted iNKT cell antigen are administered in the same composition with the antineoplastic agent. In some embodiments, the intact, bacterially derived minicells or killed bacterial cells that encapsulate CD1d-restricted iNKT cell antigen are administered as separate compositions with the antineoplastic agent. In another aspect, the compositions comprising the encapsulated CD1d-restricted iNKT cell antigen or antineoplastic agent used to treat a subject suffering from cancer further comprises a pharmaceutically acceptable carrier.

In another aspect, the methods disclosed herein are useful for treating a subject suffering from a cancer, wherein the subject is a human, a non-human primate, a dog, a cat, a cow, a sheep, a horse, a rabbit, a mouse, or a rat.

In another aspect, the methods disclosed herein are useful for treating a cancer disease. In some embodiment the cancer comprises a lung cancer, a breast cancer, a brain cancer, a liver cancer, a colon cancer, a pancreatic cancer, or a bladder cancer.

In some embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström's macroglobulinemia; or Wilms' tumor.

In some embodiments, the brain cancer or tumor is selected from the group consisting of brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma.

VIII. Definitions

Technical and scientific terms used herein have the meanings commonly understood by one of ordinary skill in the art to which the present invention pertains, unless otherwise defined. Materials, reagents and the like to which reference is made in the following description and examples are obtainable from commercial sources, unless otherwise noted.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Individual," "subject," "host," and "patient," used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Cancer," "neoplasm," "tumor," "malignancy" and "carcinoma," used interchangeably herein, refer to cells or tissues that exhibit an aberrant growth phenotype characterized by a significant loss of control of cell proliferation. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. The methods and compositions of this invention particularly apply to precancerous, malignant, pre-metastatic, metastatic, and non-metastatic cells.

The terms "treatment," "treating," "treat," and the like refer to obtaining a desired pharmacological and/or physiologic effect in a tumor patient. The effect can be prophylactic in terms of completely or partially preventing tumor or symptom thereof and/or can be therapeutic in terms of a partial or complete stabilization or cure for tumor and/or adverse effect attributable to the tumor. Treatment covers any treatment of a tumor in a mammal, particularly a human. A desired effect, in particular, is tumor response, which can be measured as reduction of tumor mass or inhibition of tumor mass increase. In addition to tumor response, an increase of overall survival, progress-free survival, or time to tumor recurrence or a reduction of adverse effect also can be used clinically as a desired treatment effect.

As used herein, the term "administering" includes directly administering to another, self-administering, and prescribing or directing the administration of an agent as disclosed herein.

As used herein, the phrases "effective amount" and "therapeutically effective amount" mean that active agent dosage or plasma concentration in a subject, respectively, that provides the specific pharmacological effect for which the active agent is administered in a subject in need of such treatment. It is emphasized that an effective amount of an active agent will not always be effective in treating the conditions/diseases described herein, even though such dosage is deemed to be an effective amount by those of skill in the art.

As used herein, the term "active agent" is any small molecular drug, protein, functional nucleic acid, or polynucleic acid encoding a functional nucleic acid that is useful for treating a subject. The active agent can be any of the antineoplastic drugs, functional acids, interferon type I agonists or type II agonists described herein.

The phrase "pharmaceutically acceptable" is employed herein to refer to those compounds, materials, compositions, and/or dosage forms which are, within the scope of sound medical judgment, suitable for use in vivo without excessive toxicity, irritation, allergic response, or other problem or complication, commensurate with a reasonable benefit/risk ratio.

The term "endocytosis" encompasses (1) phagocytosis and (2) pinocytosis, itself a category inclusive of (2a) macropinocytosis, which does not require receptor binding, as well as of (2b) clathrin-mediated endocytosis, (2c) caveolae-mediated endocytosis and (2d) clathrin-/caveolae-independent endocytosis, all of which tend to access the late-endosome/lysosome pathway. The interaction between the ligand on a minicell and a mammalian cell surface receptor, the present inventors discovered, activates a particular endocytosis pathway, involving receptor mediated endocytosis (rME) to the late-endosomal/lysosomal compartment. By virtue of such an endocytosis pathway, the present inventors further discovered that the minicells were able to release their payload into the cytoplasm of the target mammalian cell. In the event the payload is an encoding nucleic acid, the nucleic acid not only is not completely degraded in the late-endosomal/lysosomal compartment, but also is expressed in the target mammalian cell.

The following examples are illustrative only, rather than limiting, and provide a more complete understanding of the invention. The examples demonstrate that drug resistant tumor cells can be effectively treated in-vivo by (1) administration of targeted recombinant minicells carrying RNAi sequences designed to reduce or eliminate expression of drug resistance encoding gene(s), and (2) administration of targeted, drug-packaged minicells carrying the drug to which the cancer cells are made sensitive.

The following examples are provided to illustrate the present invention. It should be understood, however, that the invention is not to be limited to the specific conditions or details described in these examples. Throughout the specification, any and all references to a publicly available document, including a U.S. and/or international patent or patent application publication, are specifically incorporated by reference.

EXAMPLES

Example 1. $EDV_{\alpha GC}$ Treatment of JAWSII Cells and the Subsequent Surface Presentation of αGC Through CD1d Ligand This example contrasts encapsulated delivery of αGC via intact bacterial minicells and free αGC against cancer cells.

Cells used: Mouse immature monocytes JAWSII (ATCC® CRL-11904™).

Preparation Perfecta3D 96-Well Hanging Drop Plate: The upper and lower side tray reservoirs of the 3D hanging drop plates were filled with melted 1% agarose using a P1000 pipette (1 g agarose dissolve in 100 ml of water, dissolved in microwave and allowed to cool to ~50° C.). The plates were allowed to dry and settle at room temperature for at least 30 min. The outside wells of the hanging drop plate were then filled with 50 μl of sterile cell culture media (without cells)/well.

Treatment of JAWSII spheroids with $EDV_{\alpha GC}$: JAWSII cells were treated with 1000 ng/ml aGC (positive control); empty minicells and minicells$_{\alpha GC}$ compared to untreated cells and collected at 8h, 16h, 24h and 48h post-treatment (FIGS. 8A-8D).

Dissociation of JAWSII cells into single-cell suspensions: JAWSII cells were grown as semi-suspension cultures in T25 or T75 flasks. The culture media was carefully collected into a sterile 50 ml tube by pipetting using a pipette-aid and the culture surface of the flask was washed 2× with 5 ml of sterile PBS, and collected in the same sterile 50 ml tube after each wash. The adherent cells were collected by the addition of 5 ml of 0.25% trypsin/EDTA and incubated at 37° C. for 3 min or until all the cells were lifted from the surface of the flask. The lifted cells were carefully broken up into single cells by gentle pipetting using a pipette-aid and transferred into the sample sterile 50 ml tube used in previous steps. The cell suspension was then centrifuged at 300 g for 7 min and the supernatant was carefully decanted. The cell pellet was dissociated by flicking the bottom of the tube with a finger and resuspended in 5 ml of pre-warmed JAWSII culture media. The cell suspension was further dissociated into single cells by careful pipetting using a pipette-aid. To determine the cell number, 10 μl of the cell suspension was mixed with 10 μl of trypan blue solution and analyzed using an EVE automated cell counter.

Initial treatment preparation: 6 hanging drop suspension samples were used for each treatment group per time point. $5 \times 10^4$ JAWSII cells and $5 \times 10^8$ minicells (1:1000 minicell to cell ratio) were used for each treatment sample and cultured in JAWSII cell culture media in a total volume of 50 μl. Extra untreated samples were prepared for isotype controls. The appropriate amount of minicells were pelleted by centrifugation at 12,000 g for 7 min and the supernatant was carefully removed by pipetting. Appropriate amount of live JAWS cells (based on the cell count from the previous section) were added to the pelleted minicells. The minicells were then dissociated into single—minicells—cell suspensions by gentle pipetting. The final volume of each sample was then made up by the addition of sterile culture media. For the untreated and aGC treated samples, $5 \times 10^4$ JAWSII cells were used for each sample and cultured in JAWSII cell culture media in a total volume of 50 μl. Appropriate amount of live JAWSII cells were transferred into Eppendorf tubes. The final volume of each sample was then made up by the addition of sterile culture media. 1000 ng/mL of αGC was added directly into the cell suspension for the JAWSII cells treated with 1000 ng/ml αGC (positive control) treatment group. The samples were then carefully seeded into each well of the hanging drop plates at 50 μl of treatment suspension/well and incubated at 37° C. at 5% $CO_2$ until collection.

Staining the treated JAWSII cells with anti-alpha GalCer:mCD1d complex monoclonal antibody: The entire content of each hanging drop well was carefully collected using a P200 pipette and transferred into an Eppendorf tube. A total of 6 samples were collected for each treatment group into 1 tube. 1:1000 PE conjugated anti-mouse alpha GalCer:mCD1d complex monoclonal antibody and 1:1000 PE conjugated mouse IgG1 isotype control were added into appropriate samples and mixed by gentle vortexing. GalCer:mCD1d monoclonal antibody binds to the cell surface exposed portion of the GalCer:CD1d complex. The samples were then incubated at room temperature for 20 min in the dark. Samples were then pelleted by centrifugation at 350 g for 5 min. The supernatant was removed by careful pipetting and the pellets were re-suspended and washed once in 500 μL FACS buffer. The cells were then collected by centrifugation at 350 g for 5 min, resuspended in 250 μL FACS buffer and transferred into FACS tubes. 1 μL of DAPI was added into each sample and mixed by gently swirling of the tubes. The samples were then analyzed using a Gallios flow cytometer.

Figure 8B:
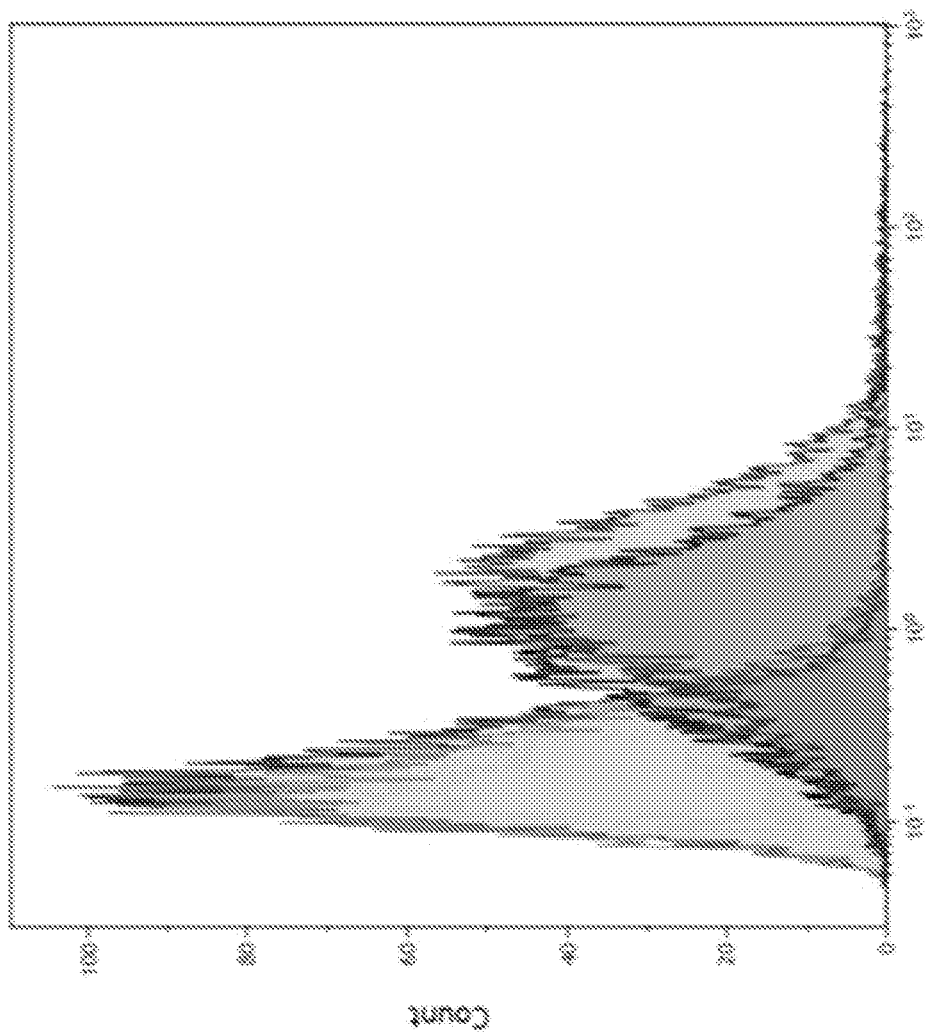
Figure 8D:
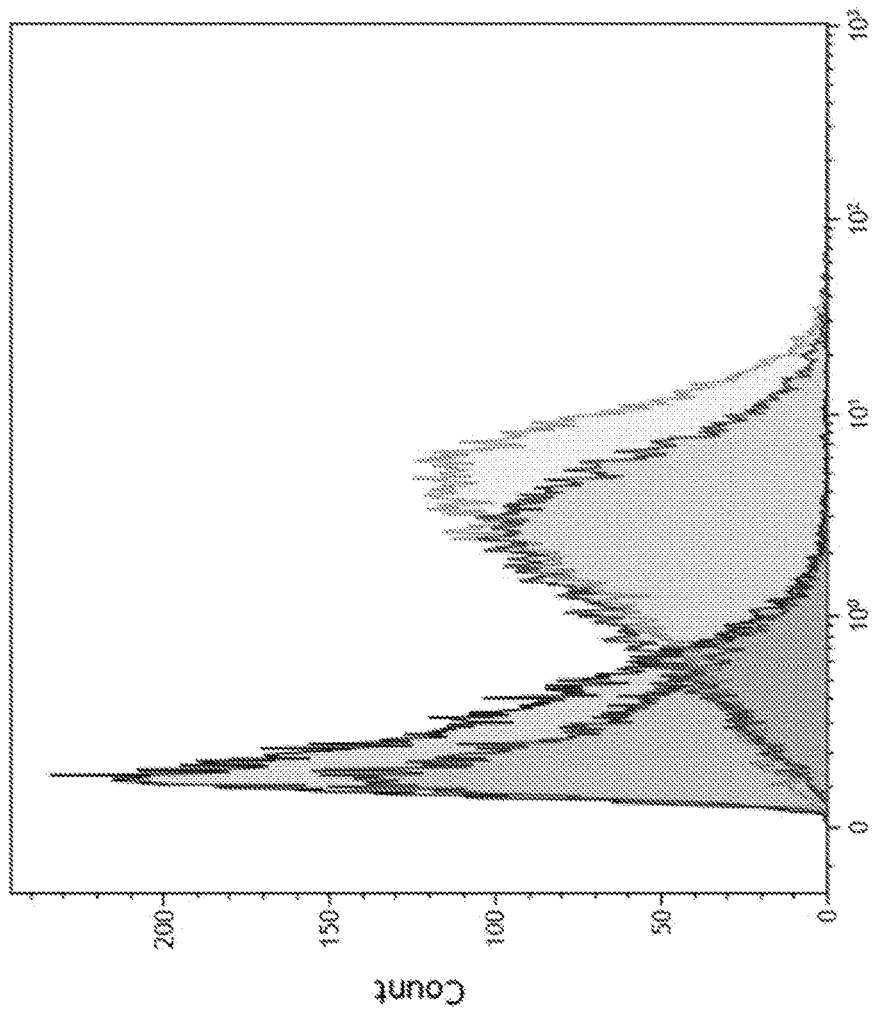
Figure 8E:
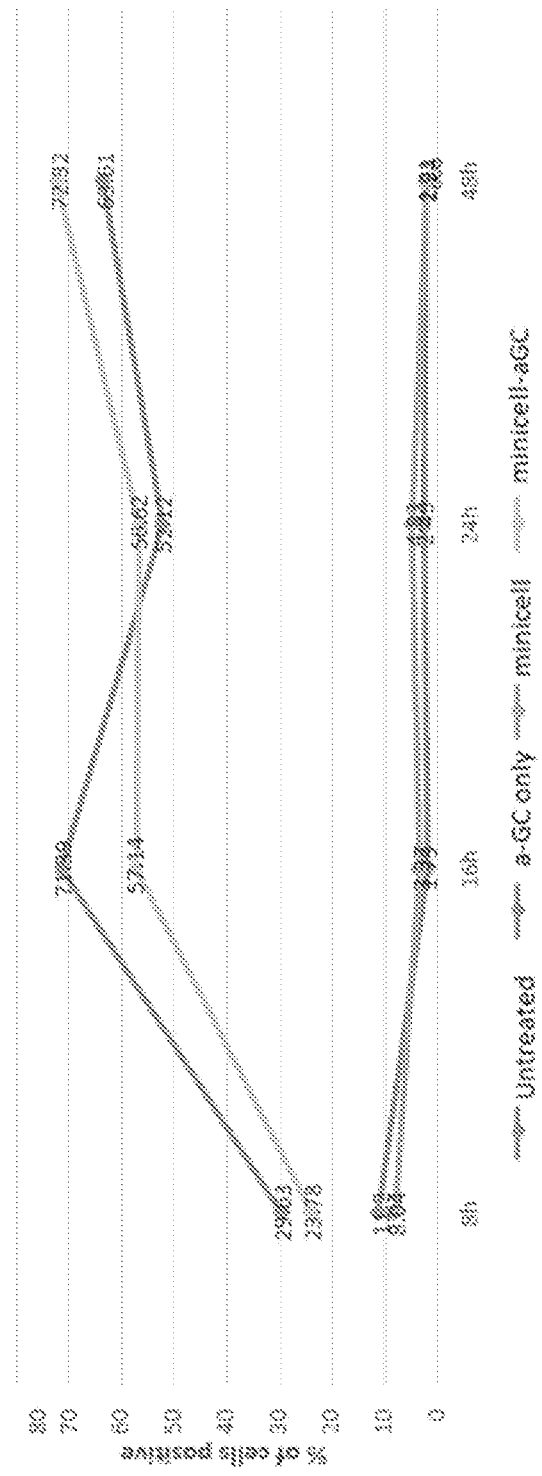

Results: Flow cytometry data (FIG. 8) showed a clear shift after staining with anti-GalCer:mCD1d for JAWSII cells treated with minicells$_{\alpha-GC}$ and with free α-GC compared to JAWSII cells treated with minicells alone and untreated. This positive staining, confirms the successful delivery of α-GC by minicells to JAWSII cells and subsequent antigen presentation on the cell surface by the CD1d molecule which presents glycolipids on the cell surface. Presentation of α-GC is a crucial step which leads to receptor recognition by invariant NKT cells triggering off a type II IFN cascade essential in anti-tumor activity.

Example 2: In Vivo Studies Using Combination Treatment of $^{Ep}$Minicell$_{Dox}$ and Minicell$_{\alpha-GC}$ in a Syngeneic Mouse Model ($^{Ep}$CT26 Murine Colon Cancer in Balb/c Mice)

This example illustrates the efficacy of minicell contained therapeutic and minicell contained CD1d-restricted iNKT cell antigen (e.g., α-GalCer) against tumors. This result demonstrates that combination of and encapsulated CD1d-restricted iNKT cell antigen with an antineoplastic agent can be used to effectively treat tumors.

Mice and treatments (Experiments 1-3): Balb/c mice, female, 6-7 weeks old were obtained from the Animal Resources Company in Western Australia. The mice were acclimatized for one week before the experiments commenced. CT26 cells (mouse colon cancer) were stably transformed with a plasmid expressing EpCAM antigen and a stable clone (Epclone 12.1) was established. This clone expressed EpCAM on the surface of the cells. All animal experiments were performed in compliance with National Health and Medical Research Council, Australia guidelines for the care and use of laboratory animals, and with EnGeneIC Animal Ethics Committee approval.

CT26 (Epclone 12. 1) isografts were established by injecting 2×105 cells per 100 μl PBS subcutaneously on the left flank of each mouse. The tumors grew to the ~125 mm3 starting volume within 8 days post implantation. The mice were randomly distributed into groups with 8 mice for each treatment group. Tumors were treated with EpminicellDox, minicellα-GC and EpminicellDox+minicellα-GC (combination) compared to saline treatment alone.

Dosing was carried out 3× per week for 2 weeks. EpminicellDox was dosed at 1×109 minicells per dose in single and in combination treatments. minicellα-GC was dosed at 1×107 in experiments 1 (FIG. 3) and 3 (FIG. 5) and 1×108 in experiment 2 (FIG. 3), where the saline group was also challenged when the tumor volume reached 800 mm3.

Results: All 3 experiments showed a marked halt in tumor progression for combination treatment groups receiving EpminicellDox+minicellα-GC compared to saline and EpminicellDox treatments. This result supports the theory of an immune adjuvant effect by the addition of minicellα-GC treatment to EpminicellDox Treatment with minicell$_{\alpha\text{-}GC}$ alone also showed a halt in tumor progression for all 3 experiments, though not to the extent of the combination treatment, as best seen in experiment 2.

Figure 4:
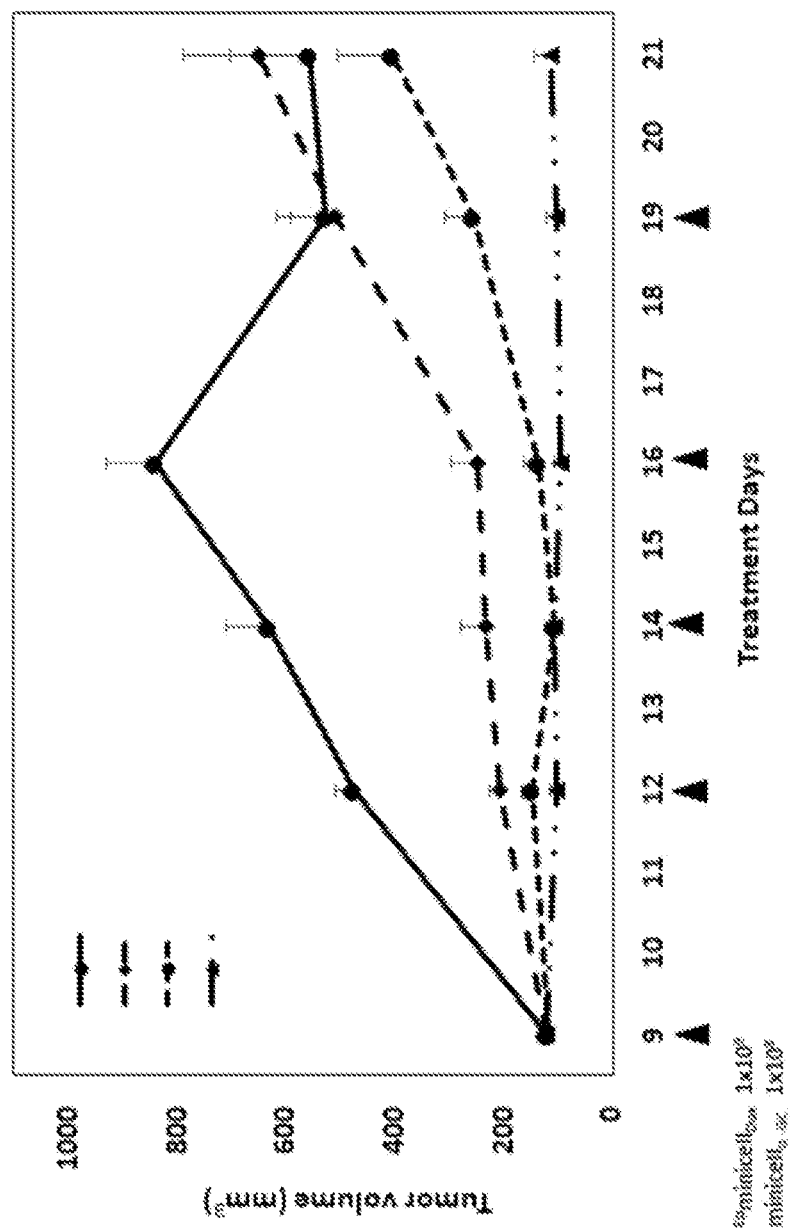
FIG. 4 shows combination treatment of $^{EP}$minicell$_{Dox}$ and minicell$_{\alpha\text{-}GC}$ is effective in reducing large tumors in Balb/c mice bearing CT26 isograft.
Figure 5:
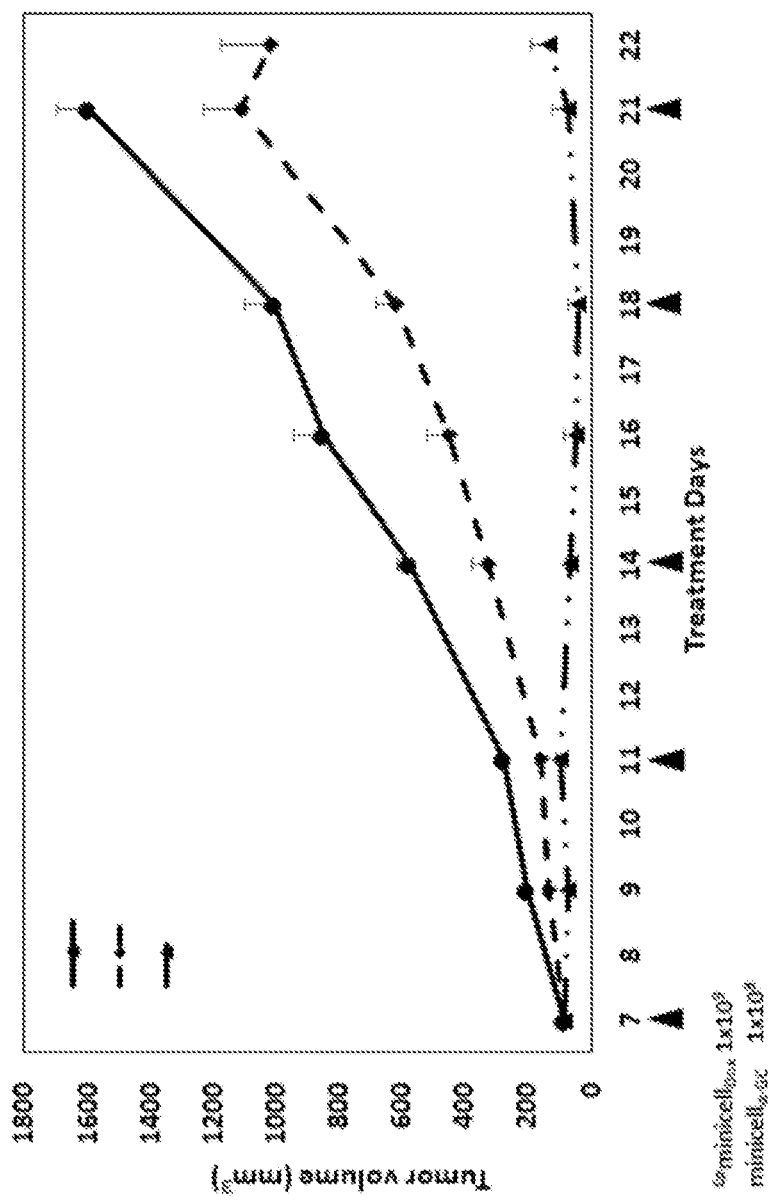
FIG. 5 shows effect of $^{Ep}$minicell$_{Dox}$ and minicell$_{\alpha\text{-}GC}$ on tumor regression in Balb/c mice with CT26 isograft.

In experiment 2, saline treated control tumors demonstrated dramatic tumor regression following a treatment change to drug and α-GC EDV mediated combination therapy (FIG. 4). Tumors that had reached 800 mm$^3$ dropped to below 600 mm$^3$ in 3 days before the experiment was terminated.

Figure 6A:
FIGS. 6A-F show different sized CT26 isografts treated with (FIGS. 6A and 6B) $^{Ep}$minicell$_{Dox}$ and minicell$_{\alpha\text{-}GC}$, (FIG. 6A=$_{Ep}$minicell$_{Dox}$ (1×10$^9$)+EDV$_{\alpha\text{-}GC}$ (1×10$^7$)), (FIG. 6B=$_{Ep}$minicell$_{Dox}$ (1×10$^9$)+EDV$_{\alpha\text{-}GC}$ (1×10$^6$)), FIG. 6C=saline, (FIGS. 6D and 6E) minicell$_{\alpha\text{-}GC}$ only (FIG. 6D=minicell$_{\alpha\text{-}GC}$(1×10$^7$)), (FIG. 6E=minicell$_{\alpha\text{-}GC}$(1×10$^6$)), and (FIG. 6F)$^{Ep}$minicell$_{Dox}$ only (FIG. 6F=$_{Ep}$minicell$_{Dox}$ (1×10$^9$)).
Figure 6B:
Figure 6C:
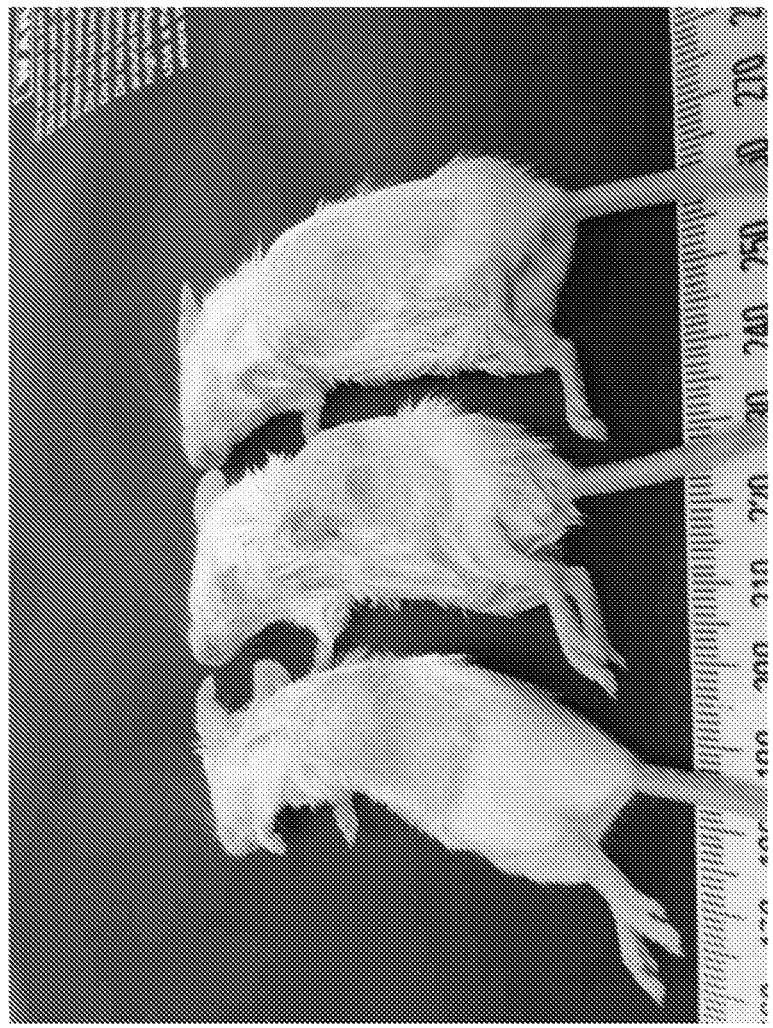
Figure 6D:
Figure 6E:
Figure 6F:

Dose evaluation of different sized tumors; Mice and treatments (Experiment 4): CT26 (Ep clone 12.1) isograft was established by injecting subcutaneously 2×10$^5$ cells/100 μl PBS into the left flank of female, 6-7 weeks old Balb/c mice. The tumors were grown to ~200-250 mm$^3$ or 600-800 mm$^3$ before treatments commenced. The mice were randomized into 6 groups, 3 mice per group. Mice received one dose only. Treatment groups included; Saline (FIG. 6C), $^{Ep}$minicell$_{Dox}$ (1×10$^9$) (FIG. 6F), minicellα-GC (1×10$^6$) (FIG. 6E), minicellα-GC (1×10$^7$) (FIG. 6D), $^{Ep}$minicell$_{Dox}$ 1×10$^9$+ minicell$_{\alpha\text{-}GC}$ (1×10$^6$) (FIG. 6B), $^{Ep}$minicell$_{Dox}$ (1×10$^9$)+ minicell$_{\alpha\text{-}GC}$ (1×10$^7$) (FIG. 6A).

Figure 7A:
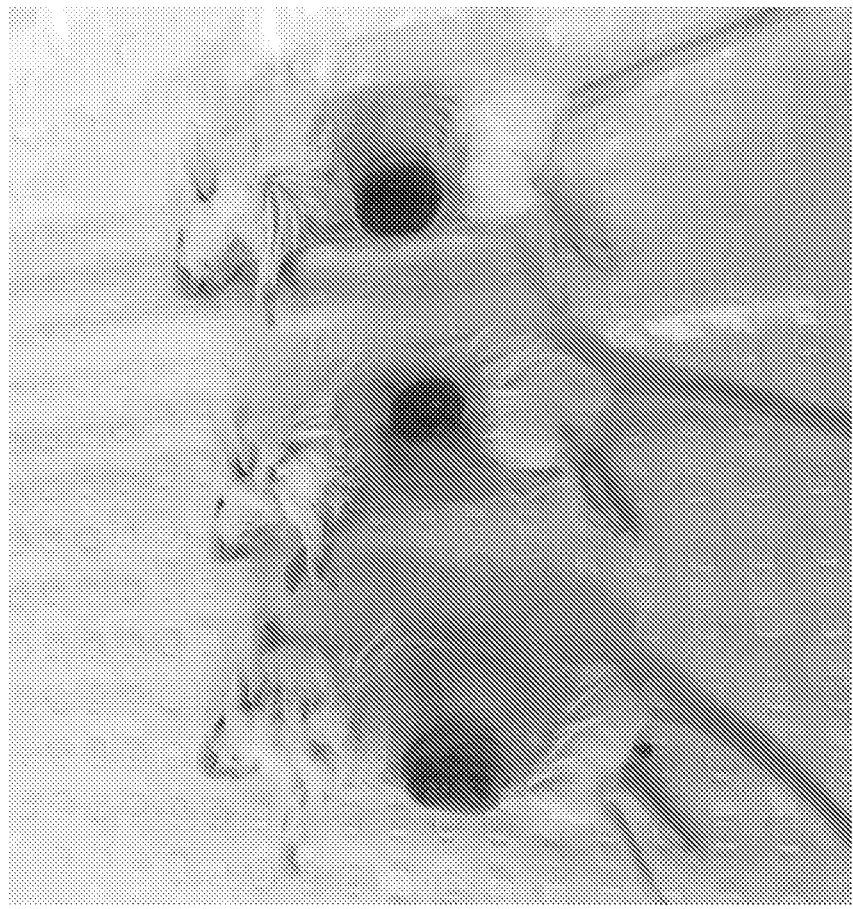
FIGS. 7A and 7B show different sized CT26 isografts treated with $^{Ep}$minicell$_{Dox}$ and minicell$_{\alpha\text{-}GC}$. CT26 (Epclone12.1) isograft; n=3; Tumor volume: 600-800 mm$^3$; Dose: 1; Sacrifice Time: 24 hrs.
Figure 7B:
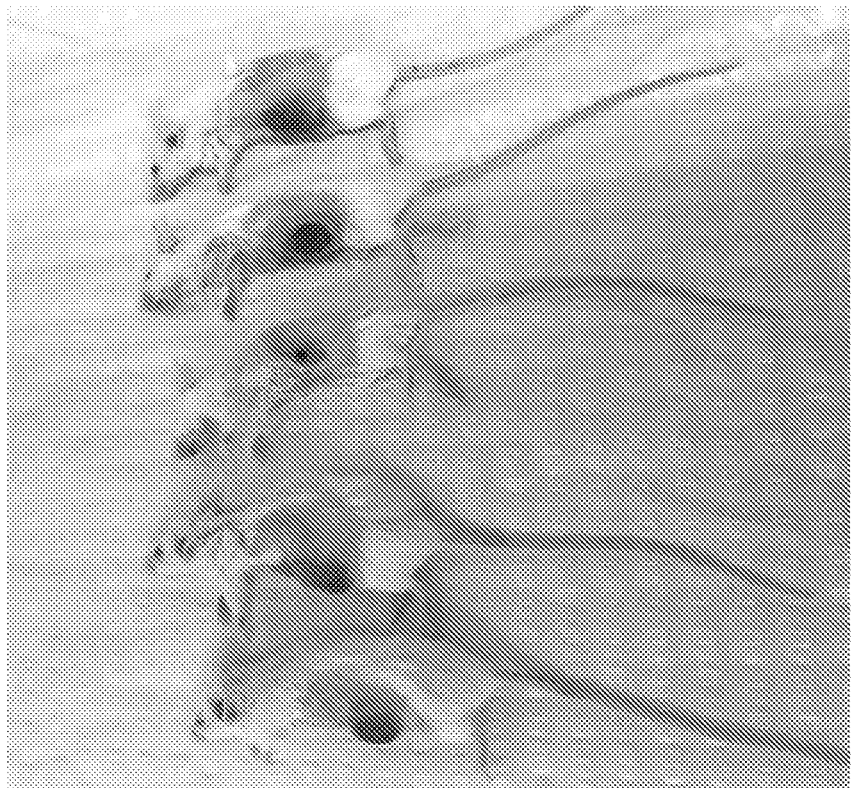

Mice were sacrificed at 24 hrs post treatment for 200-250 mm$^3$ (FIG. 6) tumors and at 16 hrs and 24 hrs for 600-800 mm$^3$ tumors (FIG. 7).

Results: The effect of minicell$_{\alpha\text{-}GC}$ dosing, alone and in combination, in CT26 syngeneic tumor bearing Balb/c mice was further investigated by treating different sized tumors with a single dose as described above. Interestingly it was found that in both, mice carrying tumors of 200-250 mm$^3$ as well as 400-600 mm$^3$, the tumors developed a marked necrosis (black color) within 24 hours of dosing. This effect was more pronounced in the larger tumors and not seen in the control groups.

In sum, these data show that a combination of an encapsulated CD1d-restricted iNKT cell antigen, such as α-GalCer with an antineoplastic agent demonstrates efficacy against tumors. This result demonstrates that the combination can be used to effectively treat tumors.

Example 3

This example describes secretion of cytokines IL-12 from dendritic cells/monocytes treated with minicell$_{\alpha\text{-}GC}$ and cytokines IFNγ, TNFα and IL-4 from iNKT cells exposed to these treated dendritic cells.

It is known that when antigen presenting cells (APCs) present α-galactosyl ceramide on their surface via CD1d, they secrete IL-12. Additionally, when these cells present the antigen to the iNKT cell receptor, the iNKT cells secrete a plethora of cytokines in particular, IFNγ, TNFα and IL-4. The aim of this experiment was to determine if JAWSII cells (mouse dendritic cell line) when co-incubated with minicell$_{\alpha GC}$ followed by co-incubation with iNKT cells would result in the secretion of these cytokines.

Methods

Isolation of iNKT Cells from C57 Mice

For the in vitro co-culture studies, iNKT cells were isolated from spleens and thymus of the C57 mice using the NK1.1+ iNKT cell isolation kit, mouse (Miltenyi Biotec) following the manufacturer's instructions. The purity of the isolated iNKT cells were determined by further staining the cells for the expression of CD3 and NK1.1 and analysed using FACS.

JAWSII cells were treated with minicell$_{\alpha GC}$ in a 96-well Perfecta3D hanging drop plate (Sigma). The cultures were then incubated for 48h at 37° C. with 5% CO$_2$ and supernatant was collected by centrifugation. The supernatant was then used for ELISA analysis for IL-12 secretion.

JAWSII cells presenting aGC as delivered by the initial treatment with minicell$_{\alpha GC}$ were seeded in a 96-well round bottom plate and co-cultured with iNKT cells isolated from C57 mice at 1:2 iNKT to JAWSII ratio in AIM V serum free medium (Thermo Fisher Scientific). The supernatant was then collected for ELISA analysis for IFNγ, TNFα and IL-4.

The levels of IL-12p40, IFN-γ, TNFα, and IL-4 in the culture supernatants were measured by standard sandwich enzyme-linked immunosorbent assay (ELISA) from R&D Systems according to manufacturer's instructions.

Figure 9:
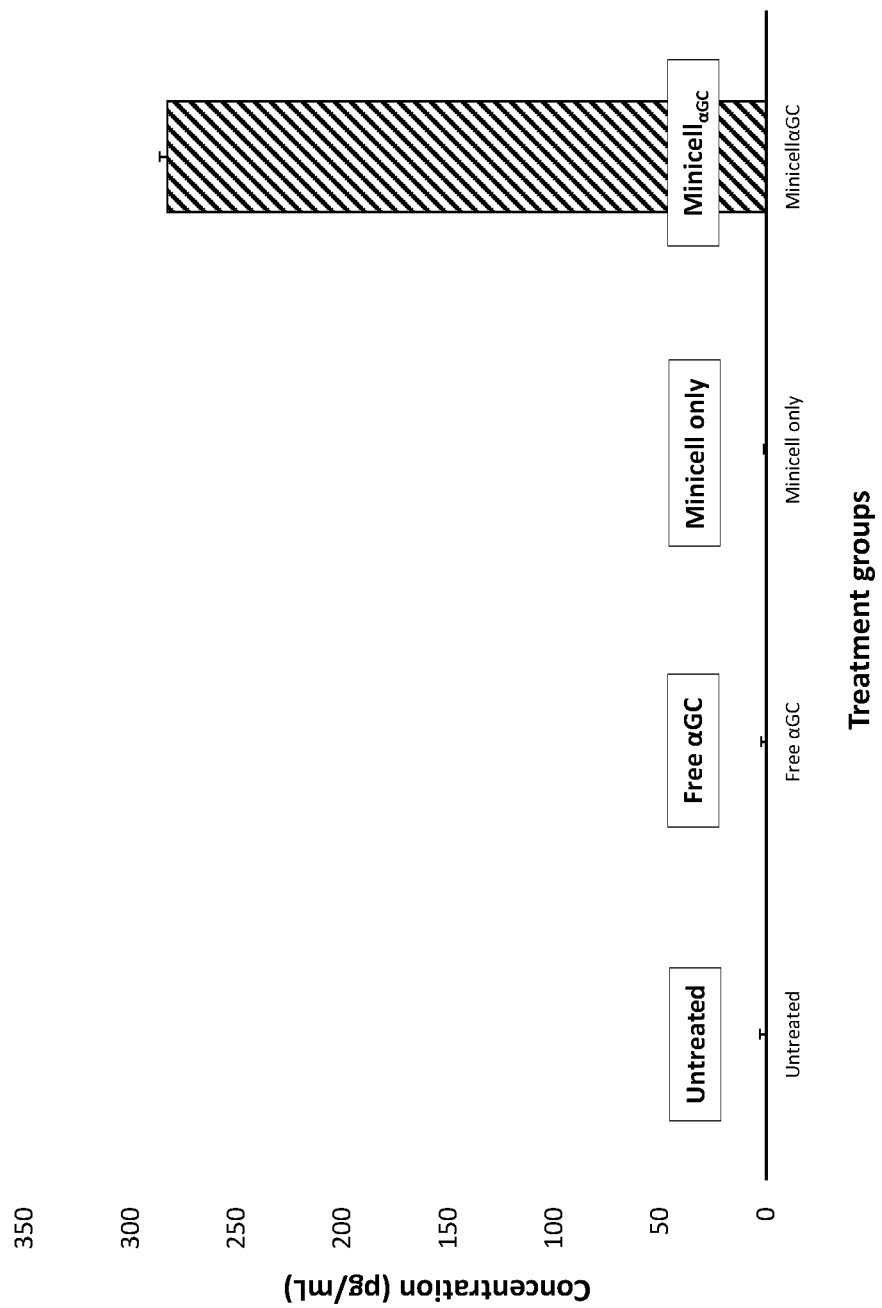
FIG. 9 shows IL-12 production by JAWSII cells treated with EDV$_{aGC}$ at 48h post-treatment.
Figure 10:
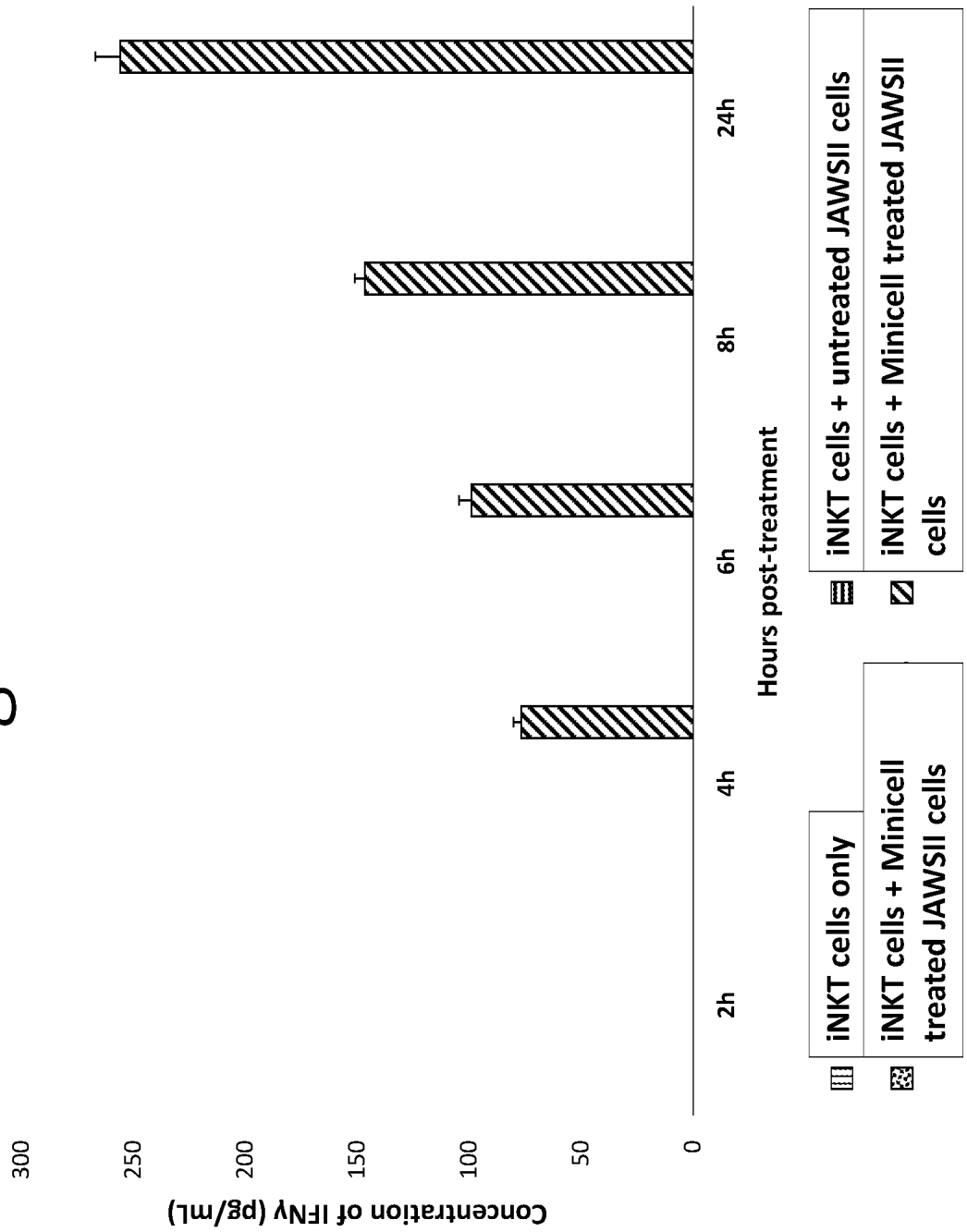
FIG. 10 shows concentrations of IFNγ secreted by iNKT cells co-cultured with JAWSII cells treated with EDV$_{\alpha GC}$.
Figure 11:
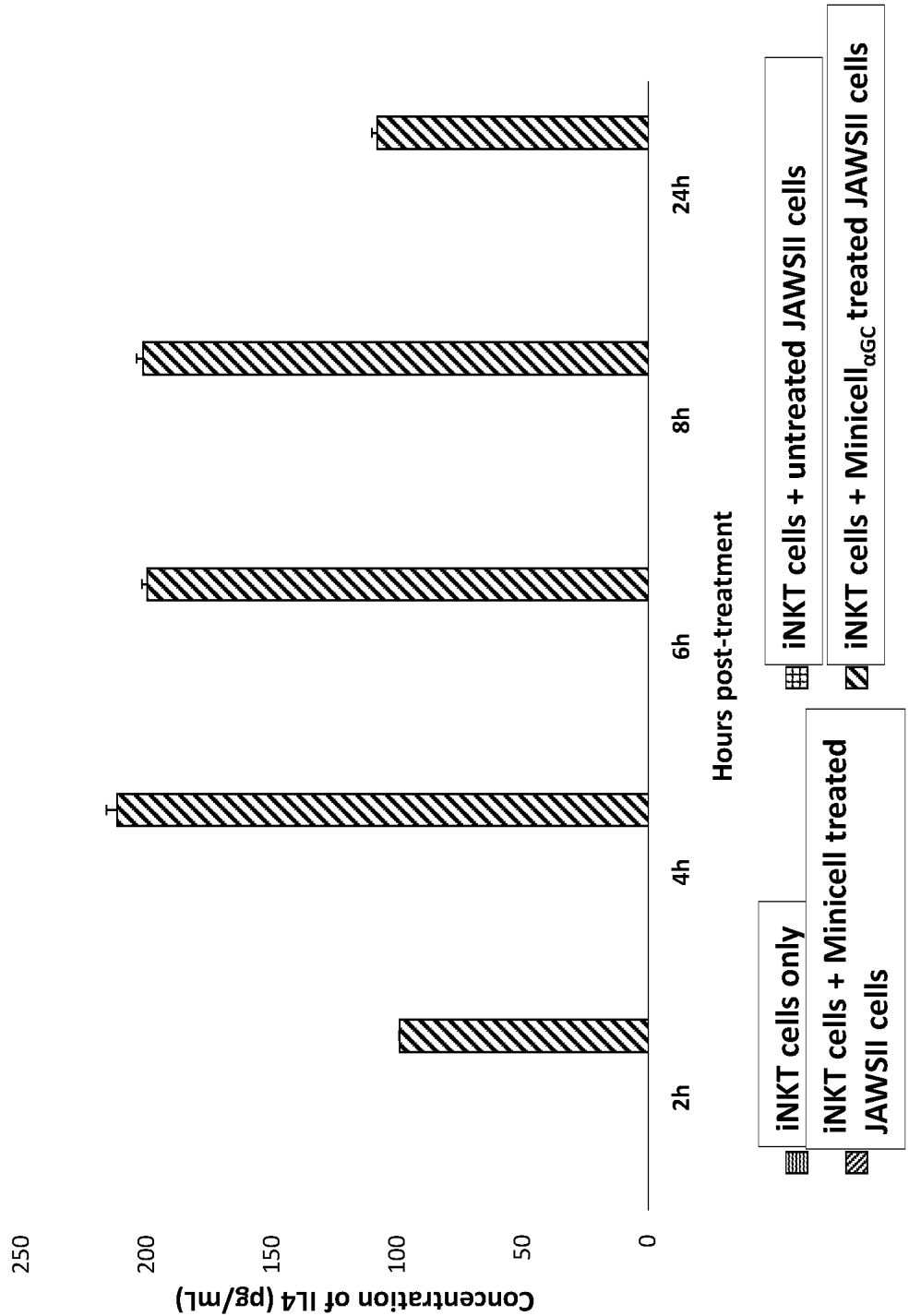
FIG. 11 shows concentrations of IL4 secreted by iNKT cells co-cultured with JAWSII cells treated with EDV$_{\alpha GC}$.
Figure 12:
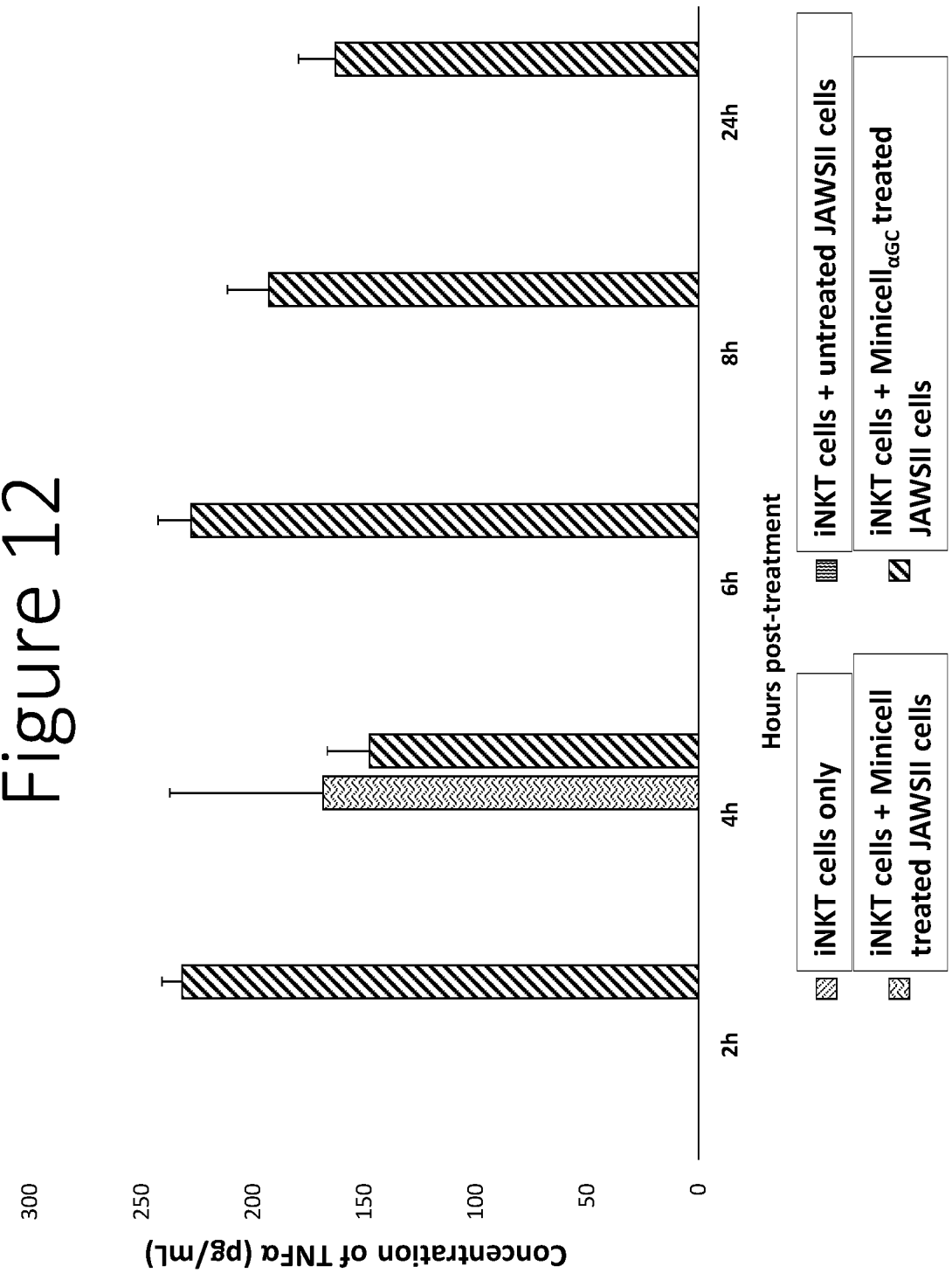
FIG. 12 shows concentrations of TNFα secreted by iNKT cells co-cultured with JAWSII cells treated with EDV$_{\alpha GC}$.
Figure 13:
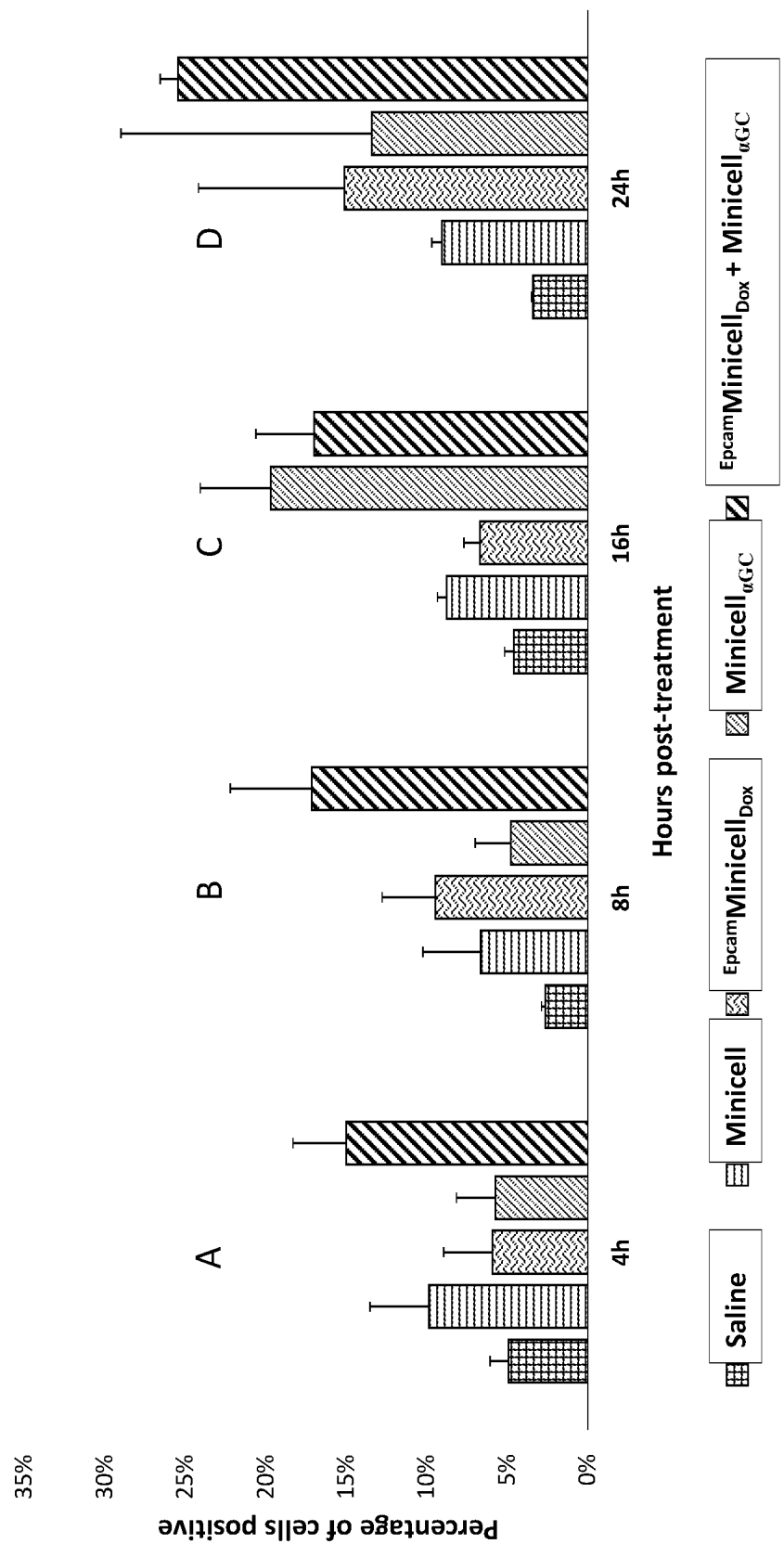
FIGS. 13A-D show the percentage of activated DCs in the spleen for five different tested compositions: saline, minicell, $^{Epcam}$Minicell$_{Dox}$, Minicell$_{\alpha GC}$, and $^{Epcam}$Minicell$_{Dox}$+Minicell$_{\alpha GC}$ (FIG. 13A=4 hrs.

The results showed that JAWSII cells treated with minicell$_{\alpha GC}$ resulted in a highly significant secretion of IL-12 within 48 hrs (FIG. 9). Coincubation of the minicell$_{\alpha GC}$ treated JAWII cells with iNKT cells resulted in a highly significant secretion of all three cytokines, IFNγ, TNFα and IL-4 (FIGS. 10, 11, and 12), suggesting that the minicells successfully delivered the aGC to the JAWSII cells, and that the aGC was displayed on the cell surface via CD1d, and that the iNKT cell surface receptor recognised the CD1d/aGC complex on the surface of JAWSII cells.

Example 4

This example describes an increase in activated dendritic cells in the spleen of mice treated with $^{EpCAM}$minicell$_{Dox}$+ minicell$_{\alpha\text{-}GC}$.

Methods:
Spleen and Thymus Dissociation

Immediately after euthanasia, the dissected spleen and thymus were transferred to the Dounce Homogeniser in freshly prepared media (10% FBS into sterile RPMI-1640 medium) by directly emptying the contents into the tube of the glass homogeniser. The organs were then gently broken down by using the glass plunger with 3-4 passes. The homogenised organs were then transferred into a 50 mL centrifuge tube through a 70 uM mesh strainer in media. The glass homogeniser was then washed with 4 mL of RPMI-1640 medium (serum free) and the content was then again passed through the same 70 uM mesh strainer into the centrifuge tube. The tube was then centrifuged at 330 g for 10 mins before resuspending the cell pellet in 4 mL of RPMI-1640 medium (serum free). Red Blood Cells were lysed using Red Blood Cell Lysis Buffer Hybri-Max (Merk R7757-100 mL) following manufacturer's instructions. The cells were then re-suspended in 5 mL of cold sterile autoMACS running buffer (Miltenyi) and passed through a 70 uM mesh strainer into a 50 mL centrifuge tube before proceeding to cell counting.

FACS Analysis

Single cell preparations of the isolated organs were diluted in $1\times10^6$ cells/100 mL FACS buffer. The cells were then strained with the appropriate antibodies as displayed in Table 1 below. Unstained and cells stained with single antibodies were used as negative controls. All samples and reagents were kept cold on ice and DAPI was used to differentiate live/dead cells.

TABLE 1

| Cell types | Markers |
| --- | --- |
| CD8+/CD4+ T-cells | CD4, CD3, CD8, CD45 |
| Activated DCs | CD45, CD370, CD86, CD40 |
| iNKT cells | CD45, CD3, CD49b |

The prepared samples were run on a Gallios flow cytometer (Beckman) and analysis was conducted using the Kaluza analysis software (Beckman) Any spectral spillover between the channels were minimised/removed by analysing single-antibody staining using the compensation functions built into the Kaluza analysis software.

Female Balb/c mice, 6-7 weeks old were obtained from the Animal Resources Company in Western Australia. The mice were acclimatized for one week before the experiments commenced. CT26 cells (mouse colon cancer) were stably transformed with a plasmid expressing EpCAM antigen and a stable clone (Ep clone 12.1) was established. This clone expressed EpCAM on the surface of the cells. All animal experiments were performed in compliance with National Health and Medical Research Council, Australia guidelines for the care and use of laboratory animals, and with EnGeneIC Animal Ethics Committee approval.

CT26 (Epclone 12. 1) isografts were established by injecting $2\times10^5$ cells per 100 µl PBS subcutaneously on the left flank of each mouse. The tumors grew to the ~125 mm³ starting volume within 8 days post implantation. The mice were randomly distributed into groups with 8 mice for each treatment group. Mice were treated intravenously (tail vein injection) with $^{EpCAM}$minicell$_{Dox}$, minicell$_{\alpha-GC}$ and $^{EpCAM}$minicell$_{Dox}$+minicell$_{\alpha-GC}$ (combination) as compared to saline treatment alone.

The mice received a single dose at the beginning of the experiment. $^{EpCAM}$minicell$_{Dox}$ was dosed at $1\times10^9$ minicells per dose in single and in combination treatments. minicell$_{\alpha-GC}$ was dosed at $1\times10^7$.

For immune cell analysis, the mice were sacrificed and total splenocytes were isolated at 4h, 8h, 16h and 24 h after the initial dose. The cells were stained for the presence of activated dendritic cells (CD86+ CD40+) and the population was analysed using FACS.

Results

The result showed (FIGS. 13A-D) that at 4 hrs, 8 hrs, 16 hrs and 24 hrs post treatment with $^{EpCAM}$minicell$_{Dox}$+minicell$_{\alpha-GC}$ there was a significant increase in the activated dendritic cell (CD86+ CD40+) population in the spleen of the mice.

Example 5

The purpose of this example was to evaluate infiltration of immune cells into the tumor microenvironment following treatment of mouse xenografts with $^{EpCAM}$minicell$_{Dox}$+minicell$_{\alpha-GC}$.

This example illustrates the efficacy of minicell contained therapeutic and minicell contained CD1d-restricted iNKT cell antigen (e.g., α-GalCer) against tumors. This result demonstrates that combination of minicell-encapsulated CD1d-restricted iNKT cell antigen with tumor cells surface targeted, antineoplastic agent-packaged minicells can be used to effectively provoke a significant infiltration of activated cells of the immune system into the tumor.

CT26 xenografted mice from Example 4 were sacrificed and the tumor mass was removed and all the cells were extracted following tumor dissociation as described below.

Immediately after euthanasia, the xenografts were excised and placed in serum-free media (RPMI 1640 or DMEM). Tumour Dissociation Kit for mouse (Miltenyi Biotec) was used to dissociate tumour tissues into single-cell suspensions. Initially, tumour tissues were finely chopped using sterile blades. Tissues were placed in a gentleMACS C Tube (Miltenyi Biotec) containing the enzyme mix, which was prepared according to the manufacturer's protocol. For CT26 xenografts, gentleMACS Program for soft/medium tumor was selected on Octo Dissociator with Heaters (Miltenyi Biotec). Following incubation on the dissociator, cell suspensions were applied through a MACS SmartStrainer (Miltenyi Biotec) and dissociated cells were collected.

The cells were stained for CD45+ cells which identifies all cells of the immune system e.g. macrophages, dendritic cells and T cells. The samples were analysed by FACS.

Results

Figure 14:
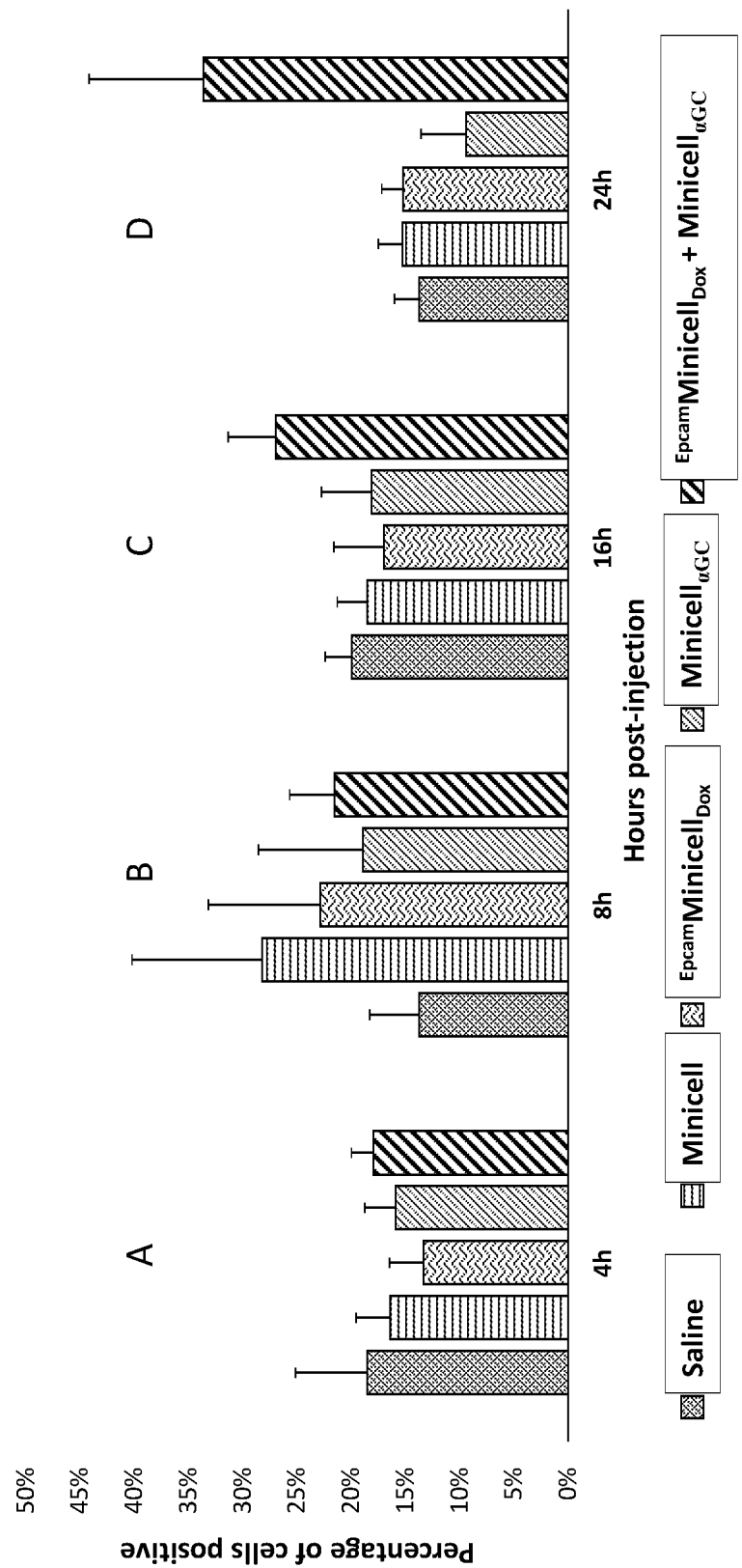
FIGS. 14A-D show the percentage of CD45+ cells within the tumours during the course of the in vivo treatment for five different tested compositions: saline, minicell, $^{Epcam}$Minicell$_{Dox}$, Minicell$_{\alpha GC}$, and $^{Epcam}$Minicell$_{Dox}$+Minicell$_{\alpha GC}$ (FIG. 14A=4 hrs.

The result showed (FIGS. 14A-D) that at 16 hrs (FIG. 14C) and 24 hrs (FIG. 14D), the tumors had a significant infiltration of cells of the immune system into the tumor only where mice were treated with the combination therapy $^{EpCAM}$minicell$_{Dox}$+minicell$_{\alpha-GC}$.

Example 6

The purpose of this example was to evaluate infiltration of cytotoxic T cells into the tumor microenvironment following treatment of mouse xenografts with $^{EpCAM}$minicell$_{Dox}$+minicell$_{\alpha-GC}$.

The tumors were excised from the mouse xenograft described in Examples 4 and 5 and the cells were isolated as described in Example 4. The cells were stained for CD45+ CD3+ CD8+ cells which identify cytotoxic T cells.

Results

Figure 15:
FIGS. 15A-D show the percentage of CD3+ CD8+ Cytotoxic T-cells within the tumour environment for five different tested compositions: saline, minicell, $^{Epcam}$Minicell$_{Dox}$, Minicell$_{\alpha GC}$, and $^{Epcam}$Minicell$_{Dox}$+Minicell$_{\alpha GC}$ (FIG. 15A=4 hrs.

The result showed (FIG. 15D) that at 24 hrs post treatment with $^{EpCAM}$minicell$_{Dox}$+minicell$_{\alpha-GC}$ there was a highly significant increase in the CD8+ cytotoxic T cells in the tumor microenvironment of the mice.

Figure 16:
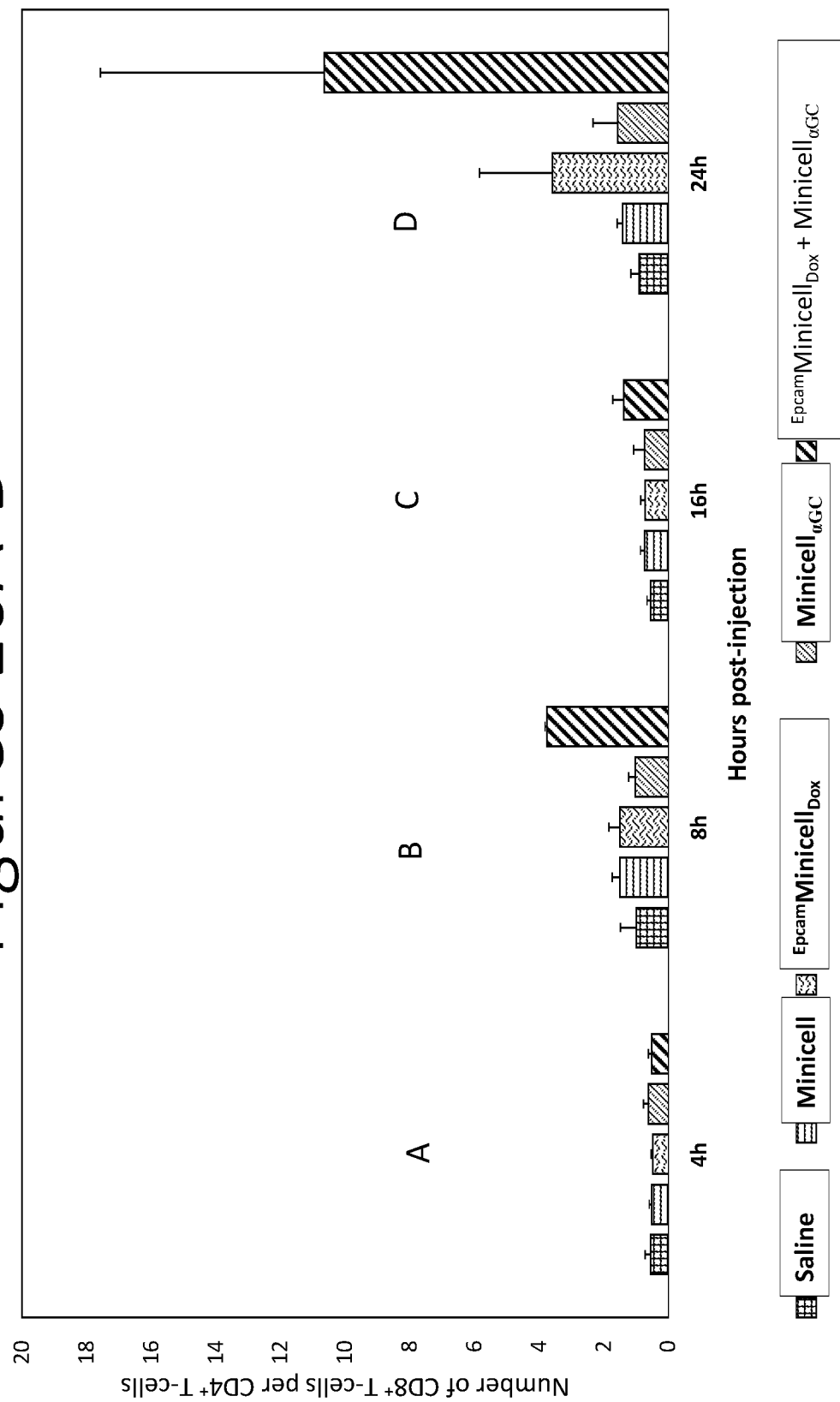
FIGS. 16A-D show the ratios between CD8+ and CD4+ T-cells within the tumour environment five different tested compositions: saline, minicell, $^{Epcam}$Minicell$_{Dox}$, Minicell$_{\alpha GC}$, and $^{Epcam}$Minicell$_{Dox}$+Minicell$_{\alpha GC}$ (FIG. 16A=4 hrs.

The ratio of CD8+ to CD4+ T cells was also calculated and the result showed (FIG. 16D) that there was a highly significant increase in CD8+:CD4+ ratio at 24 hrs after treatment with $^{EpCAM}$minicell$_{Dox}$+minicell$_{\alpha\text{-}GC}$.

Example 7

The purpose of this example was to evaluate the infiltration of iNKT cells into the tumor microenvironment following treatment of mouse xenografts with $^{EpCAM}$minicell$_{Dox}$+minicell$_{\alpha\text{-}GC}$.

Figure 17:
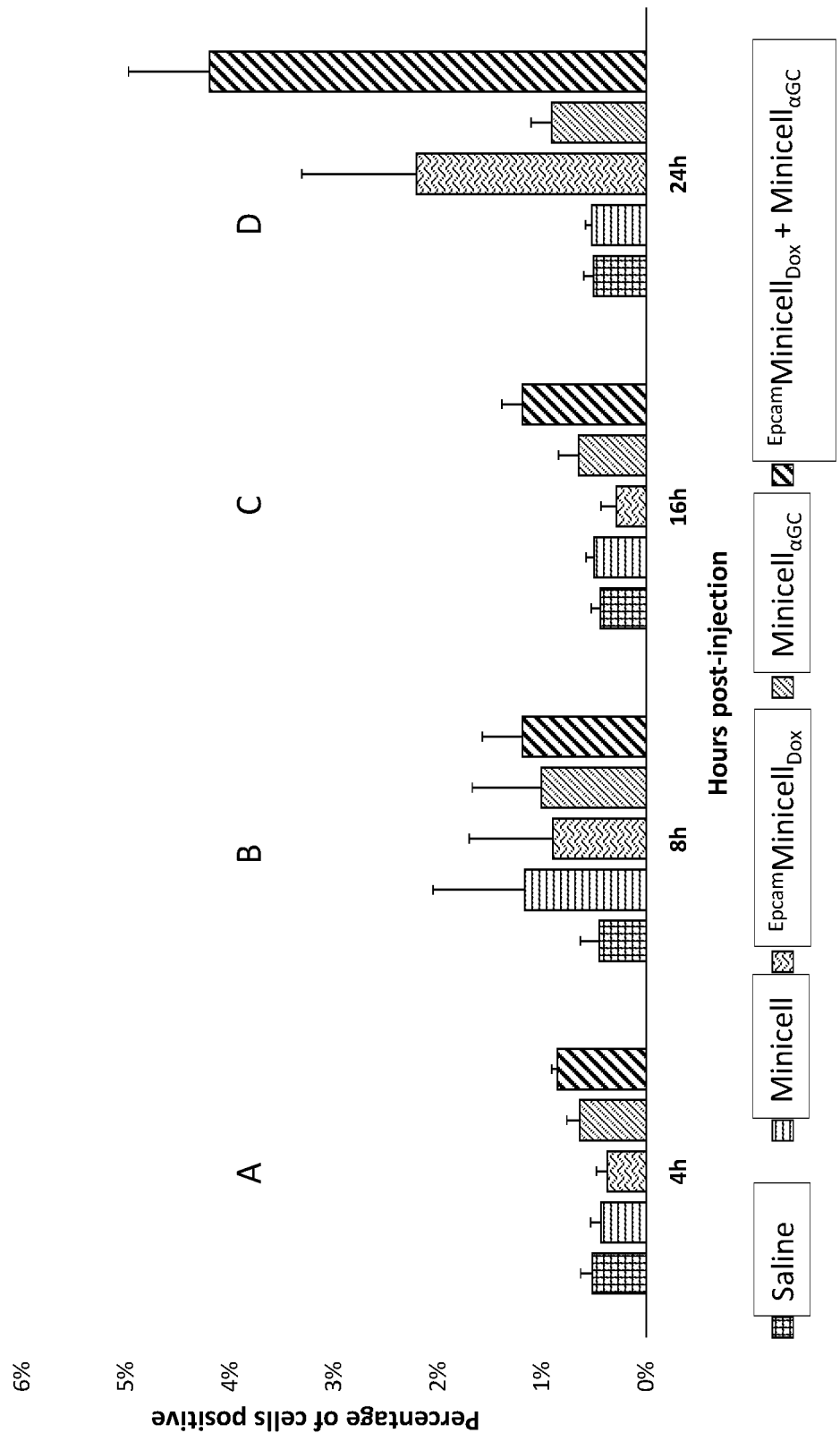
FIGS. 17A-D show the percentage of iNKT cells within the tumor environment for five different tested compositions: saline, minicell, EpcamMinicellDox, MinicellαGC, and EpcamMinicellDox+MinicellαGC (FIG. 17A=4 hrs.

The tumors were excised from the mouse xenograft described in Examples 4 and 5 and the cells were isolated as described in Example 5. The cells were stained for CD45+ CD3+ CD49B+ cells which identify iNKT cells.
Results The result showed (FIG. 17D) that at 24 hrs post treatment with $^{EpCAM}$minicell$_{Dox}$+minicell$_{\alpha\text{-}GC}$ there was a highly significant increase in the iNKT cells in the tumor microenvironment of the mice.

Example 8

The purpose of this example was to evaluate a significant increase in CD1d expression in the PBMC and dendritic cells following treatment of mouse xenografts with $^{EpCAM}$minicell$_{Dox}$+minicell$_{\alpha\text{-}GC}$.

Mouse xenograft study was carried out as described in Examples 4 and 5. In this experiment, another group of mice was added and this group received $^{EpCAM}$minicell$_{682}$+minicell$_{\alpha\text{-}GC}$. The drug PNU159682 (designated 682 in this study) is a nemorubicin derivative that is over 2,000 times more toxic than doxorubicin. Eight hours post-administration of the various treatments, peripheral blood mononuclear cells (PBMCs) were collected from the mouse xenograft described in Examples 4 and 5. RNAs were isolated from the collected specimens using RNeasy mini kit (Qiagen) following manufacturer's instructions. The quality and quantity of the RNA was determined by measuring the absorbance at 260 nm and 280 nm. A 260/280 ratio of 1.8 or above was considered acceptable.

cDNA synthesis was conducted using Superscript Vilo (Thermo Fisher Scientific) per manufacturer's protocol. 10 ng of cDNA was used for each qPCR reaction.

qPCR were conducted using a 7500 Fast Real-Time PCR system (Applied Biosystems) with SYBR green dye. The results were calculated using the delta delta CT method against 2 housekeeping genes beta-2-microglobulin (B2M) and glucuronidase, beta (GUSB).

Figure 18:
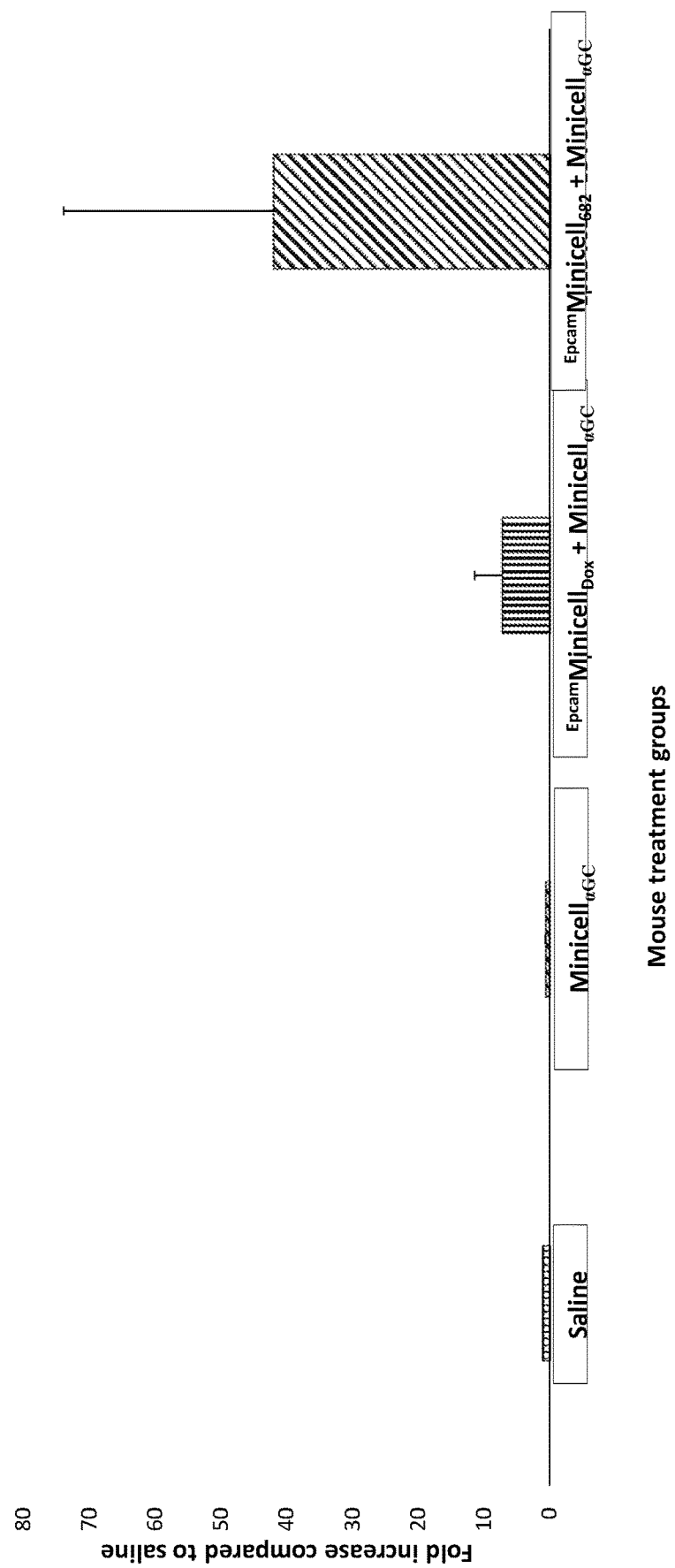
FIG. 18 shows CD1d mRNA expression in PBMCs 8h post-injection (fold increase as compared to saline) for four different mouse treatment groups: saline, Minicell$_{\alpha GC}$, $^{Epcam}$Minicell$_{Dox}$+Minicell$_{\alpha GC}$, and $^{Epcam}$Minicell$_{682}$+Minicell$_{\alpha GC}$.

Tissue pan dendritic cells were isolated from single-cell suspensions of the tumor xenografts and internal organs (spleen, thymus) using the Pan Dendritic Cell Isolation Kit, mouse (Miltenyi Biotec) following manufacturer's instructions. The cells were then counted using a haemocytometer and used for downstream processes. Isolates activated and non-activated DCs.
Results The result showed (FIG. 18) that both treatment groups, $^{EpCAM}$minicell$_{Dox}$+minicell$_{\alpha\text{-}GC}$ and $^{EpCAM}$minicell$_{682}$+minicell$_{\alpha\text{-}GC}$ had a significant increase in CD1d mRNA and the latter group show a further highly significant increase compared to the $^{EpCAM}$minicell$_{Dox}$+minicell$_{\alpha\text{-}GC}$ treatment.

Figure 19:
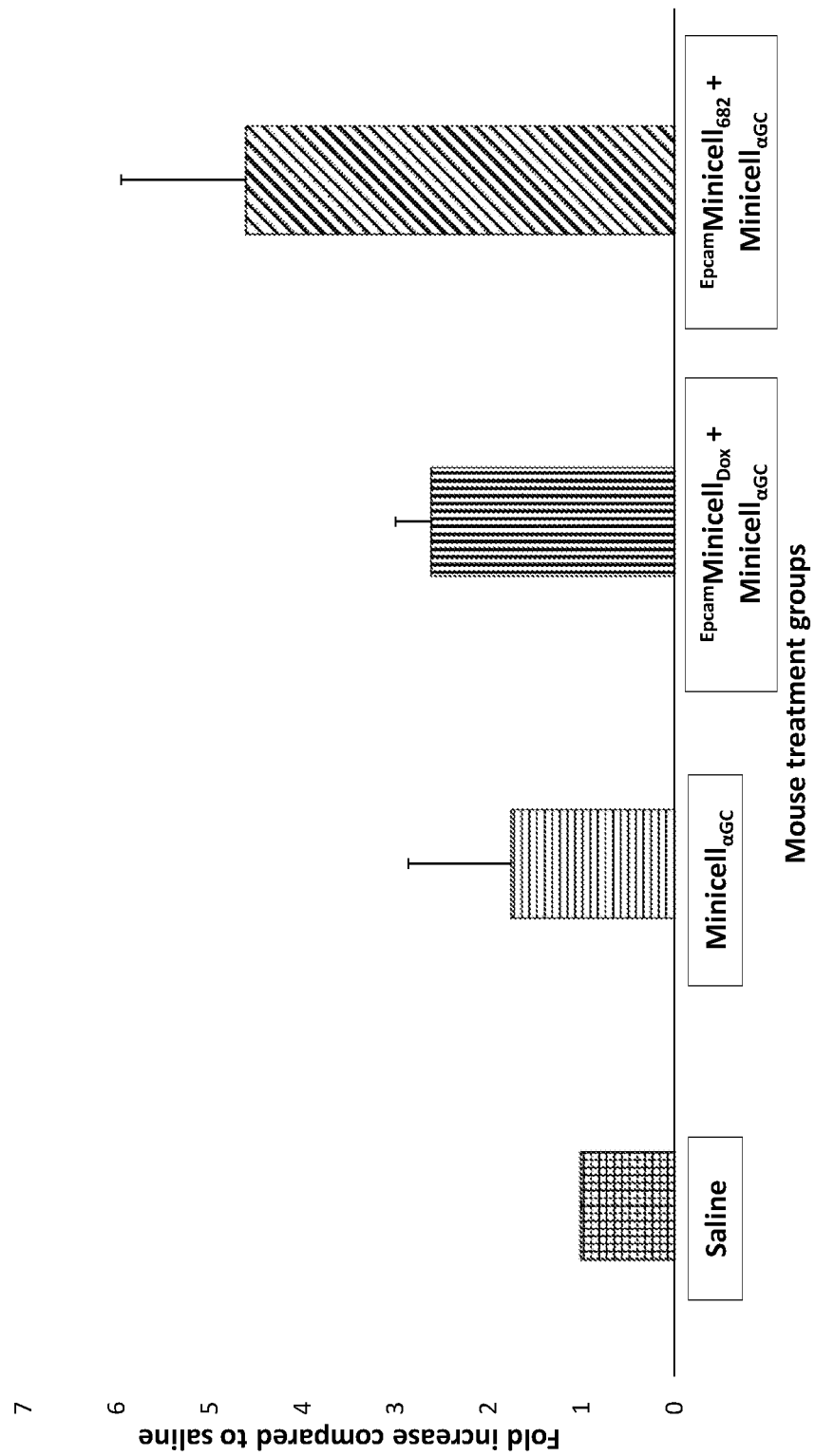
FIG. 19 shows CD1d mRNA expression in DCs isolated from thymus 8h post-injection (fold increase as compared to saline) for four different mouse treatment groups: saline, Minicell$_{\alpha GC}$, $^{Epcam}$Minicell$_{Dox}$+Minicell$_{\alpha GC}$, and $^{Epcam}$Minicell$_{682}$+Minicell$_{\alpha GC}$.

At the same time point, the CD1d mRNA expression was significantly increased in dendritic cells (FIG. 19) only in the group treated with $^{EpCAM}$minicell$_{682}$+minicell$_{\alpha\text{-}GC}$.

It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

CITED PUBLICATIONS

Ablasser et al., *Nat. Immunol.*, 10 (10):1065-72 (2009).
Ablasser et al., *Nature*, 498:380-384 (2013a).
Ablasser et al., *Nature*, 503:530-534 (2013b).
Adamus et al., *Contemp. Oncol (Ponzn)*, 22(1A):56-60 (2018).
Aduro Biotech Inc. (2016), Novartis Pharmaceuticals. *Study of the Safety and Efficacy of MIW815 (ADU-S100) in Patients with Advanced/Metastatic Solid Tumors or Lymphomas*. 2020. ClinicalTrials.gov [Internet]. Bethesda (Md.): National Library of Medicine (US). Identifier: NCT02675439. Available from: https://ClinicalTrials.gov/show/NCT02675439. (cited 1 Jul. 2016).
Ahmadzadehfar et al., *Semin Nucl Med.* 40(2):105-121 (2010).
Ahmadzadehfar et al., *Oncotarget* 7(11):12477-12488 (2016).
Alexopoulou et al., *Nature*, 413: 732-738 (2001).
Alzahrani et al., *Clin Nucl Med.* 37(3):229-234 (2012).
Anderson et al., *Molecules* 18:15662-15688 (2013).
Andersson et al., *Pept Sci.* 55:227-250 (2000).
Anguille et al., *Pharmacological Reviews* 67, 731-753 (2015).
Barber et al., *Curr. Opin. Immunol.*, 23(1): 10-20 (2011).
Belardelli et al., *TRENDS in Immunology* 23, 201-208 (2002).
Bernardini et al., *Frontiers in immunology* 7,402 (2016).
Birkholz et al., *J Biol Chem.* 290(25):15365-70 (2015).
Birkholz and Kronenberg, *Biomedical Journal* 38:470-482 (2015).
Bobanga et al., *Oncoimmunology* 7(3): e1393598 (2017).
Bredel, *Brain Res. Rev.* 35:161 (2001).
Britton et al., *Genes Dev.* 12:1254-9 (1998).
Brody et al., *J. Clin. Oncol.*, 28:4324-4332 (2010).
Burckstummer et al., *Nat. Immunol.*, 10:266-272 (2009).
Burger et al. *Blood* 106:1824-1830 (2005).
Caplen, N. J., *Expert Opin. Biol. Ther.* 3:575-86 (2003).
Caplen and Mousses, *Ann. NY Acad. Sci.* 1002:56-62 (2003).
Caravella and Lugovskoy, *Curr. Opin. Chem. Biol.* 14:520-28 (2010).
Carreno et al., *Clin Transl. Immunology* 5(4): e69 (2016).
Caskey et al., *J. Exp. Med.* 208:2357-2366 (2011).
Cauwels et al. *Cancer Research* 78, 463-474 (2018).
Chatalic et al. *J Nucl Med.* 56:1809-1812 (2015).
Chen et al., *Int. J. Cancer* 93: 107 (2001).
Chikuma et al., *Cancer Sci.* 108: 574-580 (2017).
Chiu et al., *Cell* 138:576-591 (2009).
Chu et al., *PLoS Biology* 4:1122-36 (2006).
Civril et al., *Nature* 498:332-337 (2013).
Clark-Curtiss and Curtiss, *Methods Enzymol.* 101:347-362 (1983).
Colonna et al., *Nat. Immunol.* 5:1219-1226 (2004).
Corrales et al., *Cell Rep.* 11:1018-1030 (2015).
Cory et al., *Cancer Commun.* 3(7): 207-12 (1991).
D'Aloia et al., *Cell Death & Disease* 9, 282 (2018).
D'Angiolella et al., *Cell*, 149:1023-34 (2012).
Da Silva et al., *Breast Cancer Res.*, 12: R46 (1-13) (2010).
Debinski et al., *J. Neurooncol.*, 48: 103-11 (2000).
Debinski and Gibo, *Mol. Med.*, 6: 440-49 (2000).
de Boer et al., *J. Bacteriol.*, 174(1): 63-70 (1992).

Deutscher SL. *Chem Rev.* 110:3196-3211 (2010).
Dine et al., *Asia-Pacific journal of oncology nursing* 4, 127-135 (2017).
Dobbs et al., *Cell Host Microbe*, 18(2): 15-24 (2015).
Dong et al., *International journal of molecular sciences* 17, 320 (2016).
Dowling et al., *PLoS One*, 8:e58164 (2013).
Dredge et al., *Cancer immunology, immunotherapy*: CII 51, 521-531 (2002).
Duan et al., *Mol. Cancer Ther.*, 3: 833-8 (2004).
Duxbury et al., *Ann. Surg.*, 240: 667-74 (2004).
Dynavax Technologies Corporation (2016). Study of SD-101 in Combination with Localized Low-dose Radiation in Patients with Untreated Low-grade B-cell Lymphoma. 2016. ClinicalTrials.gov [Internet]. Bethesda (Md.): National Library of Medicine (US). Identifier: NCT02266147. Available from: https://ClinicalTrials.gov/show/NCT02266147. (cited 1 Jul. 2016).
Emens et al., *European journal of cancer* 81, 116-129 (2017).
Erathodiyil and Ying, *Acc Chem Res.* 44:925-935 (2011)
Fang et al., *Seminars in immunology* 31, 37-54 (2017).
Farkona, et al., *BMC medicine* 14, 73 (2016).
Faveeuw et al., *Cancer Res.* 74(6): 1632-1638 (2014).
Ferlazzo et al. *The Journal of Immunology* 172, 1333-1339 (2004).
Fernandes-Alnemri et al., *Nature*, 458:509-513 (2009).
Field et al., *Proc. Natl Acad. Sci. USA*, 58: 1004-1010 (1967).
Fitzgerald-Bocarsly et al., *Biochimie* 89, 843-855 (2007).
Fu et al., *Sci. Transl. Med.*, 7(283):283ra252 (2015).
Fukuda, Curr. Protocols *Molec. Biol.* (Suppl. 26), 17.5.1-17.5.8 (1994).
Gao et al., *Nat Biotechnol.*, 22(8): 969-976 (2004).
Gao et al., *Science*, 341:903-906 (2013a).
Gao et al., *Cell*, 153:1094-1107 (2013b).
Gerard and Cavalieri, *Clin Nucl Med.* 27(1):1-8 (2002).
Ghosh and Heston, *J Cell Biochem.* 91(3):528-539 (2004).
Giaccone et al., *Clin. Cancer Res.* 8:3702-3709 (2002).
Gitlin et al., *Proc. Natl Acad. Sci. USA*, 103: 8459-8464 (2006).
Goh and Sorkin, *Cold Spring Harb. Perspect. Biol.*, 5: a017459 (2013).
Graversen and Moestrup, *Membranes* 5: 228-52 (2015).
Gray and Brown, *Chem Rev.* 114:1020-1081 (2013).
Gregory et al., *Methods in Molecular Biology*, 342: 33-47 (2006).
Gupta et al., "Abstract CT091: Safety and pharmacodynamic activity of MEDI9197, a TLR 7/8 agonist, administered intratumorally in subjects with solid tumors," Cancer Research, AACR Annual Meeting 2017; Apr. 1-5, 2017 (Published July 2017)).
Hansen et al., *EMBO J.*, 33(15): 1654-66 (2014).
Harry, E. J., *Mol. Microbiol.*, 40(4): 795-803 (2001).
He et al., *Materials Today Chemistry* 4: 106-16 (2017).
Hershey, *J. Allergy Clin. Immunol.*, 111: 677-90 (2003).
Hiraga et al., *J. Bacteriol.*, 171: 1496-1505 (1989).
Hobbs et al., *Proc. Natl. Acad. Sci. USA*, 95(8): 4607-4612 (1998).
Holman and Tumeh, *JAMA* 263(4):561-564 (1990).
Hornung et al., *Nature*, 458:514-518 (2009).
Hu & Lutkenhaus, *Mol. Microbio.*, 34(1): 82-90 (1999).
Iftode et al., *Crit. Rev. Biochem. Mol. Biol.*, 34: 141-80 (1999).
Igarashi et al., *Int J Clin Med.* 2:500-508 (2011).
Immune Design (2016), Merck Sharp & Dohme Corp. Study of Intratumoral G100 with or without Pembrolizumab in Patients with Follicular Non-Hodgkin's Lymphoma. 2017. ClinicalTrials.gov [Internet]. Bethesda (Md.): National Library of Medicine (US). Identifier: NCT02501473. Available from: https://ClinicalTrials.gov/show/NCT02501473. (cited 1 Jul. 2016).
Ireton et al., J. Bacteriol., 176: 5320-29 (1994).
Jarboe et al., *Cancer Res.*, 67: 7983-86 (2007).
Jenkins et al., *British journal of cancer* 118, 9-16 (2018).
Jung et al., *Translational oncology* 11, 686-690 (2018).
Kao et al., *Am. J. Respir. Crit. Care Med.*, 191(12): 1467-1469 (2015).
Kao et al., *American Journal of Respiratory and Critical Care Medicine* 191, 1467-1469 (2015).
Kawai and Akira, *Nat. Immunol.*, 11:373-384 (2010).
Kelly et al., *J. Drug Delivery* (2011).
Khalil et al., *Proc Nat'l Acad. USA*, 106: 11667-72 (2009).
Kim et al., *Proc. Natl. Acad. Sci. USA*, 107:15181-15186 (2010).
Kota et al., *Cell*, 137: 1005-17 (2009).
Kramer-Marek et al., Tumour Biol. 33(3):629-640 (2012).
Kranzusch et al., *Cell Rep.*, 3:1362-1368 (2013).
Krieg et al., *Nature*, 374: 546-549 (1995).
Kwekkeboom et al., *J Clin Oncol.* 26(13):2124-2130 (2008).
Landskron et al., *Journal of immunology research* 2014, 149185 (2014).
Lee et al., *Cancers* 3, 3856-3893 (2011).
Lemmon and Schlessinger, *Cell*, 141(7): 1117-134 (2010).
Leung and Amarasinghe, *Curr. Opin. Struct. Biol.*, 36:133-141 (2016).
Li et al., *Acta Biomater.* 73: 412-23 (2018).
Li et al., *Science*, 341:1390-1394 (2013b).
Liu et al., *Science*, 347(6227): aaa2630 (2015).
Lu et al., *Structure*, 18:1032-1043 (2010).
Ma et al., *Mol. Microbiol.*, 54: 99-108 (2004).
MacDiarmid et al., *PLoS One*, 11(4) (2016).
MacDiarmid et al. *Nature biotechnology* 27, 643-651 (2009).
MacDiarmid et al., *Cell cycle* 6, 2099-2105 (2007a).
MacDiarmid et al., *Cancer cell* 11, 431-445 (2007b).
Majkowska et al., *Appl Radiat Isot.* 67(1):11-13 (2009).
Mankan et al., *EMBO J.*, 33:2937-2946 (2014).
McWhirter et al., *J. Exp. Med.*, 206:1899-1911 (2009).
Marq et al., *J. Biol. Chem.*, 286:6108-6116 (2011).
Matsuno et al. *J Gastroenterol.* 32:579-586 (1997).
MedImmune LLC (2016). A Study of MEDI9197 Administered in Subjects with a Solid Tumor Cancer. 2018. ClinicalTrials.gov [Internet]. Bethesda (Md.): National Library of Medicine (US). Identifier: NCT02556463. Available from: https://ClinicalTrials.gov/show/NCT02556463. (cited 1 Jul. 2016).
Mellman et al., *Nature* 480, 480-489 (2011).
Merrifield, *Adv Enzymol Relat Areas Mol Biol.* 32:221-296 (2006).
Meulen and Brady, *Hum. Vaccin. Immunother.*, 13(1):15-16 (2017).
Mhawech-Fauceglia et al., *Histopathology* 50(4):472-483 (2007).
Morvan et al., *Nature reviews Cancer* 16, 7-19 (2016).
Muller et al., *Frontiers in immunology* 8,304 (2017).
Müller et al., *J Nucl Med.* 53(12):1951-1959 (2012).
Nakamura et al., *J. of Controlled Release* 171:216-224 (2013).
NHMRC Clinical Trials Centre, University of Sydney Australian New Zealand Clinical Trials Registry: Sydney (NSW): (2017)—Identifier ACTRN12617000037303 A Phase 1 Study of Anti-Human EGFR (Vectibix Sequence) Targeted EDVs Carrying the Cytotoxic Drug PNU- 159682 (EGFR(V)-EDV-PNU) with Concurrent Non-Targeted EDVs Carrying an Immunomodulatory Adjuvant (EDV-40mer) in Subjects with Advanced Solid Tumours who have No Curative Treatment Options 2017 Jan. 10; https://www.anzctr.org.au/ACT 12617000037303.aspx.
Nielsen et al, *Biochim. Biophys. Acta*, 1591(1-3), 109-118 (2002).
Nieth et al., *FEBS Lett.*, 545: 144-50 (2003).
Oh and Park, *Advanced Drug Delivery Rev.*, 61: 850-62 (2009).
Ohki-Hamazaki et al. *Int J Dev Biol.* 49:293-300 (2005).
Oiseth et al., *Journal of Cancer Metastasis and Treatment* 3,250 (2017).
Okada et al., *J. Bacteriol.*, 176: 917-22 (1994).
Okano et al., *J. Am. Chem. Soc.*, 128: 7136-37 (2006).
Oncovir Inc. (2016), National Institutes of Health, Icahn School of Medicine at Mount Sinai, Bay Hematology Oncology, Emory University, University of Pittsburgh, National Cancer Institute. In Situ, Autologous Therapeutic Vaccination Against Solid Cancers with Intratumoral Hiltonol®. 2018. ClinicalTrials.gov [Internet]. Bethesda (Md.): National Library of Medicine (US). Identifier: NCT02423863. Available from: https://ClinicalTrials.gov/show/NCT02423863. (cited 1 Jul. 2016).
Oritz-Zapater et al., *Nature Medicine*, 18(1):83-90 (2011).
Orzalli et al., *Proc. Natl. Acad. Sci. USA*, 109: E3008-E3017 (2012).
Park et al., *Breast Cancer Res.*, 4(3): 95-99 (2002).
Palmedo H. Radionuclide therapy of bone metastases. In: Biersack H J, Freeman L M, editors. Clinical Nuclear Medicine. Berlin, Heidelberg: Springer Berlin Heidelberg; 2007:433-442.
Pillai et al., *Appl Radiat Isot.* 59(2-3):109-118 (2003).
Quintieri et al., *Clinical Cancer Research* 11, 1608-1617 (2005).
Raskin & de Boer, *J. Bacteriol.*, 181: 6419-6424 (1999).
Reeve and Cornett, *J. Virol.*, 15: 1308-16 (1975).
Reid et al., *Annals of Oncology: Official Journal of the European Society for Medical Oncology* 24, 3128-3135 (2013).
Rezvani et al., *Molecular therapy: the journal of the American Society of Gene Therapy* 25, 1769-1781 (2017).
Rice et al., *Semin. Nucl. Med.*, 41: 265-282 (2011).
Ruoslahti, *Annu Rev Cell Dev Biol.* 12:697-715 (1996).
Sagnella et al., *Molecular cancer therapeutics* 17, 1012-1023 (2018).
Santoni et al., *J Biol Regul Homeost Agents.* 28(4):555-563 (2013).
Sawa-Wejksza et al., *Archivum immunologiae et therapiae experimentalis* 66, 97-111 (2018).
Sazar, "Activating the Natural Host Defense; Hiltonol (Poly-ICLC) and Malignant Brain Tumors, Oncovir, Inc., www.oncovir.com/id2 (accessed Jul. 11, 2018).
Sharma et al. *Cell* 168, 707-723 (2017).
Sharpe, *Immunological reviews* 276, 5-8 (2017).
Showalter, *Cytokine* 97, 123-132 (2017).
Silver et al., *Clin Cancer Res.* 3(1):81-85 (197).
Simmons et al. *The Journal of Immunology* 188, 3116-3126 (2012).
Singh, *Biomed Res Int.* 2014:874610 (2014).
Sioud, M., *Trends Pharmacol. Sci.*, 25: 22-8 (2004).
Schoggins et al., *Nature*, 505:691-695 (2014).
Solomon et al., *PLos One*, 10: 1-17 (2015).
Staudacher et al., *British journal of cancer* 117, 1736-1742 (2017).
Strand, F L. Neuropeptides: Regulators of Physiological Processes. MIT press; 1999.
Stewart and D'Ari, *J. Bacteriol.*, 174: 4513-6 (1992).
Sun et al., *Science*, 339(6121):786-791 (2013).
Sun et al., *Biochem. Biophys. Res. Commun.*, 280: 788 (2001).
Sun et al., *Adv Drug Deliv Rev.* 110-111: 38-51 (2017).
Szkandera et al., *British journal of cancer* 110, 183-188 (2014).
Takahashi et al., *Adv Funct Mater.* 18:2079-2088 (2008).
Takaoka et al., *Nature*, 448:501-505 (2007).
Takeshita et al., *Molec. Ther.*, 18: 181-87 (2010).
Tanpure et al., *Bioorg. Med. Chem.*, 21: 8019-32 (2013).
Tatemoto, K. Neuropeptide Y: history and overview, Neuropeptide Y and Related Peptides. Springer; 2004. p. 1-21.
Teunissen et al., *Best Pract Res Clin Gastroenterol.* 19(4): 595-616 (2005).
Tyler-McMahon et al. *Regul Pept.* 93:125-136 (2000).
Unterholzner et al., *Nat. Immunol.*, 11:997-1004 (2010).
Unterholzner et al., *Immunobiology*, 128(11): 1312-21 (2013).
van Zandwijk et al., *Lancet Oncol.*, 18(10): 1386-1396 (2017).
van Zandwijk et al., *The Lancet Oncology* 18, 1386-1396 (2017).
Ventola, *Pharmacy and Therapeutics* 42, 452-463 (2017).
Wallace et al., *Springer seminars in immunopathology* 27, 49-64 (2005).
Walrand et al., *J Nucl Med.* 56(3):494-495 (2015).
Wang et al., *Nat. Struct. Mol. Biol.*, 17:781-787 (2010).
Wang et al., *Immunity*, 41(6): 919-33 (2014).
Weckbecker et al., *Nat Rev Drug Discov.* 2:999-1017 (2003).
White & McCubrey, *Leukemia*, 15: 1011-1021 (2001).
Whittle et al., *J. Clin. Neurosci.*, 22(12): 1889-1894 (2015).
Whittle et al., *Journal of clinical neuroscience: official journal of the Neurosurgical Society of Australasia* 22, 1889-1894 (2015).
Wu et al., *Science*, 339:826-830 (2013).
Wykosky et al., *Clin Cancer Res.*, 14: 199-208 (2008).
Xia et al., *Nat. Immunol.*, 16:366-375 (2015).
Yague et al., *Gene Ther.*, 11: 1170-74 (2004).
Yang et al., *Clin Cancer Res.* 14:5494-5502 (2008).
Yang et al., *Nat. Immunol.*, 11:487-494 (2010).
Yi et al., *PLoS One*, 8(10):e77846 (2013).
Yuan et al., *Scientific reports* 5, 14273 (2015).
Zhang et al., *J. Immunol.*, 186:4541-4545 (2011a).
Zhang et al., *Nat. Immunol.*, 12:959-965 (2011b).
Zhang et al., *Cell Rep.*, 6:421-430 (2014).
Zibert et al., *Human Gene Therapy* 15, 21-34 (2004).
Ziegler-Heitbrock et al., *Frontiers in immunology* 4, 23 (2013).
Zitvogel et al., *Nature reviews Immunology* 15, 405-414 (2015).
U.S. Pat. No. 8,591,862.
U.S. Pat. No. 7,183,105.
US2008/0051469.
US2008/0038296
US2015/0283235
US2017/0368002
WO 2000/067776.
WO 2003/033519.
WO 2004/113507.
WO 2005/056749.
WO 2005/079854.
WO 2009/027830.

What is claimed is:

1. An adjuvant composition comprising:
   (a) an immunogenically effective amount of intact, bacterially derived minicells or killed bacterial cells that encapsulate a CD1d-restricted invariant Natural Killer T (iNKT) cell antigen;
   (b) intact, bacterially derived minicells or killed bacteria cells that encapsulate an antineoplastic agent; and
   (c) at least one pharmaceutically acceptable carrier,
   wherein the intact bacterially-derived minicells comprising a CD1d-restricted iNKT cell antigen do not comprise a targeting agent, and the intact, bacterially-derived minicells comprising an antineoplastic agent comprise a targeting agent, and
   wherein the CD1d-restricted iNKT cell antigen is a glycosphingolipid selected from the group consisting of α-galactosylceramide (α-GalCer), C-glycosidific form of α-galactosylceramide (α-C-GalCer), 12 carbon acyl form of galactosylceramide (β-GalCer), β-D-glucopyranosylceramide (β-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), a-glucuronosylceramide (GSL-1 or GSL-4), isoglobotrihexosylceramide (iGb3), lipophosphoglycan (LPG), lyosphosphatidylcholine (LPC), α-galactosylceramide analog (OCH), and threitolceramide.

2. The adjuvant composition of claim 1, wherein:
   (a) the encapsulated CD1d-restricted iNKT cell antigen is capable of uptake by a phagocytic cell; and/or
   (b) the encapsulated CD1d-restricted iNKT cell antigen is capable of uptake by a phagocytic cell and wherein the phagocytic cell is a dendritic cell or a macrophage.

3. The adjuvant composition of claim 1, wherein the CD1d-restricted iNKT cell antigen:
   (a) induces a Th1 cytokine response by an iNKT cell that recognizes the antigen presented by CD1d; and/or
   (b) is a glycosphingolipid which is α-GalCer; and/or
   (c) is a glycosphingolipid which is a synthetic α-GalCer analog, wherein the synthetic α-GalCer analog is selected from the group consisting of 6'-deoxy-6'-acetamide α-GalCer (PBS57), naphtylurea α-GalCer (NU-α-GC), NC-α-GalCer, 4ClPhC-α-GalCer, PyrC-α-GalCer, α-carba-GalCer, carba-α-D-galactose α-GalCer analog (RCAI-56), 1-deoxy-neo-inositol α-GalCer analog (RCAI-59), 1-O-methylated α-GalCer analog (RCAI-92), and HS44 aminocyclitol ceramide.

4. The adjuvant composition of claim 1, wherein the antineoplastic agent is:
   (a) is selected from the group consisting of a radionuclide, a chemotherapy drug, a functional nucleic acid, and a polynucleotide from which a functional nucleic acid can be transcribed; and/or
   (b) a cytotoxin; and/or
   (c) selected from the group consisting of morpholinyl anthracycline, a maytansinoid, duocarmycin, auristatins, calicheamicins (DNA damaging agents), α-amanitin (RNA polymerase II inhibitor), centanamycin, pyrrolobenzodiazepine, streptonigtin, nitrogen mustards, nitrosorueas, alkane sulfonates, pyrimidine analogs, purine analogs, antimetabolites, folate analogs, anthracyclines, taxanes, *vinca* alkaloids, topoisomerase inhibitors, hormonal agents, and a combination thereof; and/or
   (d) a morpholinyl anthracycline selected from the group consisting of nemorubicin, PNU-159682, idarubicin, daunorubicin, caminomycin, and doxorubicin; and/or
   (e) a functional nucleic acid selected from the group consisting of a siRNA, a miRNA, a shRNA, a lincRNA, an antisense RNA, and a ribozyme.

5. The adjuvant composition of claim 1, wherein:
   (a) the targeting agent is a bispecific ligand; and/or
   (b) the targeting agent is a bispecific ligand and the bispecific ligand comprises a first arm that carries specificity for a minicell surface structure and a second arm that carries specificity for a non-phagocytotic mammalian cell surface receptor; and/or
   (c) the targeting agent is a bispecific ligand and the bispecific ligand comprises a first arm that carries specificity for a minicell surface structure and a second arm that carries specificity for a non-phagocytotic mammalian cell surface receptor, wherein the minicell surface structure is an O-polysaccharide component of a lipopolysaccharide on the minicell surface; and/or
   (d) the non-phagocytotic mammalian cell surface receptor of (b) or (c) is capable of activating macropinocytosis of the minicell or killed bacterial cell.

6. The adjuvant composition of claim 5, wherein:
   (a) the bispecific ligand comprises a bispecific antibody or antibody fragment; and/or
   (b) the bispecific ligand comprises a bispecific antibody or antibody fragment and wherein the antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating macropinocytosis of the minicell.

7. A method for treating a neoplastic disease comprising administering to a subject in need thereof:
   (a) an immunogenically effective amount of intact, bacterially derived minicells or killed bacterial cells that encapsulate a CD1d-restricted invariant Natural Killer T (iNKT) cell antigen; and
   (b) intact, bacterially derived minicells comprising an antineoplastic agent or therapy that induces the death of neoplastic cells in the subject,
   wherein the intact bacterially-derived minicells comprising an CD1d-restricted iNKT cell antigen do not comprise a targeting agent, and the intact bacterially-derived minicells comprising an antineoplastic agent comprises a targeting agent, and
   wherein the CD1d-restricted iNKT cell antigen is a glycosphingolipid selected from the group consisting of α-galactosylceramide (α-GalCer), C-glycosidific form of α-galactosylceramide (α-C-GalCer), 12 carbon acyl form of galactosylceramide (β-GalCer), β-D-glucopyranosylceramide (β-GlcCer), 1,2-Diacyl-3-O-galactosyl-sn-glycerol (BbGL-II), diacylglycerol containing glycolipids (Glc-DAG-s2), ganglioside (GD3), gangliotriaosylceramide (Gg3Cer), glycosylphosphatidylinositol (GPI), α-glucuronosylceramide (GSL-1 or GSL-4), isoglobotrihexosylceramide (iGb3), lipophosphoglycan (LPG), lyosphosphatidylcholine (LPC), α-galactosylceramide analog (OCH), and threitolceramide.

8. The method of claim 7, wherein:
   (a) the encapsulated CD1d-restricted iNKT cell antigen is capable of uptake by a phagocytic cell; and/or
   (b) the phagocytic cell is a dendritic cell or a macrophage; and/or (c) the CD1d-restricted iNKT cell antigen induces a Th1 cytokine response by an iNKT cell that recognizes the antigen presented by CD1d; and/or
(d) the CD1d-restricted iNKT cell antigen is a glycosphingolipid and the glycosphingolipid is α-GalCer; and/or
(e) the CD1d-restricted iNKT cell antigen is a glycosphingolipid and the glycosphingolipid is a synthetic α-GalCer analog; and/or
(f) the CD1d-restricted iNKT cell antigen is a glycosphingolipid and the glycosphingolipid is a synthetic α-GalCer analog which is selected from among 6'-deoxy-6'-acetamide α-GalCer (PBS57), naphtylurea α-GalCer (NU-α-GC), NC-α-GalCer, 4ClPhC-α-GalCer, PyrC-α-GalCer, α-carba-GalCer, carba-α-D-galactose α-GalCer analog (RCAI-56), 1-deoxy-neo-inositol α-GalCer analog (RCAI-59), 1-O-methylated α-GalCer analog (RCAI-92), and HS44 aminocyclitol ceramide.

9. The method of claim 7, wherein:
(a) the therapy that induces the death of neoplastic cells comprises administration of an antineoplastic agent; and/or
(b) the therapy that induces the death of neoplastic cells comprises administration of an antineoplastic agent and wherein the antineoplastic agent is selected from the group consisting of a radionuclide, a chemotherapy drug, a functional nucleic acid, and a polynucleotide from which a functional nucleic acid can be transcribed; and/or
(c) the therapy that induces the death of neoplastic cells comprises administration of an antineoplastic agent and wherein the antineoplastic agent is:
  (i) a cytotoxin; or
  (ii) selected from the group consisting of morpholinyl anthracycline, a maytansinoid, duocarmycin, auristatins, calicheamicins (DNA damaging agents), α-amanitin (RNA polymerase II inhibitor), centanamycin, pyrrolobenzodiazepine, streptonigtin, nitrogen mustards, nitrosorueas, alkane sulfonates, pyrimidine analogs, purine analogs, antimetabolites, folate analogs, anthracyclines, taxanes, vinca alkaloids, topoisomerase inhibitors, hormonal agents, and a combination thereof; or
  (iii) a morpholinyl anthracycline selected from the group consisting of nemorubicin, PNU-159682, idarubicin, daunorubicin, caminomycin, and doxorubicin; or
  (iv) a functional nucleic acid selected from the group consisting of a siRNA, a miRNA, a shRNA, a lincRNA, an antisense RNA, and a ribozyme, and optionally wherein the functional nucleic acid inhibits a gene that promotes tumor cell proliferation, angiogenesis or resistance to chemotherapy and/or that inhibits apoptosis or cell cycle arrest.

10. The method of claim 7, wherein:
(a) the targeting agent is a bispecific ligand; and/or
(b) the targeting agent is a bispecific ligand and wherein the bispecific ligand comprises a first arm that carries specificity for a minicell surface structure and a second arm that carries specificity for a non-phagocytotic mammalian cell surface receptor;
(c) the targeting agent is a bispecific ligand and wherein the bispecific ligand comprises a first arm that carries specificity for a minicell surface structure and a second arm that carries specificity for a non-phagocytotic mammalian cell surface receptor, wherein the minicell surface structure is an O-polysaccharide component of a lipopolysaccharide on the minicell surface; and/or
(d) the non-phagocytotic mammalian cell surface receptor of (b) or (c) is capable of activating macropinocytosis of the minicell; and/or
(e) the targeting agent is a bispecific ligand and the bispecific ligand comprises a bispecific antibody or antibody fragment; and/or
(f) the targeting agent is a bispecific ligand and the bispecific ligand comprises a bispecific antibody or antibody fragment, wherein the antibody or antibody fragment comprises a first multivalent arm that carries specificity for a bacterially derived minicell surface structure and a second multivalent arm that carries specificity for a cancer cell surface receptor, wherein the cancer cell surface receptor is capable of activating macropinocytosis of the minicell.

11. The method of claim 7, wherein the antineoplastic agent or therapy that induces the death of neoplastic cells comprises CAR T cell therapy, oncolytic virus therapy, radiation therapy, or surgery.

12. The method of claim 7, wherein:
(a) the encapsulated CD1d-restricted iNKT cell antigen and the antineoplastic agent or therapy that induces the death of neoplastic cells are administered simultaneously; and/or
(b) wherein the encapsulated CD1d-restricted iNKT cell antigen and the antineoplastic agent or therapy that induces the death of neoplastic cells are administered sequentially; and/or
(c) the encapsulated CD1d-restricted iNKT cell antigen and the antineoplastic agent or therapy that induces the death of neoplastic cells are administered in the same composition; and/or
(d) the encapsulated CD1d-restricted iNKT cell antigen and the antineoplastic agent or therapy that induces the death of neoplastic cells are administered in separate compositions.

13. The method of claim 7, wherein the subject is a mammal, a human, a non-human primate, a dog, a cat, a cow, a sheep, a horse, a rabbit, a mouse, or a rat.

14. The method of claim 7, wherein:
(a) the neoplastic disease is cancer;
(b) the neoplastic disease is cancer and wherein the cancer is selected from the group consisting of lung cancer, breast cancer, brain cancer, liver cancer, colon cancer, pancreatic cancer, and bladder cancer;
(c) the neoplastic disease is cancer and wherein the cancer selected from the group consisting of an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor; breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonaryblastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymiccarcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; and Wilms' tumor; and/or
(d) the neoplastic disease is cancer and wherein the cancer is malignant; and/or
(e) the neoplastic disease is cancer and wherein the cancer is a recurrent or relapsed cancer.

15. The method of claim 7, wherein:
(a) the encapsulated CD1d-restricted iNKT cell antigen and/or the antineoplastic agent or therapy that induces the death of neoplastic cells is/are administered multiple times; and/or
(b) the encapsulated CD1d-restricted iNKT cell antigen and/or the antineoplastic agent or therapy that induces the death of neoplastic cells is/are administered at least once a week over the course of several weeks; and/or
(c) the encapsulated CD1d-restricted iNKT cell antigen and/or the antineoplastic agent or therapy that induces the death of neoplastic cells is/are administered at least once a week over several weeks to several months; and/or
(d) the encapsulated CD1d-restricted iNKT cell antigen and/or the antineoplastic agent or therapy that induces the death of neoplastic cells is/are administered at least once a week for about 2, about 3, about 4, about 5, about 6, about 7, about 8, about 9, about 10, about 11, about 12, about 13, about 14, about 15, about 16, about 17, about 18, about 19 or about 20 weeks or more; and/or
(e) the encapsulated CD1d-restricted iNKT cell antigen and/or the antineoplastic agent or therapy that induces the death of neoplastic cells is/are administered about twice every week; and/or
(f) the encapsulated CD1d-restricted iNKT cell antigen and/or the antineoplastic agent or therapy that induces the death of neoplastic cells is/are administered twice a week for about 2, about 3, about 4, about 5, about 6, about 7, about 8, about 9, about 10, about 11, about 12, about 13, about 14, about 15, about 16, about 17, about 18, about 19 or about 20 weeks or more.

16. The adjuvant composition of claim 1, wherein the CD1d-restricted iNKT cell antigen is α-GalCer.

17. The adjuvant composition of claim 16, wherein:
(a) the composition further comprises at least one antineoplastic agent which is a morpholinyl anthracycline;
(c) the antineoplastic agent is comprised in an intact bacterially-derived minicell or killed bacterial cell;
(b) the intact bacterially-derived minicell comprising the antineoplastic agent further comprises a targeting agent;
(d) the targeting agent is a bispecific antibody and:
  (i) the bispecific antibody comprises a first arm that carries specificity for a minicell surface structure and a second arm that carries specificity for either a non-phagocytotic mammalian cell surface receptor, or
  (ii) the bispecific antibody comprises a first multivalent arm that carries specificity for a bacterially derived minicell surface structure and a second multivalent arm that carries specificity for a cancer cell surface receptor;
(e) the minicell surface structure is an O-polysaccharide component of a lipopolysaccharide on the minicell surface; and
(f) the cancer cell surface receptor is capable of activating macropinocytosis of the minicell.

18. The adjuvant composition of claim 4, wherein the functional nucleic acid (i) inhibits a gene that promotes tumor cell proliferation, angiogenesis or resistance to chemotherapy and/or (ii) inhibits apoptosis or cell cycle arrest.

* * * * *